US008679090B2

(12) United States Patent
Anderson et al.

(10) Patent No.: US 8,679,090 B2
(45) Date of Patent: Mar. 25, 2014

(54) MEDICAL CONNECTOR WITH CLOSEABLE LUER CONNECTOR

(75) Inventors: Harold Anderson, Wildomar, CA (US); Christopher Lopez, Laguna Beach, CA (US); Thomas F. Fangrow, Jr., Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 641 days.

(21) Appl. No.: 12/641,283

(22) Filed: Dec. 17, 2009

(65) Prior Publication Data

US 2010/0174242 A1 Jul. 8, 2010

Related U.S. Application Data

(60) Provisional application No. 61/139,514, filed on Dec. 19, 2008.

(51) Int. Cl.
*A61M 39/00* (2006.01)

(52) U.S. Cl.
USPC ........... 604/533; 604/249; 604/256; 604/246; 604/536; 604/539; 604/537

(58) Field of Classification Search
USPC .......... 604/536–537, 539, 533, 256, 246, 249
See application file for complete search history.

(56) References Cited

U.S. PATENT DOCUMENTS

| 2,842,382 A | 7/1958 | Franck |
| 2,931,668 A | 4/1960 | Baley |
| 2,968,497 A | 1/1961 | Treleman |
| 3,127,892 A | 4/1964 | Bellamy, Jr. et al. |
| 3,304,047 A | 2/1967 | Martin |
| 3,334,860 A | 8/1967 | Bolton, Jr. |
| 3,707,972 A | 1/1973 | Villari et al. |
| 3,729,031 A | 4/1973 | Baldwin |
| 3,986,508 A | 10/1976 | Barrington |
| 4,055,179 A | 10/1977 | Manschot et al. |
| 4,066,067 A | 1/1978 | Micheli |
| 4,076,285 A | 2/1978 | Martinez |
| 4,080,965 A | 3/1978 | Phillips |

(Continued)

FOREIGN PATENT DOCUMENTS

| EP | 0 791 371 A1 | 8/1997 |
| EP | 1 946 792 | 7/2008 |

(Continued)

OTHER PUBLICATIONS

U.S. Appl. No. 11/417,923, filed May 3, 2006, Gustus et al.

(Continued)

*Primary Examiner* — Bhisma Mehta
*Assistant Examiner* — Edelmira Bosques
(74) *Attorney, Agent, or Firm* — Knobbe Martens Olson & Bear LLP

(57) ABSTRACT

Some embodiments disclosed herein relate to a medical connector having a selectively closable male end portion. Embodiments are configured to open upon connection with a female connector or female tipped medical implement. Some embodiments include an internal cavity configured to change size as the connector moves from the open to closed or closed to open positions. In some embodiments, the connector is configured to draw fluid from the male end toward the other end of the connector as the connector closes.

19 Claims, 19 Drawing Sheets

(56) References Cited

U.S. PATENT DOCUMENTS

| | | |
|---|---|---|
| 4,084,606 A | 4/1978 | Mittleman |
| 4,121,585 A | 10/1978 | Becker, Jr. |
| 4,133,441 A | 1/1979 | Mittleman et al. |
| 4,143,853 A | 3/1979 | Abramson |
| 4,150,845 A | 4/1979 | Kopacz et al. |
| 4,195,632 A | 4/1980 | Parker et al. |
| 4,233,982 A | 11/1980 | Bauer et al. |
| 4,245,635 A | 1/1981 | Kontos |
| 4,324,239 A | 4/1982 | Gordon et al. |
| 4,334,551 A | 6/1982 | Pfister |
| 4,340,049 A | 7/1982 | Munsch |
| 4,379,458 A | 4/1983 | Bauer et al. |
| 4,387,879 A | 6/1983 | Tauschinski |
| 4,397,442 A | 8/1983 | Larkin |
| 4,430,073 A | 2/1984 | Bemis et al. |
| 4,436,125 A | 3/1984 | Blenkush |
| 4,457,749 A | 7/1984 | Bellotti et al. |
| 4,511,359 A | 4/1985 | Vaillancourt |
| 4,538,836 A | 9/1985 | Kruetten |
| 4,610,469 A | 9/1986 | Wolff-Mooij |
| 4,619,640 A | 10/1986 | Potolsky et al. |
| 4,623,332 A | 11/1986 | Lindmayer et al. |
| 4,629,159 A | 12/1986 | Wellenstam |
| 4,660,803 A | 4/1987 | Johnston et al. |
| 4,662,878 A | 5/1987 | Lindmayer |
| 4,700,744 A | 10/1987 | Rutter et al. |
| 4,723,603 A | 2/1988 | Plummer |
| 4,728,075 A | 3/1988 | Paradis |
| 4,745,950 A | 5/1988 | Mathieu |
| 4,774,964 A | 10/1988 | Bonaldo |
| 4,774,965 A | 10/1988 | Rodriguez et al. |
| 4,781,702 A | 11/1988 | Herrli |
| 4,804,015 A | 2/1989 | Albinsson |
| 4,816,024 A | 3/1989 | Sitar et al. |
| 4,834,271 A | 5/1989 | Litwin |
| 4,862,913 A | 9/1989 | Wildfang |
| 4,883,483 A | 11/1989 | Lindmayer |
| 4,915,687 A | 4/1990 | Sivert |
| 4,917,669 A | 4/1990 | Bonaldo |
| 4,935,010 A | 6/1990 | Cox et al. |
| 4,950,260 A | 8/1990 | Bonaldo |
| D313,277 S | 12/1990 | Haining |
| D314,050 S | 1/1991 | Sone |
| 5,006,114 A | 4/1991 | Rogers et al. |
| 5,021,059 A | 6/1991 | Kensey et al. |
| 5,047,021 A | 9/1991 | Utterberg |
| 5,065,783 A | 11/1991 | Ogle, II |
| 5,070,885 A | 12/1991 | Bonaldo |
| 5,098,385 A | 3/1992 | Walsh |
| 5,108,376 A | 4/1992 | Bonaldo |
| 5,122,123 A | 6/1992 | Vaillancourt |
| 5,139,483 A | 8/1992 | Ryan |
| 5,147,333 A | 9/1992 | Raines |
| 5,154,703 A | 10/1992 | Bonaldo |
| RE34,223 E | 4/1993 | Bonaldo |
| 5,199,948 A | 4/1993 | McPhee |
| 5,201,725 A | 4/1993 | Kling |
| 5,203,775 A | 4/1993 | Frank et al. |
| 5,211,634 A | 5/1993 | Vaillancourt |
| 5,215,537 A | 6/1993 | Lynn et al. |
| 5,215,538 A | 6/1993 | Larkin |
| 5,242,393 A | 9/1993 | Brimhall et al. |
| 5,242,425 A | 9/1993 | White et al. |
| 5,251,873 A | 10/1993 | Atkinson et al. |
| 5,269,771 A | 12/1993 | Thomas et al. |
| 5,273,533 A | 12/1993 | Bonaldo |
| 5,279,571 A | 1/1994 | Larkin |
| 5,281,206 A | 1/1994 | Lopez |
| 5,284,475 A | 2/1994 | Mackal |
| 5,295,657 A | 3/1994 | Atkinson |
| 5,301,686 A | 4/1994 | Newman |
| 5,306,243 A | 4/1994 | Bonaldo |
| 5,312,377 A | 5/1994 | Dalton |
| 5,324,270 A | 6/1994 | Kayan et al. |
| 5,330,450 A | 7/1994 | Lopez |
| 5,334,159 A | 8/1994 | Turkel |
| 5,344,414 A | 9/1994 | Lopez et al. |
| 5,360,413 A | 11/1994 | Leason et al. |
| 5,370,636 A | 12/1994 | Von Witzleben |
| 5,380,306 A | 1/1995 | Brinon |
| 5,385,372 A | 1/1995 | Utterberg |
| 5,390,898 A | 2/1995 | Smedley et al. |
| 5,391,150 A | 2/1995 | Richmond |
| 5,395,348 A | 3/1995 | Ryan |
| 5,397,314 A | 3/1995 | Farley et al. |
| 5,400,500 A | 3/1995 | Behnke et al. |
| 5,401,245 A | 3/1995 | Haining |
| 5,402,826 A | 4/1995 | Molnar et al. |
| 5,402,982 A | 4/1995 | Atkinson et al. |
| 5,405,323 A | 4/1995 | Rogers et al. |
| 5,405,331 A | 4/1995 | Behnke et al. |
| 5,405,333 A | 4/1995 | Richmond |
| 5,411,499 A | 5/1995 | Dudar et al. |
| 5,417,673 A | 5/1995 | Gordon |
| 5,423,791 A | 6/1995 | Bartlett |
| 5,425,465 A | 6/1995 | Healy |
| 5,433,330 A | 7/1995 | Yatsko et al. |
| 5,439,451 A | 8/1995 | Collinson et al. |
| 5,441,487 A | 8/1995 | Vedder |
| 5,445,623 A | 8/1995 | Richmond |
| 5,456,668 A | 10/1995 | Ogle, II |
| 5,456,675 A | 10/1995 | Wolbring et al. |
| 5,462,255 A | 10/1995 | Rosen et al. |
| 5,464,399 A | 11/1995 | Boettger |
| 5,470,319 A | 11/1995 | Mayer |
| 5,470,327 A | 11/1995 | Helgren et al. |
| 5,474,536 A | 12/1995 | Bonaldo |
| 5,480,393 A | 1/1996 | Bommarito |
| 5,492,147 A | 2/1996 | Challender et al. |
| 5,501,426 A | 3/1996 | Atkinson et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,527,284 A | 6/1996 | Ohnemus et al. |
| 5,533,708 A | 7/1996 | Atkinson et al. |
| 5,533,983 A | 7/1996 | Haining |
| 5,535,785 A | 7/1996 | Werge et al. |
| 5,540,661 A | 7/1996 | Tomisaka et al. |
| 5,549,566 A | 8/1996 | Elias et al. |
| 5,549,577 A | 8/1996 | Siegel et al. |
| 5,549,651 A | 8/1996 | Lynn |
| 5,552,118 A | 9/1996 | Mayer |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,616,129 A | 4/1997 | Mayer |
| 5,616,130 A | 4/1997 | Mayer |
| RE35,539 E | 6/1997 | Bonaldo |
| 5,643,224 A | 7/1997 | Szapiro et al. |
| 5,645,538 A | 7/1997 | Richmond |
| 5,674,206 A | 10/1997 | Allton et al. |
| 5,676,346 A | 10/1997 | Leinsing |
| 5,685,866 A | 11/1997 | Lopez |
| 5,685,868 A | 11/1997 | Lundquist |
| 5,699,821 A | 12/1997 | Paradis |
| 5,700,248 A | 12/1997 | Lopez |
| 5,702,374 A | 12/1997 | Johnson |
| 5,735,826 A | 4/1998 | Richmond |
| 5,738,144 A | 4/1998 | Rogers |
| 5,749,861 A | 5/1998 | Guala et al. |
| RE35,841 E | 7/1998 | Frank et al. |
| 5,782,816 A | 7/1998 | Werschmidt et al. |
| 5,785,693 A | 7/1998 | Haining |
| 5,806,831 A | 9/1998 | Paradis |
| 5,814,024 A | 9/1998 | Thompson et al. |
| 5,820,601 A | 10/1998 | Mayer |

(56) References Cited

U.S. PATENT DOCUMENTS

| | | |
|---|---|---|
| 5,839,715 A | 11/1998 | Leinsing |
| 5,848,994 A | 12/1998 | Richmond |
| 5,947,954 A | 9/1999 | Bonaldo |
| 6,029,946 A | 2/2000 | Doyle |
| 6,036,171 A | 3/2000 | Weinheimer et al. |
| 6,050,978 A * | 4/2000 | Orr et al. ............... 604/249 |
| 6,063,062 A | 5/2000 | Paradis |
| 6,068,011 A | 5/2000 | Paradis |
| 6,068,617 A | 5/2000 | Richmond |
| 6,079,432 A | 6/2000 | Paradis |
| 6,106,502 A | 8/2000 | Richmond |
| 6,113,068 A | 9/2000 | Ryan |
| 6,142,446 A | 11/2000 | Leinsing |
| 6,152,913 A | 11/2000 | Feith et al. |
| 6,168,137 B1 | 1/2001 | Paradis |
| 6,171,287 B1 | 1/2001 | Lynn et al. |
| 6,189,859 B1 | 2/2001 | Rohrbough et al. |
| 6,206,860 B1 | 3/2001 | Richmond |
| 6,224,578 B1 | 5/2001 | Davis et al. |
| 6,242,393 B1 | 6/2001 | Ishida et al. |
| 6,245,048 B1 | 6/2001 | Fangrow et al. |
| 6,290,206 B1 | 9/2001 | Doyle |
| 6,299,132 B1 | 10/2001 | Weinheimer et al. |
| 6,428,520 B1 | 8/2002 | Lopez |
| 6,431,219 B1 | 8/2002 | Redler et al. |
| 6,485,472 B1 | 11/2002 | Richmond |
| 6,499,719 B1 | 12/2002 | Clancy et al. |
| 6,508,792 B2 | 1/2003 | Szames et al. |
| 6,508,807 B1 | 1/2003 | Peters |
| 6,541,802 B2 | 4/2003 | Doyle |
| 6,543,745 B1 | 4/2003 | Enerson |
| 6,581,906 B2 | 6/2003 | Pott et al. |
| 6,585,229 B2 | 7/2003 | Cote et al. |
| 6,595,964 B2 | 7/2003 | Finley et al. |
| 6,595,981 B2 | 7/2003 | Huet |
| 6,609,696 B2 | 8/2003 | Enerson |
| 6,666,852 B2 | 12/2003 | Niedospial, Jr. |
| 6,695,817 B1 | 2/2004 | Fangrow |
| 6,745,998 B2 | 6/2004 | Doyle |
| 6,840,501 B2 | 1/2005 | Doyle |
| 6,869,426 B2 | 3/2005 | Ganem |
| 6,875,205 B2 | 4/2005 | Leinsing |
| 6,899,315 B2 | 5/2005 | Maiville et al. |
| 6,955,669 B2 | 10/2005 | Curutcharry |
| 6,964,406 B2 | 11/2005 | Doyle |
| 7,004,934 B2 | 2/2006 | Vaillancourt |
| 7,037,302 B2 | 5/2006 | Vaillancourt |
| 7,040,598 B2 | 5/2006 | Raybuck |
| 7,044,441 B2 | 5/2006 | Doyle |
| 7,100,891 B2 | 9/2006 | Doyle |
| 7,125,396 B2 | 10/2006 | Leinsing et al. |
| 7,140,592 B2 | 11/2006 | Phillips |
| 7,182,313 B2 | 2/2007 | Doyle |
| 7,195,228 B2 | 3/2007 | Tiberghien et al. |
| 7,244,249 B2 | 7/2007 | Leinsing et al. |
| 7,306,197 B2 | 12/2007 | Parrino et al. |
| 7,306,198 B2 | 12/2007 | Doyle |
| 7,306,566 B2 | 12/2007 | Raybuck |
| 7,347,458 B2 | 3/2008 | Rome et al. |
| 7,350,764 B2 | 4/2008 | Raybuck |
| 7,361,164 B2 | 4/2008 | Simpson et al. |
| 7,497,484 B2 | 3/2009 | Ziman |
| 7,559,530 B2 | 7/2009 | Korogi et al. |
| 7,588,563 B2 | 9/2009 | Guala |
| 7,645,274 B2 | 1/2010 | Whitley |
| 7,651,481 B2 | 1/2010 | Raybuck |
| 7,666,170 B2 | 2/2010 | Guala |
| 7,758,566 B2 | 7/2010 | Simpson et al. |
| 7,766,304 B2 | 8/2010 | Phillips |
| 7,766,897 B2 | 8/2010 | Ramsey et al. |
| 7,803,139 B2 | 9/2010 | Fangrow, Jr. |
| 7,803,140 B2 | 9/2010 | Fangrow, Jr. |
| 7,815,614 B2 | 10/2010 | Fangrow, Jr. |
| 7,837,658 B2 | 11/2010 | Cote et al. |
| 7,857,805 B2 | 12/2010 | Raines |
| 7,976,532 B2 | 7/2011 | Kitani et al. |
| 7,998,134 B2 | 8/2011 | Fangrow et al. |
| 8,066,692 B2 | 11/2011 | Simpson et al. |
| 8,211,069 B2 | 7/2012 | Fangrow, Jr. |
| 8,262,628 B2 | 9/2012 | Fangrow, Jr. |
| 2001/0029355 A1 | 10/2001 | Szames et al. |
| 2002/0066715 A1 | 6/2002 | Niedospial, Jr. |
| 2003/0060804 A1 | 3/2003 | Vaillancourt |
| 2003/0066978 A1 | 4/2003 | Enerson |
| 2003/0111623 A1 | 6/2003 | Enerson |
| 2003/0136932 A1 | 7/2003 | Doyle |
| 2003/0208165 A1 | 11/2003 | Christensen et al. |
| 2004/0124388 A1 | 7/2004 | Kiehne |
| 2004/0124389 A1 | 7/2004 | Phillips |
| 2005/0015075 A1 | 1/2005 | Wright et al. |
| 2005/0124942 A1 | 6/2005 | Richmond |
| 2005/0212292 A1 | 9/2005 | Parrino et al. |
| 2005/0228362 A1 | 10/2005 | Vaillancourt |
| 2005/0245872 A1 | 11/2005 | Simpson et al. |
| 2006/0058734 A1 | 3/2006 | Phillips |
| 2006/0129109 A1 | 6/2006 | Shaw et al. |
| 2006/0142730 A1 | 6/2006 | Proulx et al. |
| 2006/0142735 A1 | 6/2006 | Whitley |
| 2006/0149213 A1 | 7/2006 | Raybuck |
| 2006/0157984 A1 | 7/2006 | Rome et al. |
| 2006/0161115 A1 | 7/2006 | Fangrow |
| 2006/0192164 A1 | 8/2006 | Korogi et al. |
| 2006/0202146 A1 | 9/2006 | Doyle |
| 2006/0253084 A1 | 11/2006 | Nordgren |
| 2007/0073270 A1 | 3/2007 | Christensen et al. |
| 2007/0088292 A1 | 4/2007 | Fangrow |
| 2007/0088293 A1 | 4/2007 | Fangrow |
| 2007/0088294 A1 | 4/2007 | Fangrow |
| 2007/0088324 A1 | 4/2007 | Fangrow, Jr. |
| 2007/0088327 A1 | 4/2007 | Guala |
| 2007/0179453 A1 | 8/2007 | Lim et al. |
| 2008/0103485 A1 | 5/2008 | Kruger |
| 2008/0190485 A1 | 8/2008 | Guala |
| 2008/0287920 A1 | 11/2008 | Fangrow |
| 2010/0249723 A1 | 9/2010 | Fangrow, Jr. |
| 2010/0256574 A1 | 10/2010 | Simpson et al. |
| 2011/0015581 A1 | 1/2011 | Fangrow, Jr. |
| 2011/0015582 A1 | 1/2011 | Fangrow, Jr. |
| 2011/0046572 A1 | 2/2011 | Fangrow |
| 2011/0276035 A1 | 11/2011 | Fangrow, Jr. |
| 2011/0306931 A1 | 12/2011 | Kamen et al. |
| 2012/0041391 A1 | 2/2012 | Fangrow et al. |
| 2012/0089101 A1 | 4/2012 | Carlyon et al. |
| 2012/0271244 A1 | 10/2012 | Simpson et al. |
| 2012/0330247 A1 | 12/2012 | Fangrow, Jr. |
| 2013/0150806 A1 | 6/2013 | Fangrow, Jr. |
| 2013/0231616 A1 | 9/2013 | Fangrow, Jr. |

FOREIGN PATENT DOCUMENTS

| | | |
|---|---|---|
| GB | 2 116 277 | 9/1983 |
| GB | 2 118 440 | 11/1983 |
| GB | 2 353 078 | 2/2001 |
| JP | 11-311234 | 11/1999 |
| WO | WO 01/03756 | 1/2001 |
| WO | WO 2004/060474 A1 | 7/2004 |
| WO | WO 2004/082756 | 9/2004 |
| WO | WO 2006/076656 | 7/2006 |
| WO | WO 2006/088858 | 8/2006 |
| WO | WO 2006/124756 | 11/2006 |
| WO | WO 2013/036854 | 3/2013 |

OTHER PUBLICATIONS

U.S. Appl. No. 11/417,671, filed May 3, 2006, Gustus et al.
U.S. Appl. No. 11/417,648, filed May 3, 2006, Gustus et al.
U.S. Appl. No. 11/417,909, filed May 3, 2006, Gustus et al.
U.S. Appl. No. 11/417,882, filed May 3, 2006, Gustus et al.
International Search Report and Written Opinion re PCT App. No. PCT/US2009/068857, dated (mailed) Apr. 8, 2010.
International Preliminary Report on Patentability re PCT App. No. PCT/US2009/068857, issued Jun. 21, 2011 in 8 pages.

* cited by examiner

US 8,679,090 B2

MEDICAL CONNECTOR WITH CLOSEABLE LUER CONNECTOR

PRIORITY CLAIM AND INCORPORATION BY REFERENCE

The present application claims the benefit of U.S. Provisional Patent Application No. 61/139,514, filed Dec. 19, 2008 (entitled "MEDICAL CONNECTOR WITH CLOSEABLE LUER CONNECTOR").

The present application hereby incorporates by reference the entire disclosure of U.S. Provisional Patent Application No. 61/139,514, filed Dec. 19, 2008 (entitled "MEDICAL CONNECTOR WITH CLOSEABLE LUER CONNECTOR") and U.S. Pat. No. 5,685,866, issued Nov. 11, 1997 (entitled "MEDICAL VALVE AND METHOD OF USE") as if fully set forth herein.

BACKGROUND OF THE INVENTION

1. Field of the Invention

Embodiments relate generally to medical connectors through which fluids flow, and in particular, to medical connectors with male luers.

2. Description of the Related Art

Systems of connectors, valves, and tubing are routinely used in hospitals and other medical settings for facilitating the transfer of fluids to and from patients. It is often a challenge to keep such systems sterile and to prevent leakage of fluids when the various components are engaged and disengaged. There remains a need for improved connectors that seal at their male and/or female ends.

SUMMARY OF THE INVENTION

Disclosed are various embodiments of medical connectors with closeable male luers. It is contemplated that the features of the various embodiments disclosed herein are combinable to form additional embodiments. Such combinations are within the scope of this disclosure.

In some exemplifying embodiments, a male luer connector can have a main housing with first and second ends. The first end of the housing can comprise a male luer and a shroud surrounding at least a portion of the male luer. The shroud can have screw threads disposed on an internal wall thereof. A tubular valve member with a fluid pathway can be disposed within the housing. The valve member can have a tip on its first end. In the region near the tip, one or more fluid holes can be positioned on the valve member so as to provide a fluid pathway therethrough. The tip can be configured to abut snugly against an internal wall of the male luer in a region at or near the first end of the male luer. The valve member can also have one or more struts that can be directed towards the first end. The struts can extend axially through a portion of the housing, and the ends of the struts toward the first end can be positioned within a space between the male luer and the shroud on the first end of the housing. A length of medical tubing can be connected to the connector. An end of the tubing can be attached to the second end of the valve member by adhesive, friction fit, welding, or some other means. A resilient member formed, for example, from either a metal and/or an elastomeric material can be positioned within the housing and can bias the valve member toward the closed position.

In the closed state or position, the tip of the valve member can be pressed into close contact with a portion of the internal wall on the first end of the male luer, and fluid flow from the medical tubing through the tubular valve member can be generally impeded. Fluid generally cannot escape through the opening on the first end of the male luer because such opening can be blocked by the tip of the valve member.

When a force is applied to move or displace the valve member from the housing, the resilient member can be compressed and the tip of the valve member can be displaced toward the open position. This displacing force can be applied automatically through the action of connecting the male luer to a female end of another medical implement. As the advancing end of the female connector proceeds up the screw threads on the first end of the housing of the male luer connector, the female connector makes contact with and exerts a force directed towards the second end against the struts of the valve member. This force moves the valve member towards the second end against the biasing force directed towards the first end exerted by the resilient member. In this opened state, fluid can be permitted to flow through the opposing holes, around the tip of the valve member, and out of the connector through the gap between the tip of the valve member and the internal wall on the first end of the male luer. In some embodiments, the valve member can be automatically advanced in the direction of the second end when the valve member contacts a fluid conduit (e.g., an internal conduit positioned within a female connector) as the male and female connectors are brought together.

When the separating force is removed, for example, by detaching the female connector from the first end of the housing, the resilient member once again can draw the housing and the valve member together. This causes the tip on the first end of the valve member to abut closely against a portion of the internal wall in a region near the first end of the male luer, and impedes fluid flow out of the valve.

Some embodiments provide a medical connector including a substantially rigid housing having a first end and a second end wherein the first and second ends are connected by a selectively closable fluid passageway. The first end can include a hollow male luer with an inner surface, a first open end, and a second base end. The connector can further include a first valve member supported substantially within the housing, the first valve member being configured to selectively seal an opening adjacent to the first end of the housing at the tip of the male luer when the connector is in a closed position and an internal bladder member positioned within the housing and outside the male luer, the bladder member defining an inner cavity and being fluidly coupled to the first valve member, the inner cavity of the bladder member having a first volume in the connector closed position and a second volume smaller than the first volume when the connector is in an open position.

In some embodiments, the rigid housing may extend laterally from the base of the male luer and an activation arm may extend through the housing adjacent the base of the male luer, a first end of the activation arm configured to engage a corresponding female end of a medical implement and a second end of the activation arm configured to engage at least a portion of the bladder member. In some embodiments there is a plurality of activation arms wherein the plurality of activation arms can be connected by a ring. In some embodiments, the bladder member of the connector can include a wall portion being concave toward a longitudinal axis of the connector so as to form a substantially ovular inner cavity. In some embodiments, the bladder member includes a corrugated wall portion. In some embodiments, at least a portion of the bladder member and at least a portion of the valve member are integrally formed.

In some embodiments, the connector includes an annular ring between the valve member and the inner surface of the male luer. The annular ring can be integrally formed with the valve member and can remain in sliding engagement with the inner surface of the male luer between both the closed and open positions of the connector. Alternatively, the inner surface of the male luer can include an annular channel and the annular ring can be recessed into said annular channel and can be in sliding engagement with the outer surface of the valve member.

In some embodiments, the second end can have a female connector portion having an opening axially therethrough. An internal bladder member can be positioned within the housing so that it is outside of the female connector portion so as to be between an end wall of the housing adjacent to the female connector portion and between a valve member positioned within a male luer connector portion of the medical connector. The bladder member can define an inner cavity and can be fluidly coupled to the valve member and the female connector portion. The inner cavity of the bladder member can have a first volume in the connector closed position and a second volume smaller than the first volume when the connector is in an open position.

A protrusion can project from the female portion (e.g., the end wall of the housing) and can be configured to extend into an opening formed in the bladder member. The protrusion can have an annular recess thereon configured to receive the annular wall forming the perimeter of the opening of the bladder member. The opening in the bladder member and the protrusion can be configured to form a generally liquid or gas tight seal between the protrusion and the bladder member so that the bladder member can be sealably supported by the protrusion and, hence, the end wall of the housing.

Similarly, a protrusion can project from the valve base and can be configured to extend into a second opening formed in the bladder member. The protrusion can have an annular recess thereon configured to receive the annular wall forming the perimeter of the second opening of the bladder member. The second opening in the bladder member and the protrusion can be configured to form a generally liquid or gas tight seal between the protrusion and the bladder member so that the bladder member can be sealably supported by the protrusion and, hence, the valve base. In some embodiments, one or more activation arms can be supported by the valve base. The activation arms can be integrally formed with the valve base or otherwise attached to or supported by the valve base.

Some embodiments provide a closeable male luer having a rigid housing, a valve member supported within the housing, and a first end portion. The first end portion can be, inter alia, a male luer tip. The valve member can extend into an opening formed in the first end portion and move between a first or closed position (wherein liquid is substantially prevented from flowing through the valve member and tip) and a second or open position (wherein liquid is permitted to flow through the valve member and tip). The valve member can be configured to be moveable between a first and a second position by imparting a force directly on a portion of the valve member, such as without limitation, a tube member projection from a valve base.

In some embodiments, the closeable male luer can further comprise, without limitation, struts or activation arms projecting from a valve base of the valve member toward a first end of the medical connector. The struts can be configured such that an axial force imparted on the valve struts can be transferred to the valve base so as to displace the valve member. The struts can be configured to engage a proximal end of a female connector engaged with the closeable male luer as the female connector threadably or otherwise advances into engagement with the closeable male luer. A valve tube can be supported by or attached to the valve base, and can project from the valve base such that, in the assembled configuration, the valve tube extends into an opening formed in the male luer tip.

In some embodiments, a diaphragm member formed from a generally liquid impermeable resilient material can be supported within the housing. The diaphragm member can have a generally planar shape or a pair of generally parallel, planar surfaces. The diaphragm member can also have, but is not required to have, a generally annular, disc-like shape. The diaphragm member can be positioned such that an outer periphery of the diaphragm member is sealably supported by the housing. An annular recess can be formed in the housing to support the outer periphery of the diaphragm member. Alternatively, the outer periphery of the diaphragm member can be positioned between a portion of each of two housing portions. An opening can be formed in the diaphragm member, the opening configured to receive an aft portion of the valve base so that the diaphragm member can be sealably secured to the valve member. In some embodiments, a projection extending from the valve base can be received within the opening in the diaphragm member. The projection can define a recess configured to receive and support the opening formed in the diaphragm member.

The diaphragm member can be positioned so as to exert a force on the valve member that biases the valve member toward the closed position. For example, without limitation, the diaphragm member can bias the tube member projecting from the valve base to sealably close against the inside surface of the luer tip. In some embodiments, the diaphragm member can be positioned within the luer connector so that, when the valve member is in the closed position, the diaphragm is partially deflected from its relaxed state so as to increase the bias force that the diaphragm exerts on the valve member.

The diaphragm member can form a partition within the housing so as to create a substantially fluid sealed cavity or chamber within the housing. The diaphragm member can be configured so that the volume within the cavity when the valve member is in the closed position is greater than volume within the cavity when the valve member is in the open position. In this configuration, the volume of space within the cavity can increase when the valve member moves from the open position to the closed position, thereby creating a force of suction that can reduce the amount of fluid or medicament that can flow through or drip out of an opening in the male luer tip as the valve member closes, by drawing such fluid back toward the cavity.

In some embodiments, the valve member can be configured such that the valve struts are directly attached to either the tube or the valve base so that an axial force imparted on the valve struts that causes the valve struts to displace also causes at least a portion of the diaphragm member to displace in addition to causing the tube and/or the valve base to displace. In some embodiments, the valve struts can be separate from the valve base or the tube so as to move independently compared to the valve base or the tube. In this configuration, the struts can each can exert an axial force on at least a portion of the diaphragm when the struts are displaced due to the engagement of a female connector with the first end portion of the housing, thereby deflecting the diaphragm. As the diaphragm is deflected, the valve member can be moved toward the open position because the diaphragm can be secured to the valve base.

In some embodiments, the bladder member can have a generally cylindrical or tubular shape, and can be positioned within the housing so that the opening axially through the bladder member is generally coaxially aligned with an opening formed in a female connector portion of the housing and an opening formed in the male luer tip. The bladder member can have one end surface that can be sealably supported by or positioned against an end wall surface adjacent to the female connector portion of the housing. Similarly, a second end surface of the bladder member can be sealably supported by or positioned against a valve base of the valve member so as to define a chamber or cavity bounded generally by the tubular wall of the bladder member, the end wall of the housing, and the valve member. An opening formed through the end wall of the housing and an opening formed in the valve member can be in communication with the chamber. The volume within the chamber when the luer connector is in the closed position can be larger than the volume within the chamber when the luer connector is in the open position. The increase in the volume of the chamber as the valve member moves from the open to the closed position can create a reduced pressure that draws the fluid from the luer tip or tube back into or toward the chamber.

Some embodiments provide a method for selectively closing a medical connector, the method comprising supporting a resilient bladder member within a housing, moving a valve member at least partially supported within the housing between a connector open position and a connector closed position such that, in the closed position, the valve member substantially prevents liquid from flowing through the fluid passageway and, in the open position, the valve member permits liquid to pass through the fluid passageway, and moving the bladder member between a first configuration having a first volume in the connector closed position and a second configuration having a second volume in the connector open position. The second volume can be, but is not required to be, smaller than the first volume.

The housing can have a first end and a second end, said first and second ends being connected by a selectively closable fluid passageway and said first end having a hollow male luer with an inner surface. In some embodiments, the bladder member can have a corrugated wall portion. In some embodiments, the bladder member can have an opening therethrough and an internal chamber in communication with the fluid passageway. Further, the bladder member can be, but is not required to be, supported within the housing so as to be outside the male luer.

Some embodiments provide the method described above, wherein moving the valve member between the connector open position and the connector closed position and moving the bladder member between the first configuration and the second configuration can comprise engaging or disengaging the medical connector with or from a corresponding female end of a medical implement. In some embodiments, moving the bladder member between the first configuration and the second configuration can comprise moving at least one activation arm between a first and a second position, the at least one activation arm being configured to engage a corresponding female end of a medical implement and having a second end thereof configured to engage at least a portion of the bladder member. Moving the at least one activation arm between the first and the second position can comprise engaging or disengaging the medical connector with or from a corresponding female end of a medical implement.

Also disclosed herein are other features and configurations for the foregoing embodiment, as well as additional embodiments for other connectors with closeable male luers. Such embodiments generally include means for permitting or impeding fluid flow through a male luer on a connector, which can be automatically opened upon connection with a corresponding female connector. Such embodiments also include features and configurations that permit the female portion of the male luer connector to be coupled with a corresponding male luer portion of a male luer connector or other component such as a syringe.

BRIEF DESCRIPTION OF THE DRAWINGS

Some embodiments will now be discussed in detail with reference to the following figures. These figures are provided for illustrative purposes only, and the embodiments are not limited to the subject matter illustrated in the figures.

DETAILED DESCRIPTION OF THE PREFERRED EMBODIMENTS

In some embodiments, the male luer includes closing mechanisms which function to prevent and/or impede fluid from escaping from or entering into the male luer, while allowing fluid flow when the male luer is manually opened or engaged with a corresponding female luer. As used herein, terms such as "closed" or "sealed" should be understood as obstructions or barriers to fluid flow. These terms should not be understood to require that a particular structure or configuration achieves a complete fluid closure in all circumstances.

Some medications, including those used during chemotherapy, can be harmful to a patient in certain applications. For example, exposure to the skin can sometimes result in a chemical burn. Inhalation of aerosolized forms of some medications also can be harmful. Thus, control over the containment of the medication is highly desirable.

At present, some potentially harmful medications are distributed in sealed vials. The medication can be removed from the vial by inserting a needle and drawing the medication into a syringe. The needle can be then withdrawn from the vial and the medication can be dispensed. However, when the needle is inserted into the medication for drawing into the syringe, the needle may be withdrawn with a residue of medication disposed on the outside of the needle. This medication can inadvertently come in contact with the skin and cause harm. Or, if a vial adapter is used to penetrate the vial with a withdrawal mechanism, the medication can be drawn through the mechanism and passed directly to a syringe for injection without the additional step of withdrawing the mechanism from the vial. However, even if such a vial adapter is used, there is still the possibility of latent medication remaining on the end of the syringe used to inject the medication, on the mechanism after the vial is decoupled, or on the mechanism after the syringe is decoupled.

Figure 1A:
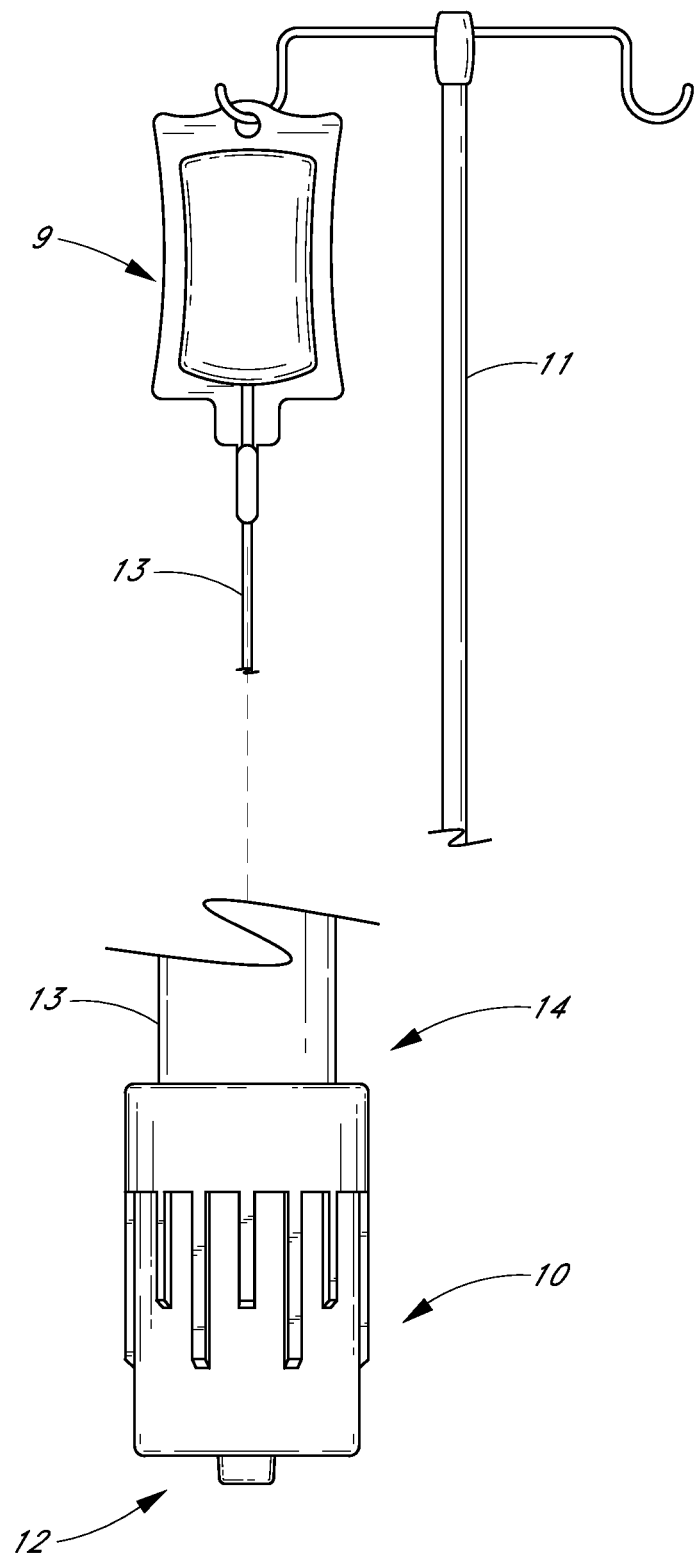
FIG. 1A is a perspective view of an embodiment of a male luer connector attached to tubing configured to receive fluid from a hanging gravity-fed IV bag. In this and other figures, the relative size of the connector and attached tubing is increased in comparison to other objects to facilitate viewing certain details.

FIG. 1A is a perspective view of an embodiment of a male luer connector in an example of use in which it is attached to tubing configured to receive fluid from a hanging gravity-fed IV bag. In FIG. 1A, an embodiment of a closeable male luer connector 10 is shown in a closed position. The luer connector 10 can be attached to a gravity-fed IV bag 9 filled with fluid hanging from a pole stand 11. At the bottom of the bag 9, a section of tubing 13 can be attached. The opposite end of the tubing 13 can be connected to the second or distal end 14 of the luer connector 10. A closing mechanism on the interior of the first or proximal end 12 of the luer connector 10 can prevent the fluid contained within the bag 9 from flowing through the tubing 13 and leaking out of the luer connector 10, as long as the luer connector 10 remains in a closed configuration.

The IV delivery system illustrated in FIG. 1A can be easily readied for fluid communication with a patient. In most circumstances, the tubing 13 is filled with air when it is initially connected to the IV bag 9. If the other end of the tubing 13 can be connected to a closed connector, as illustrated in FIG. 1A, the air cannot escape and fluid cannot enter the tubing 13 from the IV bag 9. In some embodiments, the luer connector 10 can be manipulated so as to be in the open position until all of the air has been purged through the luer 10 and the fluid in the IV bag 9 fills the tubing 13 and connector 10. This procedure is known as "priming." As soon as the fluid line and connector are properly primed, the health care provider can then manipulate the luer connector 10 to the closed position to stop the flow of fluid through the luer connector 10.

Figure 1B:
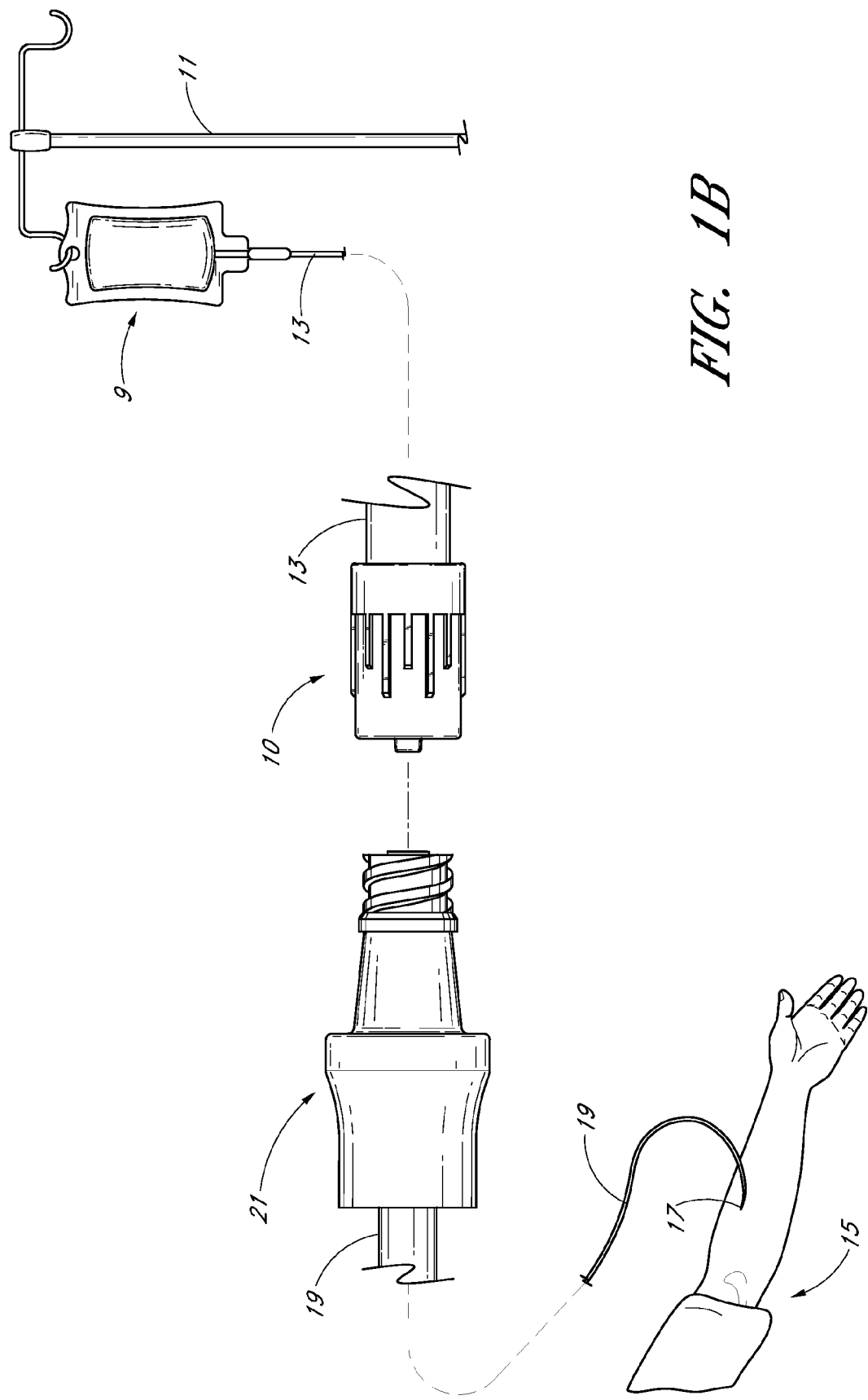
FIG. 1B shows a perspective view of an embodiment of the male luer connector of FIG. 1A being connected to an example of a female connector attached to tubing inserted into a patient.

FIG. 1B shows a perspective view of an embodiment of the male luer connector of FIG. 1A being connected to an example of a female connector attached to tubing inserted into a patient. Referring now to FIG. 1B, a catheter 17 has been inserted into a patient's arm 15. The catheter 17 penetrates the skin of the arm 15 and can be fluidly connected with the patient's bloodstream. The catheter 17 can also be connected to a length of medical tubing 19 attached to a female medical connector 21. The example of a female medical connector 21 illustrated in FIG. 1B is a version of the Clave® connector manufactured by ICU Medical, Inc., San Clemente, Calif. Various embodiments of a connector of this type are illustrated and described in U.S. Pat. No. 5,685,866, which is incorporated by reference herein its entirety. It is contemplated that many of the male luer embodiments disclosed herein can be used with other types of female connectors. The tubing 19, catheter 17, and female connector 21 were preferably previously primed with fluid using standard procedures. The luer connector 10 can be primed as described previously and brought into engagement with the female connector 21. As described in further detail below, when the male connector 10 and female connector 21 are engaged, fluid can be permitted to flow from the IV bag 9 into the patient. When the male connector 10 and female connector 21 are disengaged, fluid can be once again prevented from flowing out of the first end 12 of the male connector 10. In general, fluid can also be prevented from flowing out of the opening in the female connector 21.

The embodiment illustrated in FIGS. 1A-1B is described in further detail below. Each of the other embodiments disclosed herein can be used in the illustrated fluid system, and in various modifications and alternatives thereof. Further, it is contemplated that the various embodiments of connectors can be used in a wide variety of additional medical fluid systems. For example, the disclosed connectors can also be used to transfer bodily fluids such as blood, urine, or insulin, nourishing fluids, and/or therapeutic fluids such as fluids used in chemotherapy treatments. The disclosed connectors can also be used to interconnect various other components of fluid transfer systems.

Figure 2A:
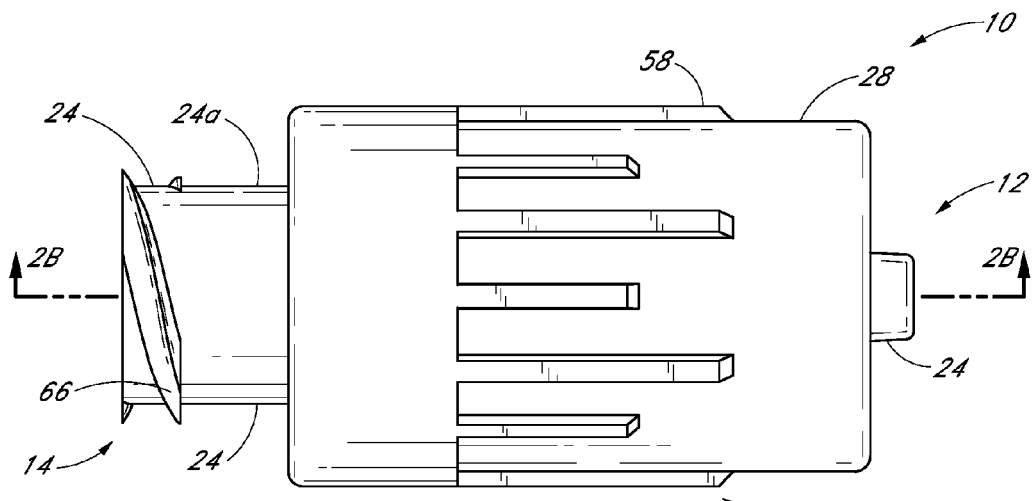
FIG. 2A is a side view of the outside of the embodiment of the luer connector shown in FIG. 1A.
Figure 2B:
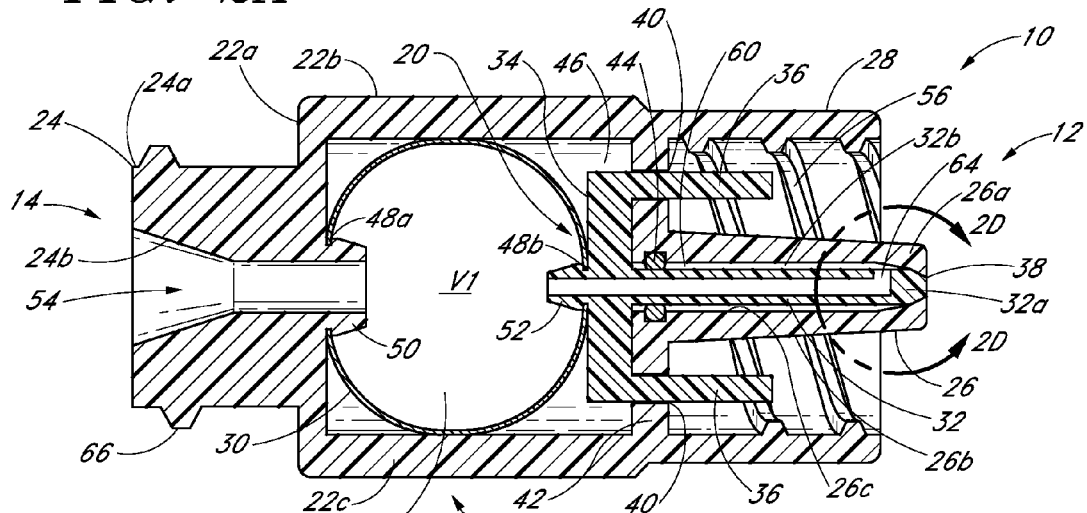
FIG. 2B is a cross-sectional view of the embodiment of the luer connector shown in FIG. 1A in a closed position.
Figure 2C:
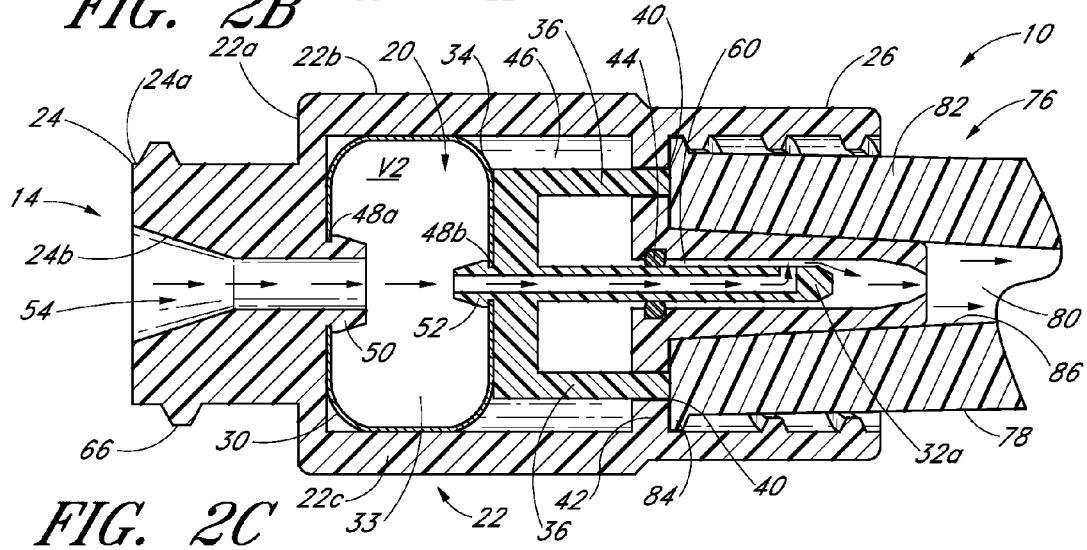
FIG. 2C is a cross-sectional view of the embodiment of the luer connector shown in FIG. 1A in an open position.

Referring now to FIGS. 2A-2C, an embodiment of the closeable male luer 10 of FIGS. 1A-1B is illustrated in greater detail. FIG. 2A is a side view of the outside of the luer connector 10. FIG. 2B is a cross-sectional view of the luer connector 10 in a closed position so that fluid is generally prevented from flowing through the luer connector 10. When the luer connector 10 is in the closed position, fluid can be significantly prevented by the valve member 20 from flowing through the luer connector 10. In general, the valve member 20 can be configured to prevent fluid under system pressures from flowing through the connector 20. FIG. 2B is a cross-sectional view of the luer connector 10, showing the valve member 20 in an open position. In the open position, the valve member 20 can be positioned so as to not significantly impede the flow of fluid through the luer connector 10.

As illustrated in FIG. 2A, some embodiments of the assembled luer connector 10 can comprise a housing 22, a port 24 positioned near the second end 14 of the luer connector 10, a luer tip 26 positioned near the first end 12 of the luer connector 10, a shroud 28 surrounding at least a portion of the luer tip 26, a diaphragm 30 supported within the housing 22, and the valve member 20 mentioned above also supported within the housing 22. In some embodiments, the diaphragm 30 can be formed from a generally fluid impervious, suitably resilient material and may be separately or integrally formed with the valve member 20. The diaphragm 30 can generally define an internal cavity 33.

In the illustrated embodiment, the valve member 20 can comprise a tube 32 projecting from a valve base 34 toward the first end 12 of the connector 10, and one or more valve arms or struts 36 can also project from and be supported by the valve base 34. In some embodiments, in an assembled configuration, the valve struts 36 can be positioned so as to be adjacent to the tip 26 along the sides of the tip 26. When the luer connector 10 is in the closed position, the outer surface of at least the distal portion 32a of the valve tube 32 can be sealingly closed against the inner surface of at least the distal portion 26a of the luer tip 26 such that fluid is generally prevented from flowing through the opening 38 formed in the distal end 26a of the luer tip 26.

Generally, luer tip 26 corresponds to ANSI standards for medical connectors to facilitate use with various standard medical implements. In some embodiments, the diameters of the opening 38 in the distal tip portion 26a of the luer tip 26 can be in the ranges of approximately 0.4 mm to approximately 1.8 mm, approximately 0.5 mm to approximately 1.5 mm, and approximately 0.5 to approximately 1.0 mm. Other diameters, either inside or outside the listed ranges can also be used. Additionally, as described above, the second end of the valve member 20 can be sized appropriately to occupy the space in the opening 38 of the distal end portion 26a of the luer tip 26.

In the illustrated embodiment, the tube 32 can be slidable so as to translate axially within the luer tip 26. Further, the valve struts 36 can be supported in a cantilevered disposition by the valve base 34 and can be configured so as to slide within the openings 40 formed through the internal wall 42 of the housing 22. The number of openings 40 through the internal wall 42 can be equal to the number of the valve struts 36 supported by the valve base 34. An annular sealing member 44 can be positioned between the outside surface of the valve tube 32 and the inside surface of the luer tip 26 so as to prevent any fluid from flowing into the chamber 46. In the illustrated embodiment, the chamber 46 is the space outside the internal cavity 33 generally defined by diaphragm 30 that is generally confined by the end wall 22a of the housing 22, the sidewall 22b (which can be cylindrically shaped) of the housing 22, and the internal wall 42 formed on the housing 22.

In the illustrated embodiment, the diaphragm 30 can be supported near the second end 14 of the luer connector 10 by the end wall 22a of the housing 22, laterally by the sidewall 22b (which can be cylindrically shaped) of the housing 22, and by the valve member 20. In the illustrated embodiment, the diaphragm 30 can comprise a pair of generally opposing openings 48a, 48b, through which fluid can pass. The first opening 48a formed in the diaphragm 30 can be sealably supported by a protrusion 50 formed on the end wall 22a of the housing 22. The second opening 48b formed in the diaphragm 30 can be sealably supported by a protrusion 52 formed on the valve base 34. The first and second openings 48a, 48b can be supported by the protrusions 50, 52 so that fluid can be generally prevented from leaking into the chamber 46.

In some embodiments, the diaphragm 30 can be resilient and biased toward an expanded position, as illustrated in FIG. 2B, so as to exert a force on the valve member 20 that biases the valve member 20 toward the closed position. Further, the diaphragm 30 can be configured so that the volume of the cavity 33 within the diaphragm 30 when the valve member 20 is in the closed position (which is represented by V1 in FIG. 2B) can be greater than the volume of the cavity 33 within the diaphragm 30 when the valve member 20 is in the open position (which is represented by V2 in FIG. 2C). Thus, the volume of the cavity 33 within the diaphragm 30 can decrease when the valve member 20 moves from the closed position to the open position and can increase when the valve member 20 moves from the open position to the closed position. By increasing the volume of the cavity 33 within the diaphragm 30 as the valve member 20 moves to the closed position, the diaphragm 30 can create a force of suction that reduces the amount of fluid or medicament that can flow through or drip out of the opening 38 as the valve member 20 is in the process of closing, by drawing such fluid back towards the diaphragm 30.

In some embodiments, the valve 20, the valve base 34, the valve struts 36, and the protrusion 52 can be integrally formed. In some embodiments, any of the features of the valve member 20, including the valve tube 32, the valve base 34, the valve struts 36, and the protrusion 52, can be separately formed and adhered or otherwise joined together in subsequent manufacturing steps. In some embodiments, the end wall 22a can be formed integrally with at least the sidewalls 22b of the housing 22. In some embodiments, the end wall 22a can be formed separately as compared to at least the sidewalls 22b and joined or adhered to the housing 22 in a subsequent manufacturing step, preferably after other components such as the valve member 20, the diaphragm 30, and the seals are properly positioned within the housing.

In some embodiments, the housing 22 can generally be a tube-like structure with a passageway 54 that can extend from the second end 14 of the connector 10 and preferably through the axial center of the luer connector 10. As a result, in some embodiments, when the luer connector 10 is in the open state or position, as illustrated in FIG. 2C, the passageway 54 can permit fluid to flow from the second end 14 through the port 24, the diaphragm 30, the tube 32, and out through the opening 38 in the luer tip 26 positioned at the first end 12 of the luer connector 10. Near the second end 14 of the luer connector 10, the port 24 and the corresponding section of the fluid passageway 54 can be sized and configured so as to accommodate a section of standard-diameter medical tubing inserted therein. In some embodiments, the port 24 is configured to accept a standard male luer corresponding to ANSI standards for medical valves.

In some embodiments, the length of the housing 22 (or any housing described herein) from the second end 14 to the distal end of the luer tip 26 can be approximately 0.75 inch. However, the housing 22 can have many other sizes. In some embodiments, the length of the housing 22 (or any housing described herein) from the second end 14 to the distal end of the luer tip 26 can be from approximately 0.5 inch to approximately 0.75 inch, or from approximately 0.75 inch to approximately 1.0 inch, or from approximately 1.0 inch to approximately 1.25 inches or more, or from or to any value within these ranges. Thus, the housing 22 can be less than or equal to approximately 1.50 inches from the second end 14 to the distal end of the luer tip 26 so that the weight and bulk of the connector can be minimized. However, the housing 22 can have any suitable length for a particular application.

The shroud 28 can have inner threads 56 on an interior wall that help securely attach the connector 10 in a removable fashion to another medical implement. In other embodiments, the shroud 28 can include other structures or materials for providing a releasable connection, including quick-release mechanisms and other means. As illustrated, the housing 22 and shroud 28 can define a plurality of protrusions 58 or other suitable features on an outer surface to assist the user in firmly grasping and twisting the shroud 28 and the housing 22 with the user's fingers so as to prevent the luer connector 10 from slipping within the user's grasp when the luer connector 10 is twisted. In other embodiments (not illustrated) the housing 22 or shroud 28 may alternatively or additionally define depressions that have upwardly tapering sidewalls that provide additional support to help prevent the fingers from sliding off the connector 10, or any other features or materials that substantially prevent the fingers from sliding relative to the connector 10. The protrusions 58 may extend around substantially the entire outer surface of the housing 20 or shroud 28 so that the user's fingers, when positioned on opposite sides of the connector 10, will likely encounter a depression, regardless of the orientation of the connector 10, during use.

With reference to FIGS. 2A-2C, the tip 26 can have a tapered external wall. The diameter of the tip 26 can become gradually smaller from the valve base 34 towards the distal end portion 26a of the tip 26. As described above, the tip 26 can define an opening 38 positioned at the distal end portion 26a of the luer tip 26. At the base of the luer tip 26, which can be the internal wall 42, an interior space 60 (see FIG. 2B) communicates with the fluid passageway 54 of the luer connector 10 and with the opening 38 so as to provide a fluid flow path through the entire luer connector 10. In some embodiments, the term fluid passageway can refer to the entire fluid pathway through the luer connector. With regard to any of the luer connectors described herein, the dimensions of the luer tip and the end cap (i.e., the male and female ends) can be made to comply with applicable standards and/or regulations, such as the ANSI standards.

Figure 2D:
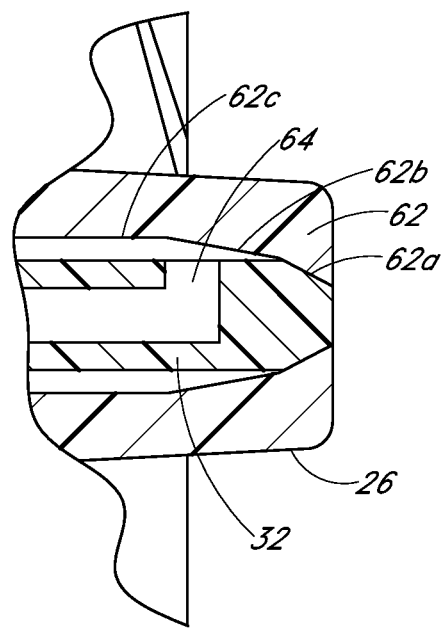
FIG. 2D is an enlarged section view of a portion of the embodiment of the luer connector shown in FIG. 2C, defined by the curve 2D-2D in FIG. 2B.

FIG. 2D is an enlarged section view of a portion of the luer connector 10, defined by the curve 2D-2D in FIG. 2B. As shown in FIG. 2D, the interior wall of the luer tip 26 can include a constricted portion 62 that extends radially inwardly toward the axis of the fluid passageway 54 surrounded by the luer tip 26, making the fluid passageway 54 narrower at the distal end portion 26a of the luer tip 26 than in the region adjacent to the constricted portion 62. In the illustrated embodiment, the constricted portion 62 can define a generally cylindrically shaped surface 62a and a generally sloped or tapered surface 62b. In some embodiments, as in the illustrated embodiment, the constricted portion 62 can further define a second sloped or tapered surface 62c that can be configured to match a similarly sloped or tapered surface on the distal end portion 32a of the tube 32.

As illustrated in FIG. 2D, in some embodiments, the distal end portion 32a of the tube 32 can be sized and configured so as to complement the size and shape of the constricted portion 62 of the luer tip 26 so as to define a sealable closing mechanism. The closing mechanism can be adapted to close the fluid passage extending through the closeable male luer 10 from fluid communication with the external environment, such as when the male luer 10 is not engaged with a female connector. In particular, in some embodiments the distal end portion 32a of the tube 32 can be sized and configured so as to complement the generally cylindrically shaped, sloped surface 62a. In some embodiments, the tube 32 can be further configured to complement the generally sloped surface 62b and the second sloped surface 62c of the constricted portion 62. The inner diameter of the constricted portion 62 can become narrower so as to generally block and/or impede fluid flow through the connector 10 when the distal end portion 32a of the tube 32 is abutted against it. Thus, as the distal end portion 32a of the tube 32 abuts against the inside surface of the luer tip 26, a closure can be formed at or near the first end 12 of the male luer 10. Further, the distal end portion 32a of the tube 32 can be made from, or covered by, a different material than is used to form the tube 32. For example, in some embodiments, the distal end portion 32a can be covered with a softer, more malleable or deformable material as compared to the material used to form the tube 32 so as to provide better sealing properties between the distal end portion 32a of the tube 32 and the luer tip 26.

Any of the luer connectors described herein may be configured to comprise the features of the constricted portion 62 described above. Finally, the opening 64 in the distal end portion that can be in fluid communication with the passageway 54 can be of any suitable size or shape to improve manufacturability or to most effectively channel the fluid through the luer connector 10 when the valve member 20 is in the open position. For example, the holes 52 can be formed with a tear-drop shape (e.g., narrow on one end and wider on an opposite end), which may facilitate an injection molding process of manufacture. Further, in some embodiments, the valve member 20 can be constructed without a fluid path and function as a blocking plunger for fluid flowing around the valve member 20 rather than as a means for conveying fluid between the first and second ends of the luer connector 10.

In some embodiments, the housing 22 can be formed in two halves that each define a planar joining surface, such as, but not limited to, a surface 22c that defines the planar section surface in FIG. 2B. In this configuration, the end portion 22a of the housing 22 can be formed in a separate step as compared to the rest of the housing, and subsequently adhered to or otherwise joined to the housing after the two halves described above are adhered or otherwise joined together.

The housing 22 of the illustrated embodiment, or the housing of any embodiment described herein, can be constructed from any of a number of different materials or combination of materials. In some embodiments, the housing 22 or any housing described herein can be constructed from a relatively rigid material, such as polycarbonate or other polymeric material. The housing 22 and/or valve member 20 of this embodiment, or the housing and/or the valve member of any embodiment described herein, or any of the components of this or any other embodiment, can also be constructed of a medical grade, hydrophobic material, such as Bayer Makrolon, or any other suitable material.

In some embodiments, the diaphragm 30 can comprise a resilient material such that the diaphragm 30 can be compressed into an open position and resiliently return to its original closed position, as described above. In some embodiments, the diaphragm 30 may be formed from a non-rubber silicone or other suitable material depending at least on the medicament or fluid to be passed through the luer connector 10. Further, in some embodiments, the diaphragm 30 can be generally fluid impermeable so as to generally prevent any fluid from permeating therethrough into the chamber 46. The valve member 20 or any valve member disclosed herein, like the housing 22, may be constructed from a number of different materials or combinations of different materials, including the material that is used to form the housing 22. Examples of such materials include polycarbonate or other polymeric materials. In certain applications, for example, semi-rigid or even more flexible materials may be desirable for use in the valve member 20, and more particularly for the distal end portion 32a of the tube 32.

The length of the valve member 20 can be shorter than the length of the housing 22. Any of the valve assemblies described herein, including but not limited to the valve member 20, may be manufactured through injection molding. Finally, although the valve member 20 of the illustrated embodiment can be configured as shown in FIGS. 2B-2C, many other configurations are possible.

In some embodiments, as in the embodiments illustrated in FIGS. 2A-2C, one or more protrusions or raised tabs 66 (such as, but not limited to, threads) can be formed on an exterior surface 24a of the port 24 to facilitate removably attaching a medical implement (not shown) with the second end 14 of the valve member 20. Accordingly, in some embodiments, the exterior surface 24a can be cylindrical except for the protrusions, raised tabs, or other features formed thereon. In some embodiments, the interior surface 24b of the port 24 can be conically shaped, such that the diameter of the interior surface 24b can be greatest at the portion of the interior surface 24b adjacent to the second end 14 of the luer connector 10. The internal taper of the interior surface 24b can compliment and closely fit with the taper of a typical male luer. Such an internal taper can conform to ANSI standards and/or regulations, such as the standard for medical syringes.

Similarly, the outside surface 26b of the luer tip 26 can also be tapered to conform to ANSI standards and/or regulations, such as the standard for medical syringes. In some embodiments, the inside surface 26c of the luer tip 26 and the outside surface 32b of the tube 32 can either be straight or can also be tapered. Tapering the inside surface 26c of the luer tip 26 and the outside surface 32b of the tube 32 can help minimize the amount of fluid that flows into and is trapped in the interior space 60 between the tube 32 in the luer tip 26, since the distance between the tapered inside surface 26c of the luer tip 26 and the outside surface 32b of the tube 32 would be reduced as the tube 32 moves toward a closed position. In these configurations, the sealing member 44 can be configured so as to provide an effective seal between the tube 32 and the luer tip 26 even when the distance of the gap therebetween increases.

As shown in FIGS. 2A-2D, the closeable luer connector 10 can have a female mating end at the second end 14 of the luer connector 10 and a male luer mating end at the first end 12 of the luer connector 10. The closeable female connector 21 of FIG. 1B (referenced above), as well as other standard female connectors with similar external structure, can also have both female and male ends. In many embodiments, such female connectors can utilize seals or other fluid barriers to impede the flow of fluid on the female end but do not typically do so on the male end. In many of the embodiments of the closeable male luer connectors illustrated and described herein, there may be no seal or other fluid barrier shown on the female end. However, the female end of any of the closeable male luer connectors disclosed herein can be configured to include a closeable female end. For example, the structure for selective fluid-impedance with the female connector 21, or any of the other standard female connectors, could be included within the female end of any of the closeable male luer connectors disclosed herein to provide a connector that selectively seals or impedes fluid flow on both ends. In some embodiments of this type with closeable female and male ends, it can be advantageous for a resilient seal element to be positioned at or near the female opening, as shown in U.S. Pat. No. 5,685,866 entitled Medical Valve and Method of Use, filed on Nov. 4, 1994, which disclosure is hereby incorporated by reference in its entirety. By positioning the seal element in this manner, it is possible to cleanse the female opening prior to use with antiseptic with a wiping motion to avoid a harmful accumulation of debris, bacteria, antiseptic, or other unwanted substances on the seal element and/or in the region between the seal element and the housing of the connector adjacent to the seal element.

Figure 3:
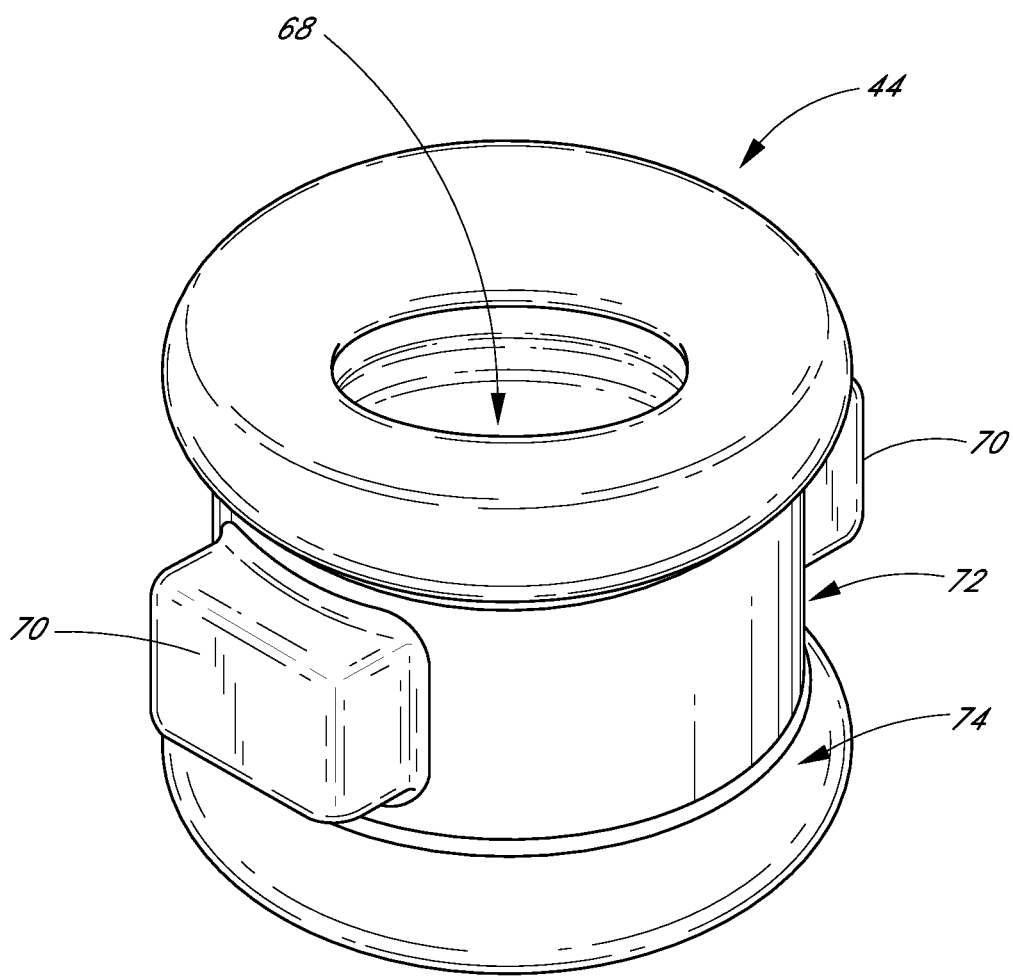
FIG. 3 is an enlarged perspective view of an embodiment of a sealing member.

With reference again to FIGS. 2B and 2C, the sealing member 44 will now be described in greater detail. In some embodiments, the sealing member 44 can define an annular cross-section, as illustrated in FIGS. 2B and 2C. In addition, in some embodiments, the luer connector 10 can be configured such that an alternative sealing member 44' can be used in place of the annular sealing member described above. FIG. 3 is an enlarged perspective view of an alternative sealing member 44'. With reference to FIG. 3, the sealing member 44' can be substantially cylindrical and can have a bore 68 extending axially through the center thereof. In some embodiments, the sealing member 44' can further comprise a pair of generally rectangular protrusions 70 extending from the sidewalls of the cylindrical portion at diametrically opposed positions. In other embodiments, the protrusions 70 can have different shapes and/or positions, and can assist with positioning and/or aligning the sealing member 44' in the desired position. In some embodiments, the sealing member 44' can also have a generally smaller-diameter middle portion 72 surrounded by two rings 74 at either end with larger diameters. The sealing member 44 or 44' can be constructed from a number of different materials. In some embodiments, the sealing member 44 or 44' can be made from a silicon-based deformable material. Silicon-based deformable materials are among those that can form fluid-tight closures with plastics and other rigid polymeric materials.

Thus, as shown in FIG. 2B, the housing 22, the valve member 20, and the sealing member 44 are in an assembled configuration, in which the closing mechanism forms a closing engagement between the distal portion 32a of the tube 32 and the interior of the luer tip 26. In addition, the sealing member 44 can be in closing engagement between the valve member 20 and the interior surface 26c of the luer tip 26. In this configuration, in the closed position, fluid flowing through the passageway 54 may be able to flow through the opening 64 adjacent to the distal portion 32a of the tube 32. In this position, the opening 64 can communicate with the interior space 60, but not with the external environment. As discussed above, it may be advantageous to configure the external surface of tube 32 and the internal surface of 26 to minimize the space 60.

FIG. 2C is a cross-sectional view of the luer connector 10 in an open position, so that fluid can be generally permitted to flow through the luer connector 10. The flow of fluid through the luer connector 10 is represented by arrows in FIG. 2C. The housing 22, the valve member 20, and the sealing member 44 are illustrated in an assembled configuration. As shown, the valve member 20 has been moved to the open position by the insertion of the female connector 76. Thus, FIG. 2C illustrates a cross-section of an embodiment of the luer connector 10 wherein the valve member 20 has been caused to be opened by the insertion of an exemplifying female connector 76. With reference to the embodiment illustrated in FIG. 2C, the structure of an exemplifying female connector 76 will now be discussed in further detail. The female connector 76 can comprise an elongate body 78 having a fluid passageway 80 therethrough, and the female connector 76 can have a tip 82 near its distal end. In some embodiments, the tip 82 of the female connector 76 can have a radially extending surface 84 disposed on its external surface. The female connector 76 can have a fluid conduit within the female connector 76. The fluid conduit is not included or required in all female connectors compatible with the connectors 10 disclosed herein. Along a proximal inner surface 86 of the female connector 76, the fluid passageway 80 can be tapered such that the diameter of the fluid passageway 80 decreases in the distal direction.

As shown in FIG. 2B and discussed above, the struts 36 of the valve member 20 can extend through openings 40 in the internal wall 42 of the housing 22 such that, in the closed position, the ends of the struts 36 extend past the internal wall 42 toward the first end 12 of the connector 10. The struts 36 can be configured to engage the proximal end 84 of the female connector 76 as the female connector 76 advances into engagement with the closeable male luer 10. To engage the male luer 10 and female connector 76, as is shown in FIG. 2C, the radially extending surface or surfaces 84 of the female connector 76 can be threaded into the inner threads 56 of the male luer 10. As shown in FIG. 2C, the two luers 10, 76 can be threadedly engaged with one another until the taper of the inner surface 86 of the female luer connector 76 lies adjacent the correspondingly tapered external surface 26b of the tip 26.

As the male luer connector 10 and female connector 76 move towards each other into threaded engagement, the proximal end 84 of the tip of the female connector 76 can contact the struts 36 of the valve member 20. As the male luer connector 10 and female connector 76 move further into threaded engagement, the struts 36, and thereby the valve member 20, can be moved toward the second end 14 of the male connector 10 by the female connector 76. Thus, the distal end portion 32a can move away from the interior distal end portion 26a of the tip 26 in the direction of the second end 14 of the male connector 10 as the male luer connector 10 and female connector 76 move further into threaded engagement. As the tip 26 and the tube 32 move apart from one another, a space or gap can form between the tube 32 and the luer tip 26, permitting fluid to pass through the opening 38 into the fluid passageway 80 of the female connector 76, or vice versa.

When used with certain alternative embodiments of the female connector 76, an internal fluid conduit of the female connector 76 may contact the distal end portion 32a of the tube 32 before the housing of the female connector 76 contacts the struts 36, thereby opening the male connector 10. In some embodiments, the closure may remain intact until the inner surface 86 of the tip of the female connector 76 has formed a closing engagement with the outer surface of the tip 26 of the male luer 10, substantially limiting fluid within the passageway 54 of the male luer 10 from being exposed to the external environment.

In some embodiments, as the valve member 20 moves relative to the housing 22, the resilient diaphragm 30 can compress, causing the diaphragm 30 to exert a biasing force on the valve member 20 toward the closed position or causing the diaphragm 30 to increase the biasing force exerted on the valve member 20. The biasing force from the diaphragm 30 can be resisted by the radially extending surface 84 of the female connector 76 contacting the inner threads 56 of the housing 22. However, when the female connector 76 is withdrawn from the male luer 10, the diaphragm 30 can return the sealing portion of the valve member 20 to the closed position within the luer tip 26.

Despite the relative movement between the housing 22 and the valve member 20, the sealing member 44 can maintain a fluid barrier between the outer surface of the tube 32 and the inner surface of the luer tip 26. In some embodiments, where the sealing member 44 comprises the generally rectangular protrusions 70, the position of the sealing member 44 can be maintained by the protrusions 70. In some embodiments, the sealing member 44 can be positioned by adhering the outer surface of the protrusions 70 to an inner surface of the luer tip 26. In some embodiments, the sealing member 44 can be positioned by adhering the outer surface of the seal 44 to an inner surface of the luer tip 26 or to an outer surface of the valve tube 32. Other suitable means of fixing the position of the sealing member 44 can also be used.

As shown in FIG. 2C, in the opened configuration, the fluid passageway 80 of the female connector 76 can communicate with the passageway 54 of the valve member 20 so as to allow fluid to flow through the passageway 54 and the fluid passageway 80 of the female connector 76 in either direction. Fluid can thereby flow from tubing (not shown) or another connector or conduit that can be attached to the luer connector 10, into the passageway 54 of the housing 22, through the opening or openings 64 into the interior space 60 within the luer tip 26, out from the interior space 60 within the luer tip 26 through the opening 38 at the distal end portion 26a of the luer tip 26 and into the fluid passageway 80 of the female connector 76, and vice versa. A fluid-tight closure can also be formed between corresponding tapers of the outside surface of the tip 26 and the inner surface 86 of the female connector 76.

As discussed above, as the valve member 20 opens, it can cause the diaphragm 30 to be compressed and the volume of fluid that can be contained within the cavity 33 of the diaphragm 30 can accordingly decrease. In some embodiments, while the diaphragm 30 is being compressed (which can decrease the volume of fluid in the diaphragm 30), the fluid within the diaphragm 30 can be subjected to an increased pressure due to the compression of the diaphragm 30. With the female connector 76 fully connected, the volume of the cavity 33 in the diaphragm 30 can be reduced to V2. V1 can be larger than V2, and in some embodiments, the difference in volume between V1 and V2 can generally correspond to the volume of residual fluid, such as a drip, that is expected to remain on the outside of the male luer upon disconnection from the female luer.

Conversely, in some embodiments, when the female connector 76 is removed from the luer connector 10, and the valve member 20 can move back toward the closed position, thereby causing the volume within the cavity 33 of the diaphragm 30 to expand back to the closed position volume V1. The expansion of the interior volume of the diaphragm 30 can cause a reduced pressure or suction to be generated within the diaphragm 30. This reduced pressure or suction can cause the cavity 33 to draw at least some of the fluid that is within the passageway 60 within the luer tube 26 or on the outside surface of the end of the tube 32a back into the diaphragm 30. The suction or draw-back is beneficial in that it can prevent fluid from dripping out of the opening 38 as the female connector 76 is being removed. In some embodiments, the luer connector 10 may be used to control the flow of fluids or medicaments that are harmful or corrosive, such as by substantially preventing one or more drops from dripping out of the opening 38 as the female connector 76 is being removed.

Figure 2E:
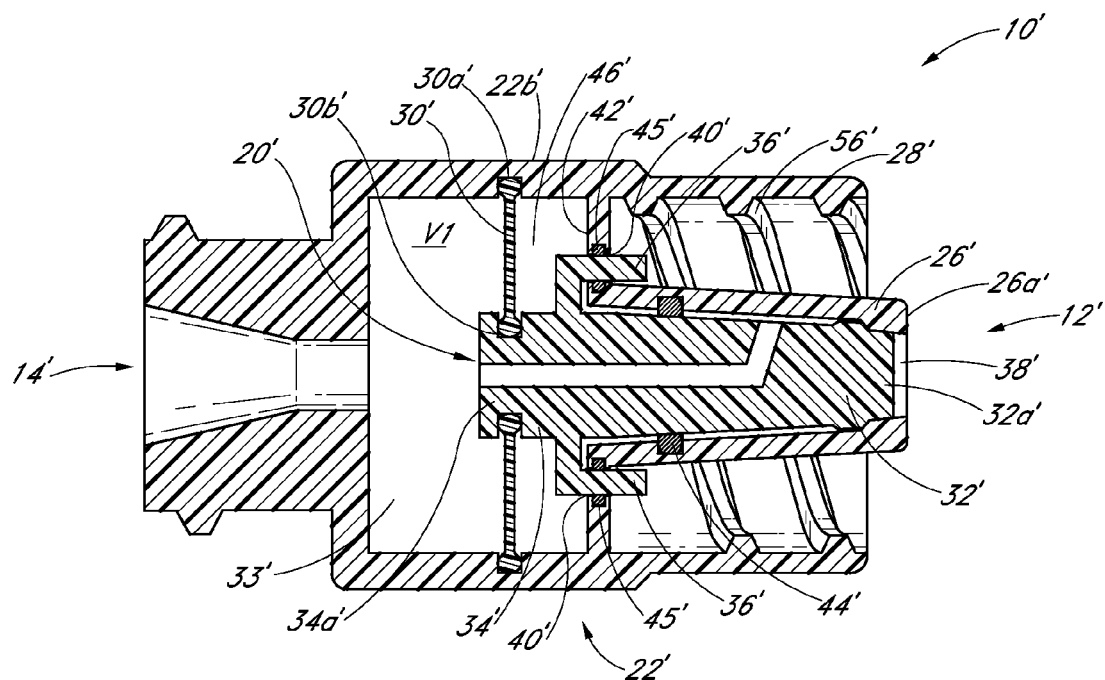
FIG. 2E is a cross-sectional view of another embodiment of a luer connector in a closed position.
Figure 2F:
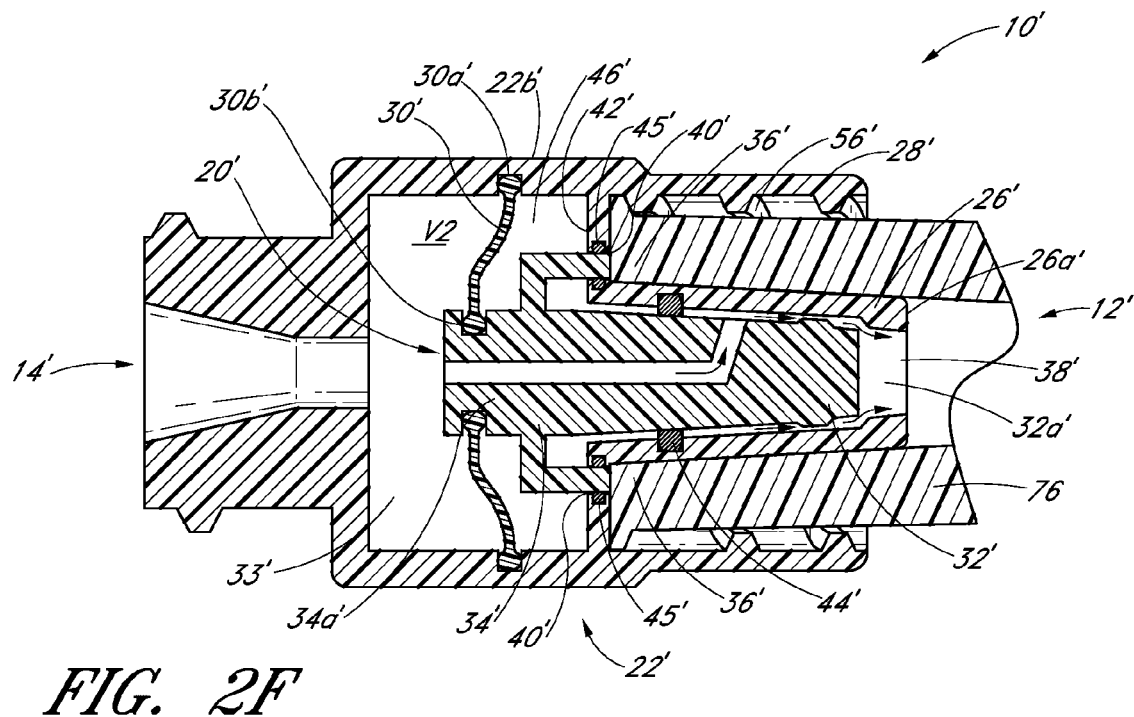
FIG. 2F is a cross-sectional view of the embodiment of the luer connector shown in FIG. 2E in an open position.

Referring now to FIGS. 2E-2F, other embodiments of the closeable luer connector 10' will be described. In some embodiments, the luer connector 10' may comprise any of the components, features, materials, sizes, geometries, details, or configurations of any of the other luer connectors disclosed herein. FIG. 2E is a cross-sectional view of the luer connector 10' in a closed position. As described above, when the valve member 20' of the luer connector 10' is in the closed position, fluid is generally prevented from flowing through the luer connector 10'. FIG. 2F is a cross-sectional view of the embodiment of the luer connector 10' taken through the longitudinal center of the luer connector 10', showing the valve member 20' in an open position due to the engagement of a female connector 76 with the luer connector 10'. The flow of fluid through the luer connector 10' is represented by arrows in FIG. 2F. As described above, when the valve member 20' of the luer connector 10' is in the open position, fluid can be generally permitted to flow through the luer connector 10'.

In some embodiments, the luer connector 10' can be the same or similar to the luer connector 10 described above, with certain differences as illustrated and/or described below. Accordingly, in some embodiments, the luer connector 10' may operate in the same or similar manner as compared to the luer connector 10 described above. In the illustrated embodiment, the valve member 20' can comprise a tube 32' projecting from a valve base 34' toward the first end 12' of the connector 10', and one or more arms or struts 36' supported by the valve base 34' such that an axial force imparted on the valve struts 36' is generally transferred directly to the valve base 34'. As shown in FIG. 2E and discussed above, the struts 36' of the valve member 20' can extend through openings 40' in the internal wall 42' of the housing 22' such that, in the closed position, the ends of the struts 36' extend past the internal wall 42' toward the first end 12' of the connector 10'. In the illustrated embodiment, an annular seal 45' can seal each of the openings 40' through which a valve strut 36' passes.

The struts 36' can be configured to engage the proximal end 84 of the female connector 76 as the female connector 76 advances into engagement with the closeable male luer 10'. To engage the male luer 10' and female connector 76, as is shown in FIG. 2F, the radially extending surface or surfaces 84 of the female connector 76 can be threaded into the inner threads 56' of the male luer 10'. In an assembled configuration, the valve struts 36' can be positioned so as to be adjacent to the tip 26'. In the illustrated embodiment, the tube 32', the valve base 34', and the valve struts 36' can be integrally formed so as to be a unitary member. However, in some embodiments, the tube 32', the valve base 34', and the valve struts 36' may be separately formed and bonded, fused, adhered, or otherwise attached together to form the valve member 20' illustrated in FIGS. 2E and 2F. As with any of the valve struts described above, the valve struts 36' can be suitably rigid and configured such that, when a female connector 76 is threadingly engaged with the luer connector 10', the struts 36' can be axially depressed toward the diaphragm member 30', causing the diaphragm 30' to deflect toward the second end 14' of the luer connector 10', as illustrated in FIG. 2F.

In some embodiments, as in the illustrated embodiment, the diaphragm 30' can be formed so as to define a pair of generally planar surfaces and so as to have an outside circular perimeter and an opening through the center thereof. In the illustrated embodiment, the outer portion 30a' of the diaphragm 30' (which can be generally spherical) can be sealably secured to the inside surface of the side wall 22b' of the housing 22'. In some embodiments, as in the illustrated embodiments, the housing 22' may define an annular depression which supports or secures the outer portion 30a' of the diaphragm 30' so as to prevent the diaphragm 30' from moving from its desired position. Similarly, in the illustrated embodiment, the inner portion 30b' of the diaphragm 30' can be sealably secured to the outside surface of the aft portion 34a' of the valve base 34'. In some embodiments, as in the illustrated embodiments, the aft portion 34a' of the valve base 34' may define an annular depression which is configured to support or secure the inner portion 30b' of the diaphragm 30' so as to prevent the diaphragm 30' from moving from its desired position.

In some embodiments, as in the illustrated embodiment, the diaphragm 30' can be resilient and biased toward its relaxed planar shape, as illustrated in FIG. 2E. The diaphragm 30' can be positioned so as to exert a force on the valve member 20' that biases the valve member 20' toward the closed position. In particular, in the illustrated embodiment, the diaphragm 30' can bias the tube member 32' to sealably close against the inside surface of the luer tip 26'. In some embodiments, the diaphragm 30' can be positioned within the luer connector 10' so that, when the valve member 20' is in the closed position, the diaphragm 30' is partially deflected from its relaxed state so as to increase the bias force that the diaphragm 30' exerts on the valve member 20'.

As shown in FIGS. 2E and 2F, the inner portion of the connector 20' may be split into two portions, the inner cavity 33' and the chamber 46'. The diaphragm 30' can be configured so that the volume within the cavity 33' when the valve member 20' is in the closed position (e.g. represented by V1 in FIG. 2E) is greater than volume within the cavity 33' when the valve member 20' is in the open position (e.g. represented by V2 in FIG. 2F). In this configuration, the volume of space within the cavity 33' can increase when the valve member 20' moves from the open position to the closed position, thereby creating a force of suction that can reduce the amount of fluid or medicament that can flow through or drip out of the opening 38' as the valve member 20' closes, by drawing such fluid back toward the cavity 33'.

As described, in some embodiments, the valve member 20' may be configured such that the valve struts 36' can be directly attached to either the tube 32' or the valve base 34' so that an axial force imparted on the valve struts 36' is also generally imparted on the tube 32' or the valve base 34'.

Figure 2G:
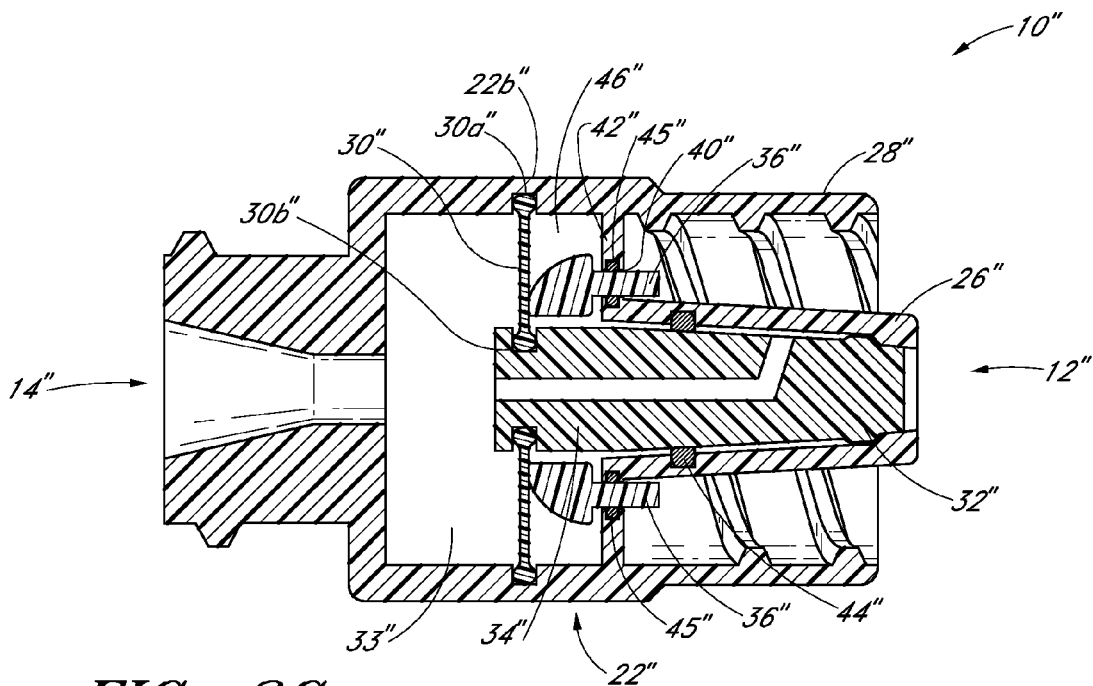
FIG. 2G is a cross-sectional view of another embodiment of a luer connector in a closed position.
Figure 2H:
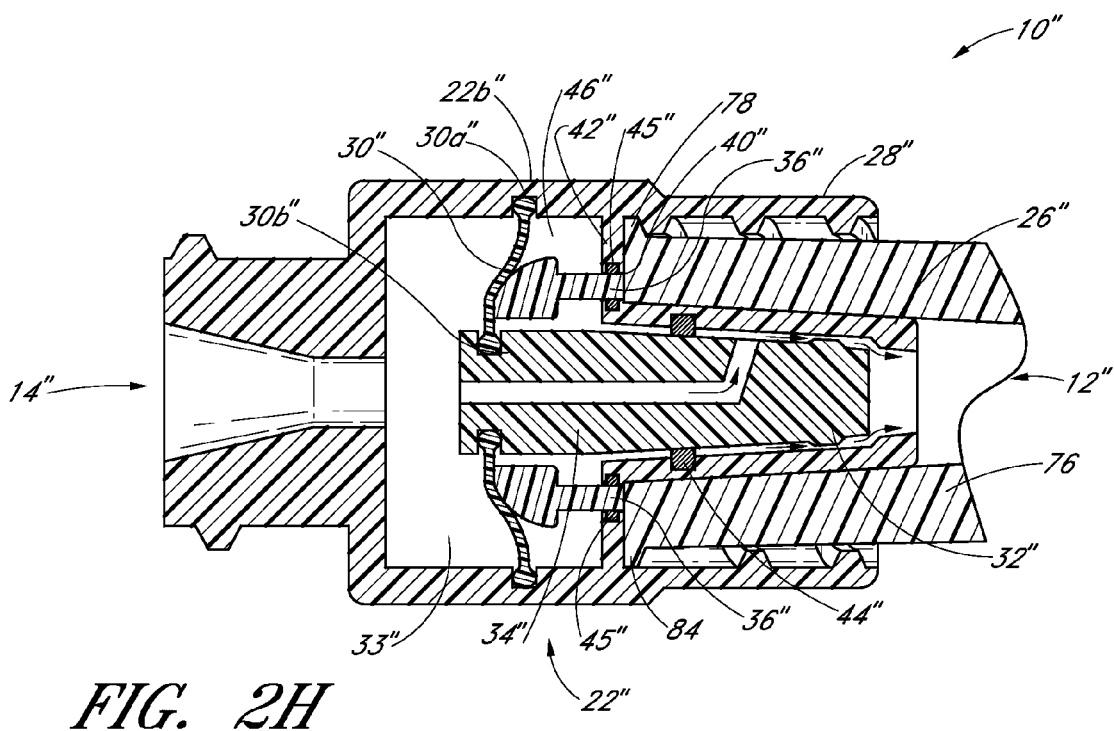
FIG. 2H is a cross-sectional view of the embodiment of the luer connector shown in FIG. 2G in an open position.

However, in other embodiments, as in the embodiment of the luer connector 10" illustrated in FIGS. 2G and 2H, the tube 32" and the valve base 34" may be integrally formed while the struts 36" can be separately formed and independently movable relative to the tube 32" and the valve base 34". In the embodiment illustrated in FIGS. 2G and 2H, the struts 36" each can exert an axial force on at least a portion of the diaphragm 30" when struts 36" are displaced from the insertion of a female connector 76 into the shroud 28" as described above, thereby deflecting the diaphragm 30". In this configuration, as the diaphragm 30" is deflected, the valve member 20" can be moved toward the open position because the diaphragm 30" can be secured to the valve base 34".

Figure 2I:
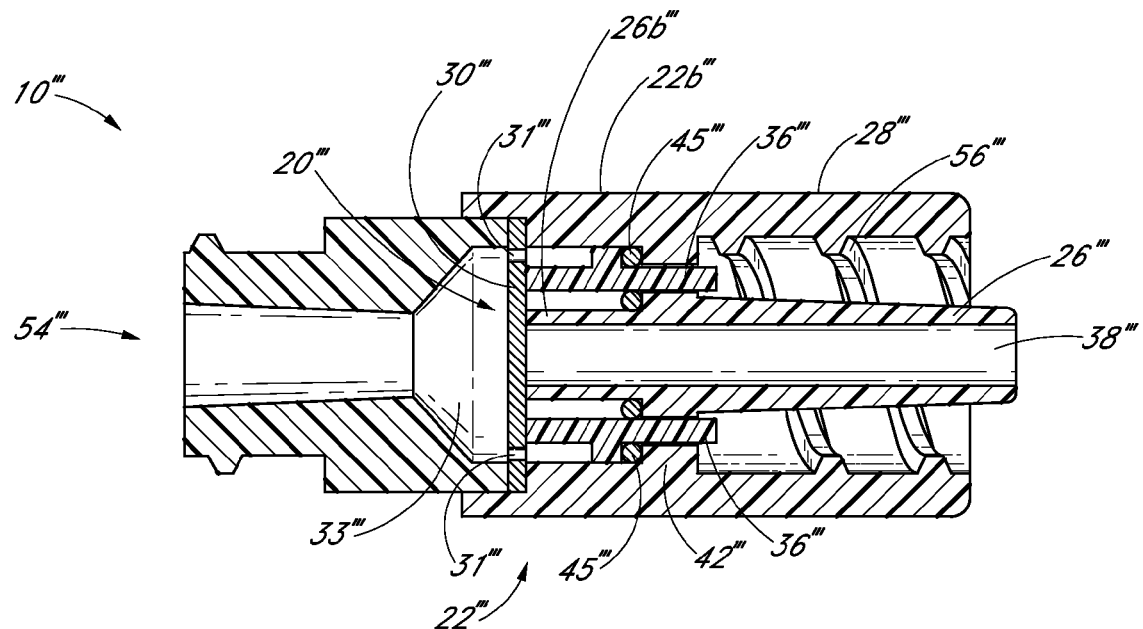
FIG. 2I is a cross-sectional view of another embodiment of a luer connector in a closed position.
Figure 2J:
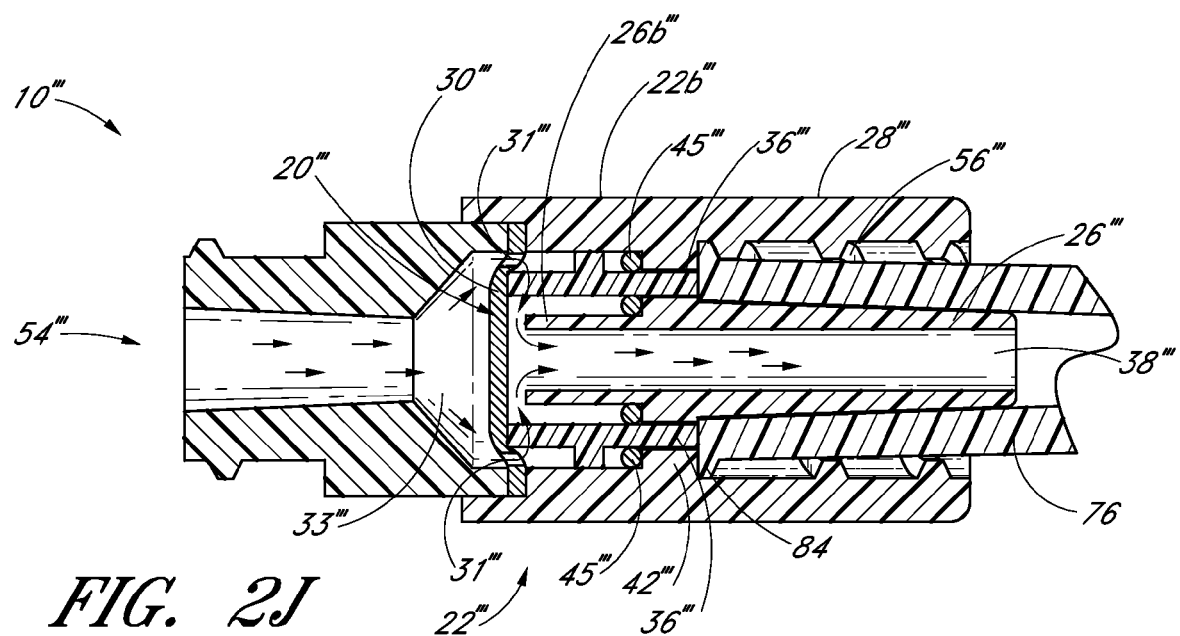
FIG. 2J is a cross-sectional view of the embodiment of the luer connector shown in FIG. 2I in an open position.

Referring now to FIGS. 2I-2J, some embodiments of the closeable luer connector 10''' will be described. In some embodiments, the luer connector 10''' may comprise any of the components, features, materials, sizes, geometries, details, or configurations of any of the other luer connectors disclosed herein. FIG. 2I is a cross-sectional view of the luer connector 10''' in a closed position. As described above, when the valve member 20''' of the luer connector 10''' is in a closed position, fluid is generally prevented from flowing through the luer connector 10'''. FIG. 2J is a cross-sectional view of the embodiment of the luer connector 10''' in an open position due to the engagement of a female connector 76 with the luer connector. The flow of fluid through the luer connector 10''' is represented by arrows in FIG. 2J. As described above, when the valve member 20''' of the luer connector 10''' is in the open position, fluid can be generally permitted to flow through the luer connector 10'''.

In some embodiments, the luer connector 10''' can be the same or similar to the luer connector 10 described above, with certain differences in some versions as illustrated and/or described below. Accordingly, in some embodiments, the luer connector 10''' may operate in the same or similar manner as compared to the luer connector 10 described above. The valve member 20''' can comprise one or more valve arms or struts 36''' (two are shown), each of which can extend through an opening 40''' in the internal wall 42''' of the housing 22''' toward the first end 12''' of the connector 10'''. In the illustrated embodiment, two or more annular seals 45''' can seal the openings 40'''. The struts 36''' can be configured to engage the proximal ends 84 of the female connector 76 as the female connector 76 advances into engagement with the closeable male luer 10'''. To engage the male luer 10''' and female connector 76, as is shown in FIG. 2J, the radially extending surface or surfaces 84 of the female connector 76 can be threaded into the inner threads 56''' of the luer connector 10'''.

The luer connector 10''' can also comprise a resilient diaphragm 30''' that, in some embodiments, can be generally planar with a circular perimeter. In some embodiments, as in the illustrated embodiment, the outer, peripheral portion of the diaphragm 30''' may be supported by the housing 22''', while the middle portion of the diaphragm 30''' can be generally unsupported. In some embodiments, the diaphragm 30''' can be positioned within the housing 22''' so that, when the valve member 20''' is in the closed position, the middle portion of the diaphragm 30''' can sealably contact the aft or rear portion 26b''' of the luer tip 26'''. With reference to FIGS. 2I and 2J, the diaphragm 30''' can comprise two or more openings 31''' therethrough that allow fluid flowing through the passageway 54''' to flow through the diaphragm 30''', particularly when the valve member 20''' is in an open position. In some embodiments, the openings 31''' can be positioned on the diaphragm 30''' at locations that can be radially outward from the position where the diaphragm 30''' makes contact with the aft portion 26b''' of the luer tip 26'''. In this embodiment, the luer tip 26''' can be stationary with regard to the housing 22''', even when the luer connector 10''' is changed from the open to the closed position. Therefore, in this configuration, when the valve member 20''' is in the closed position, fluid flowing through the openings 31''' in the diaphragm 30''' can be prevented from flowing from the inner cavity 33''' into the inside portion of the luer tip 26''' by the seal that is created between the diaphragm 30''' and the aft portion 26b''' of the luer tip 26'''.

The valve struts 36''' can be suitably rigid and configured such that, when a female connector 76 is threadingly engaged with the luer connector 10''', the struts 36''' can be axially displaced toward the diaphragm 30''', causing the diaphragm 30''' to deflect toward the second end 14''' of the luer connector 10''', as illustrated in FIG. 2J. When the diaphragm 30''' is displaced by the struts 36''', fluid passing through the passageway 54''' and the openings 31''' can then flow between the resilient member 30''' and the aft portion 26b''' of the luer tip 26''', and out through the opening 38'''.

In some embodiments, as in the illustrated embodiment, the diaphragm 30''' can be, resilient and biased toward a planar shape, as illustrated in FIG. 2I, so as to exert a force against the aft portion 26b''' of the luer tip 26''' sufficient to bias the valve struts 36''' to the closed position and to seal the diaphragm 30''' against the aft portion 26b''' of the luer tip 26'''. In some embodiments, the diaphragm 30''' can be positioned within the luer connector 10''' so that, when the valve member 20''' is in the closed position, the diaphragm 30''' is partially deflected from its relaxed state so as to increase the spring force that the diaphragm 30''' exerts on the valve struts 36''' and the aft portion 26b''' of the luer tip 26'''.

Figure 4A:
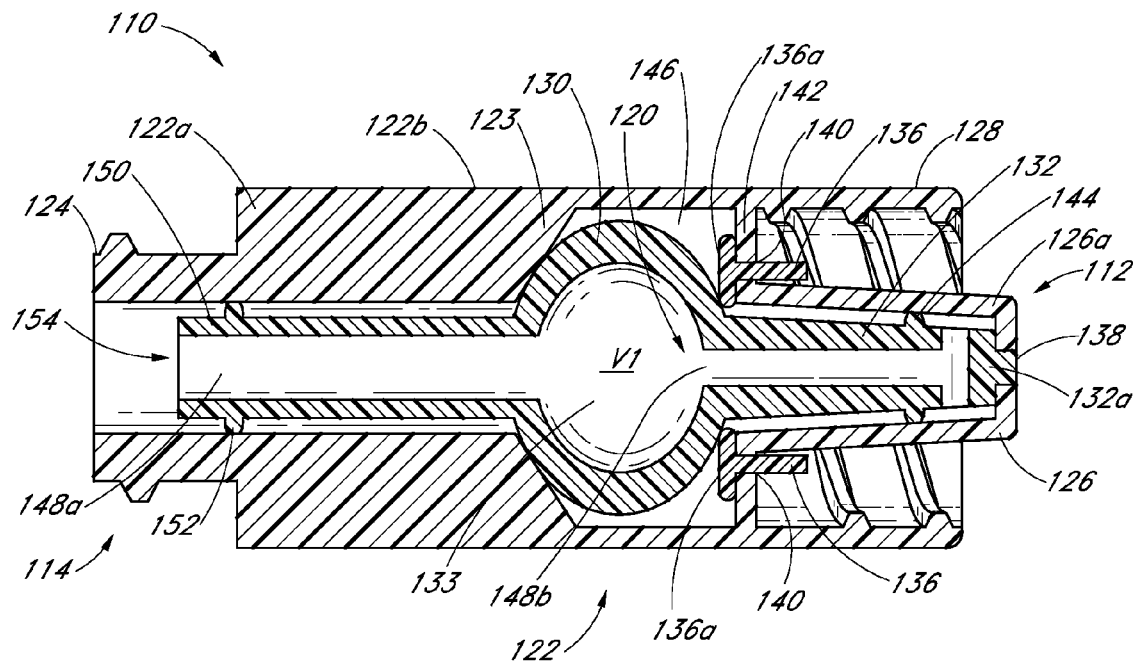
FIG. 4A is a cross-sectional view of another embodiment of a luer connector in a closed position.
Figure 4B:
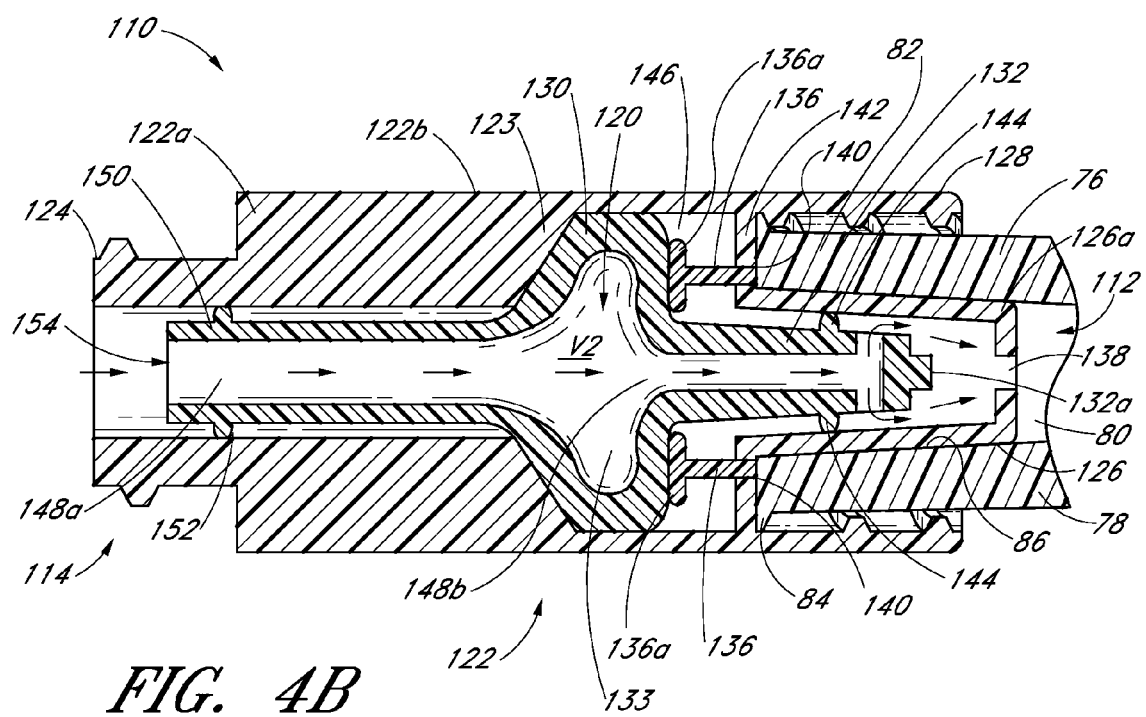
FIG. 4B is a cross-sectional view of the embodiment of the luer connector shown in FIG. 4A in an open position.

Referring now to FIGS. 4A-4B, some embodiments of the closeable luer connector 110 will be described. In some embodiments, the luer connector 110 may comprise any of the components, features, materials, sizes, geometries, details, or configurations of any of the other luer connectors disclosed herein. FIG. 4A is a cross-sectional view of the luer connector 110 in a closed position. As described above, when the valve member 120 of the luer connector 110 is in the closed position, fluid is generally prevented from flowing through the luer connector 110. FIG. 4B is a cross-sectional view of the embodiment of the luer connector 110 in an open position due to the engagement of a female connector 76 with the luer connector. The flow of fluid through the luer connector 110 is represented by arrows in FIG. 4B. As described above, when the valve member 120 of the luer connector 110 is in the open position, fluid can be generally permitted to flow through the luer connector 110. As with any embodiment of the luer connector described herein, the seal or seals formed in the housing by the valve member is generally sufficient to resist fluid flow during normal operating conditions.

As illustrated in FIG. 4A, some embodiments of the assembled luer connector 110 can comprise a housing 122, a port 124 positioned near the second end 114 of the luer connector 110, a luer tip 126 positioned near the first end 112 of the luer connector 110, a shroud 128 surrounding at least a portion of the luer tip 126, a bladder member 130, and the valve member 120 mentioned above. The bladder member 130 can be formed from a generally fluid impervious, suitable resilient material and may define an internal cavity 133. In some embodiments, the bladder member 130 may be ovular such that a cross section of the bladder member 130 taken along a longitudinal axis of the connector 110 is substantially ovular with the major axis of the bladder member 130 being substantially perpendicular to the longitudinal axis of the connector 110 when the connector 110 is in the closed position. In some embodiments, the wall portion of the bladder member 130 is concave toward the longitudinal axis of the connector so as to form a substantially ovular inner cavity. In some embodiments, the cavity is substantially circular. Other wall shapes may also be incorporated to enhance or adjust the rebound bias of the tube 132 toward the first end 112 of the connector 110.

As illustrated, the bladder member 130 and the valve member 120 can be disposed within the housing 122. The valve member 120 can comprise a tube 132 positioned within the inside surface of the luer tip 126 and one or more valve struts 136 (two are shown), that can be in engaging communication with the bladder member 130. In some embodiments, in an assembled configuration, the valve struts 136 can be positioned so as to be adjacent to the tip 126 along the side of the tip 126. In some embodiments, each of the valve struts 136 can define a planar base portion 136a on the end of the valve strut 136 closest to the second end 114 of the luer connector 110.

In some embodiments, the valve member 120 can comprise only one valve strut 136, or two, three or more valve struts 136. When the luer connector 110 is in the closed position, the outer surface of the distal portion 132a of the valve tube 132 can be sealingly closed against the inner surface of the distal portion 126a of the luer tip 126 such that fluid can be generally prevented from flowing through the opening 138 formed in the distal end 126a of the luer tip 126. In some embodiments, the base portion 136a of each of the valve struts 136 can be interconnected, so as to form in the annular ring around the tube 132. In some embodiments, therefore, each of the valve struts 136 can be interconnected by the base portion 136a. In some embodiments, however, each of the valve struts 136 can be independent so as to translate independently relative to the bladder member 130 and relative to the other valve struts 136, if any, that can be supported within the housing 120. In some embodiments, where the valve struts 136 are each independently movable, the base portion 136a can therefore be disconnected from the base portion 136a of the other valve struts 136. In some embodiments, where the valve struts 136 are each independently movable, the base portion 136a can define a circular, square, triangular, ovular, arcuate, or other suitable shape.

As mentioned, in the illustrated embodiment, the tube 132 can be slidably supported so as to translate axially within the luer tip 126. Further, the valve struts 136 can be configured so as to slide within the openings 140 formed through the internal wall 142 of the housing 122. The number of openings 140 through the internal wall 142 can be equal to the number of the valve struts 136 that can be supported within the housing 122. An annular sealing member 144 can be positioned between the outside surface of the valve tube 132 and the inside surface of the luer tip 126 so as to prevent any fluid from flowing into the chamber 146 during normal use. In the illustrated embodiment, the chamber 146 is the space that is generally confined by the end wall 122a of the housing 122, the sidewall 122b (which can be cylindrically shaped) of the housing 122, and the internal wall 142 formed on the housing 122. Chamber 146 generally extends around the bladder member 130 and is generally isolated from any fluid flowing through the connector 110. The sealing member 144 can comprise any of the materials, geometries, sizes, or other details of configurations of any other seal described herein. In some embodiments, the sealing member 144 can be formed from the same material as the valve tube 132 and can be formed integrally with the valve tube 132. In some embodiments, the sealing member 144 can be formed from a different material as compared to the valve tube 132. In some embodiments, the sealing member 144 can be formed separately from the valve tube 132 and positioned at the desired axial location of either the valve tube 132 or the inside surface of the luer tip 126. Accordingly, in some embodiments, either the inside surface of the luer tip 126 or the valve tube 132 can comprise features such as channels or depressions to secure the sealing member 144 in the desired location. In some embodiments, the end wall 122a can be formed integrally with at least the sidewalls 122b of the housing 122. In some embodiments, the end wall 122a can be formed separately as compared to at least the sidewalls 122b and adhered or attached thereto in a subsequent manufacturing step.

In the illustrated embodiment, the bladder member 130 can be supported on one end by the projection 123 (which can be annular), laterally by the sidewalls 122b of the housing 122 (which can be cylindrically shaped), and at an other end by the base portions 136a of the valve struts 136. In some embodiments, as with other components, the projection 123 can be omitted from the housing such that the bladder member is supported by the end portion 122a of the housing 122 instead of by the projection 123. In the illustrated embodiment, the projection 123 can be formed so as to effectively allow the length of the housing 122 to be increased without increasing the volume of the bladder member 130. It may be desired to increase the length of the housing 122 to provide a longer gripping surface for the user or medical practitioner. Accordingly, in some of the embodiments, such as those described above wherein the housing 122 does not comprise the projection 123 or comprises a shorter projection 123, the length of the housing 122 may be shorter than as illustrated in FIG. 4A. In some embodiments, the ratio of the radial thickness of the projection 123 to the sidewall 122b can be in the range of approximately 2 to 1 to approximately 10 to 1. In some embodiments, the ratio is approximately 7 to 1.

In the illustrated embodiment, the bladder member 130 can comprise a pair of opposing openings 148a, 148b through which fluid can pass. In some embodiments, the bladder member 130 can be resilient and biased toward an expanded position, as illustrated in FIG. 4A, so as to exert a force on the valve member 120 that biases the valve member 120 toward the closed position. In particular, in the illustrated embodiment, the bladder member 130 can bias the tube member 132 to sealably close against the inside surface of the luer tip 126. Further, the bladder member 130 can be configured so that the volume within the inner cavity 133 of the bladder member 130 when the valve member 120 is in the closed position (which is represented by V1 in FIG. 4A) can be greater than the volume of the cavity 133 within the bladder member 130 when the valve member 120 is in the open position (which is represented by V2 in FIG. 4B). Thus, the volume of the cavity 133 within the bladder member 130 can decrease when the valve member 120 moves from the closed position to the open position and can increase when the valve member 120 moves from the open position to the closed position. By increasing the volume of the cavity 133 within the bladder member 130 as the valve member 120 moves to the closed position, the bladder member 130 can essentially create a force of suction that can reduce the amount of fluid or medicament that can flow through or drip out of the opening 138 as the valve member 120 is in the process of closing by drawing such fluid back toward the bladder member 130.

In the illustrated embodiment, the luer connector 110 can comprise a tube 150 positioned within the inside surface of the port 124 at the second end 114 of the luer connector 110. In the illustrated embodiment, the tube 150 can be integrally formed with the bladder member 130 and the tube 132 at the first end 112 of the luer connector 110. Additionally, the luer connector 110 can comprise a sealing member 152 (which can be annular) configured to prevent fluid or medicament from entering into the chamber 146 from the port 124. The sealing member 152 can comprise any of the materials, geometries, sizes, or other details of configurations of any other steel described herein. In some embodiments, the sealing member 152 can be positioned between the outside surface of the tube 150 and the inside surface of the port 124 and can provide a generally fluid tight seal between the tube 150 and the port 124. In some embodiments, the sealing member 152 can be formed from the same material as the tube 150 and can be formed integrally with the tube 150. In some embodiments, the sealing member 152 can be formed separately from the tube 150 and positioned at the desired axial location of either the tube 150 or the inside surface of the port 124. Accordingly, in some embodiments, either the inside surface of the port 124 or the tube 150 can comprise features such as channels or depressions to bias the sealing member 152 to be secured in the desired location.

In some embodiments, as in the illustrated embodiment, the bladder member 130, the tube 132, sealing member 144 and the tube 150 in the sealing member 152 can all be integrally formed from the same material. In some embodiments, however, any of these components can be formed separately and supported in the desired position as described above or in any other suitable manner. The housing 122 can be generally a tube-like structure with a passageway 154 that can extend from the second end 114 of the connector 110 through the axial center of the luer connector 110. In some embodiments, when the luer connector 110 is in the open configuration as illustrated in FIG. 4B, the passageway 154 can permit fluid to flow from the second end 114 through the port 124, the tube 150, the bladder member 130, the tube 132, and out through the opening 138 in the luer tip 126 positioned at the first end 112 of the luer connector 110. With reference to FIGS. 4A and 4B, near the second end 114 of the luer connector 110, the port 124 and the corresponding section of the fluid passageway 154 can be sufficiently wide so as to accommodate a section of standard-diameter medical tubing inserted therein. The length, diameter, or other features and of the housing 122 (or any housing described herein) can be the same as any other housing described herein. As with other embodiments of the connector, the port 124 can be made to comply with applicable standards and/or regulations, such as the ANSI standards.

Additionally, the shroud 128 can be sized and configured as described above or as desired to securely or removably attach the luer connector 110 to another medical implement. Further, the housing 122, tip 126, bladder member 130, or any other components or features of the luer connector 110 may comprise any of the materials, shapes, features, sizes, or other configurations or details described with regard to any other tip member disclosed herein. As with other embodiments, the luer tip 126 can be made to comply with applicable standards and/or regulations, such as the ANSI standards.

With reference to FIG. 4B, as the male luer connector 110 and female connector 76 move towards each other into threaded engagement, the proximal end 84 of the tip of the female connector 76 contact the struts 136 of the valve member 120. As the male luer connector 110 and female connector 76 move further into threaded engagement, the struts 136 can be moved toward the second end 114 of the male connector 110 by the female connector 76, thereby displacing the valve member 120 relative to the housing 122. Thus, the distal end portion 132a of the tube 132 can move away from the interior distal end portion 126a of the tip 126 in the direction of the second end 114 of the male connector 110 as the male luer connector 110 and female connector 76 move further into threaded engagement. As these two surfaces move apart from one another, a gap can form between the tube 132 and the luer tip 126, permitting fluid to pass through the opening 138 into the fluid passageway 80 of the female connector 76, or vice versa.

In some embodiments, as the valve member 120 moves relative to the housing 122, bladder member 130 compresses, causing the bladder member 130 to exert a force on the valve member 120 biasing the valve member 120 toward the closed position. The biasing force from the bladder member 130 can be resisted by the radially extending surface 78 of the female connector 76 contacting the inner threads 156 of the housing 122. However, when the female connector 76 is withdrawn from the male luer 110, the bladder member 130 can return the sealing portion of the valve member 120 to the closed position within the luer tip 126.

As shown in FIG. 4B, in the opened configuration, the fluid passageway 80 of the female connector 76 can communicate with the passageway 154 of the valve member 120 so as to allow fluid to flow through the passageway 154 and the fluid passageway 80 of the female connector 76 in either direction. Fluid can thereby flow from tubing (not shown) or another connector or conduit that can be attached to the male luer 110, into the passageway 154 of the valve member 120, through the opening or openings 64 into the interior space 60 within the luer tip 126, out from the interior space 60 within the luer tip 126 through the opening 138 at the distal end portion 126a of the luer tip 126 and into the fluid passageway 80 of the female connector 76, and vice versa. A fluid-tight closure can also be formed between corresponding tapers of the outside surface of the tip 126 and the inner surface 86 of the female connector 76.

As discussed above, as the valve member 120 opens, causing the bladder member 130 to be compressed, the volume of fluid that can be contained within the cavity 133 of the bladder member 130 accordingly decreases. In some embodiments, a constant source of positive pressure can be imparted on the passageway 154 at the second end 114 of the luer connector 110 while the bladder member 130 is being compressed (which decreases the volume of fluid in the cavity 133 of the bladder member 130), and the fluid within the bladder member 130 can be subjected to an increased pressure due to the compression of the bladder member 130. In some embodiments, this increased pressure can cause the fluid within the bladder member 130 to flow through the passageway 154 toward the first end 112 of the luer connector 110 at an increased rate, until the pressure within the bladder member 130 is equilibrated.

Conversely, in some embodiments, when the female connector 76 is removed from the luer connector 110, the valve member 120 can move back toward the closed position, thereby causing the volume of the cavity 133 within the bladder member 130 to transition from volume V2 back to volume V1. The expansion of the interior volume of the bladder member 130 can cause a reduced pressure or suction to be generated within the bladder member 130, in effect a vacuum. This reduced pressure or suction can cause the bladder member 130 to draw at least some of the fluid that is within the passageway 154 near the first end 112, and fluid on the outer surface of the tip 132a, back toward the bladder member 130. In some embodiments, the luer connector 110 may be used to control the flow of fluids or medicaments that are harmful or corrosive. In these circumstances, preventing even a few drops from dripping out of the opening 138 upon removal of the female connector 76 can be especially beneficial.

Figure 4C:
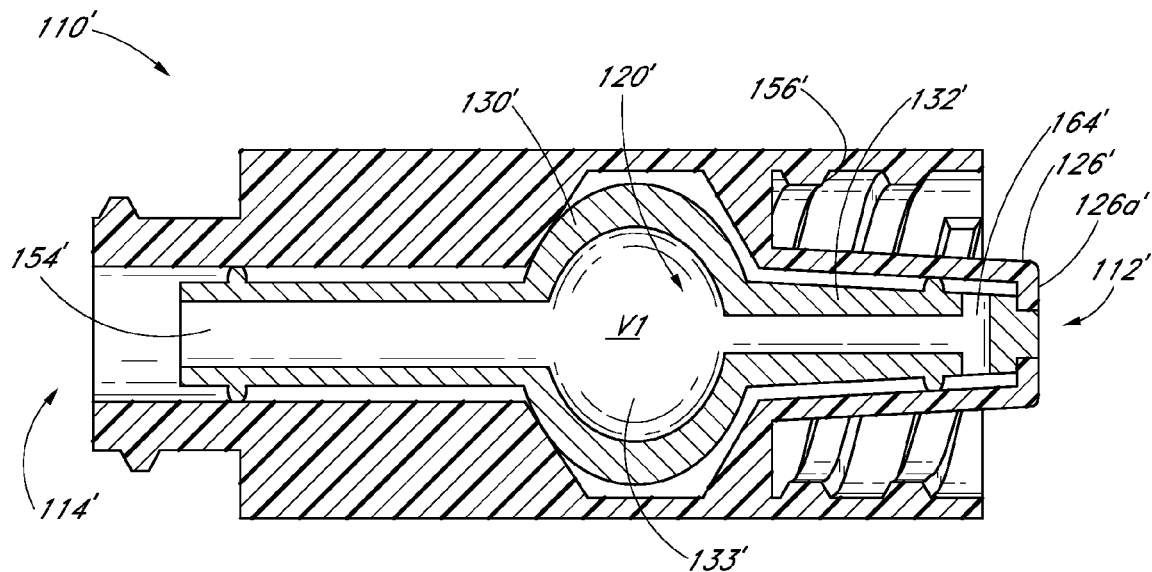
FIG. 4C is a cross-sectional view of another embodiment of a luer connector in a closed position.
Figure 4D:
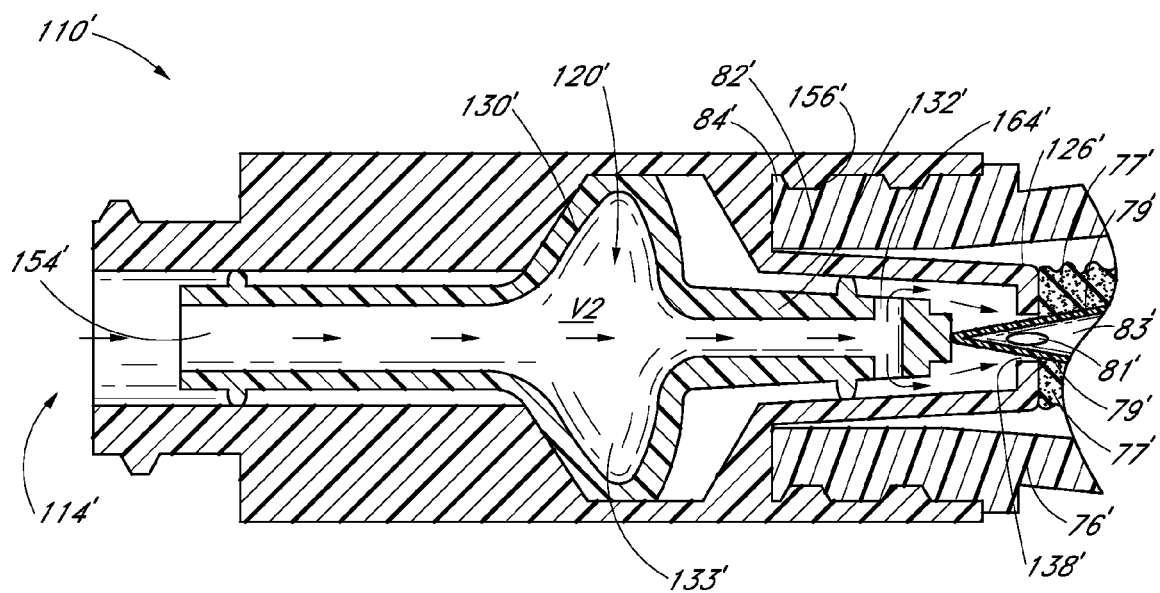
FIG. 4D is a cross-sectional view of the embodiment of the luer connector shown in FIG. 4C in an open position.

Referring now to FIGS. 4C-4D, some embodiments of the closeable luer connector 110' will be described in greater detail. In some embodiments, the luer connector 110' may comprise any of the components, features, materials, sizes, geometries, details, or configurations of any of the other luer connectors disclosed herein. FIG. 4C is a cross-sectional view of the luer connector 110' in a closed position. As described above, when the valve member 120' of the luer connector 110' fluid is in the closed position, fluid is generally prevented from flowing through the luer connector 110'. FIG. 4D is a cross-sectional view of the embodiment of the luer connector 110' in an open position due to the engagement of a female connector 76' with the luer connector. The flow of fluid or medicament through the luer connector 110' is represented by arrows in FIG. 4D. As described above, when the valve member 120' of the luer connector 110' is in the open position, fluid can be generally permitted to flow through the luer connector 110'. As with any embodiment of the luer connector described herein, the seal or seals formed in the housing by the valve member is generally sufficient to resist fluid flow during normal operating conditions for medical valves.

In some embodiments, the luer connector 110' can be the same or similar to the luer connector 110' described above, with certain differences in some versions as illustrated and/or described below. First, in some embodiments, as in the illustrated embodiment, the valve member 120' can be moved from the closed position (as illustrated in FIG. 4C) to the open position (as illustrated in FIG. 4D) without the use of the actuators or struts 136 as described above with respect to luer connector 110. With reference to FIG. 4D, the luer connector 110' can be threadedly engaged with the closeable female connector 76'. The closeable female connector tip 82' of the female connector 76' can have a radially extending surface 84' disposed on its external surface that can engage with the inner threads 156' formed on the inside surface of the shroud 128' of the luer connector 110' to engage the connectors 110', 76' as illustrated. In the illustrated engagement, the fluid conduit 79' of the female connector 76' can advance through the opening 138' in the luer tip 126' by displacing the tube 132' toward the second end 114' of the luer connector 110'. The tube 132' can be configured so as to compress the bladder member 130' when the tube 132' is displaced (as illustrated in FIG. 4D), and to return to its closed position within luer tip 126' (as illustrated in FIG. 4C) when the female connector 76' is disengaged from the luer connector 110'. As the bladder member 130' is compressed, the volume within the cavity 133' of the bladder member 130' can decrease and exert a force on the tube 132' so as to return the tube 132' to the closed position within luer tip 126' (as illustrated in FIG. 4C) when the female connector 76' is disengaged from the luer connector 110'.

Further, as illustrated, as the fluid conduit 79' of the female connector 76' advances through the opening 138' in the luer tip 126', a compressible seal element 77' surrounding the fluid conduit 79' can be compressed so as to allow the fluid conduit 79' to protrude therethrough. The force exerted while engaging the connectors 110', 76' can be sufficient to compress the seal element 77' to expose the one or more openings 81' in the fluid conduit 79'. With the seal element 77' compressed, the fluid passageway 83' can be in fluid communication with the interior space of the luer tip 132'. As can be seen in FIG. 4D, the front surface of the fore portion 126a' can contact the front surface of the sealing member 77' so as to create and maintain a generally fluid tight seal therewith. The compressed seal element 77' can inhibit fluid flowing into the interior of the closeable female connector 76' beyond the luer tip 132'. In this configuration, fluid can flow from the second end 114' of the luer connector 110', through at least the fluid passageway 154', the bladder member 130', the tube 132', the one or more openings 164' in the tube 132', the opening 138' in the luer tip 126', through the one or more openings 81' in the female connector 76', and through the fluid passageway 83'. Thus, in the engaged position, the fluid conduit 79' can protrude through the compressible seal element 77' to a sufficient extent so that the fluid passageway 83' of the female connector 76' is in fluid communication fluid passageway 154' of the luer connector 110'. In some embodiments, the luer connector 110' can also comprise struts (not shown) as described above to allow the valve 120' to be opened and closed, even if a female connector of the type illustrated in FIG. 4D is used.

Figure 5A:
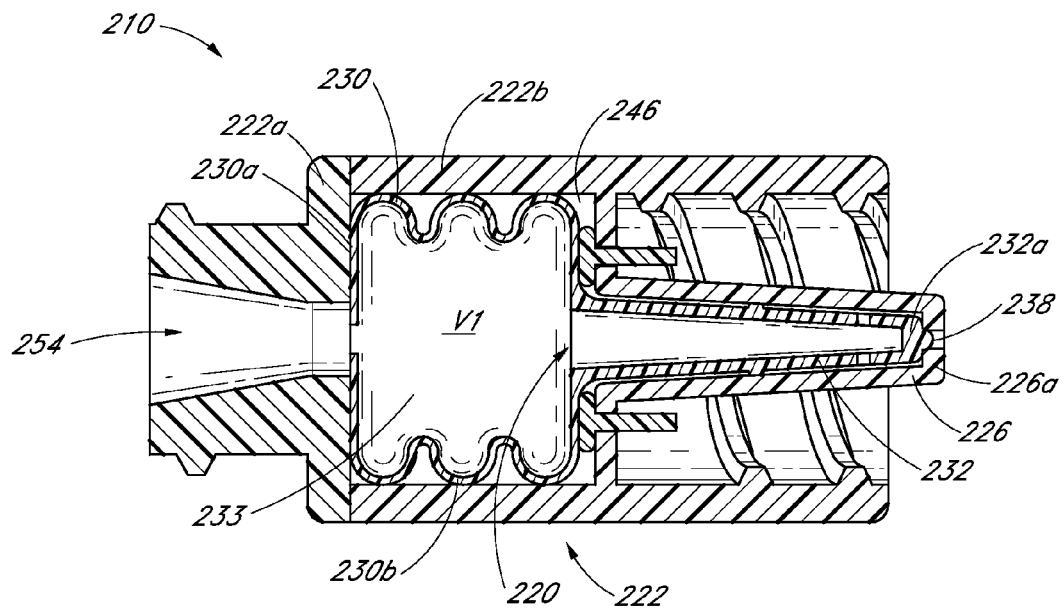
FIG. 5A is a cross-sectional view of another embodiment of a luer connector in a closed position.
Figure 5B:
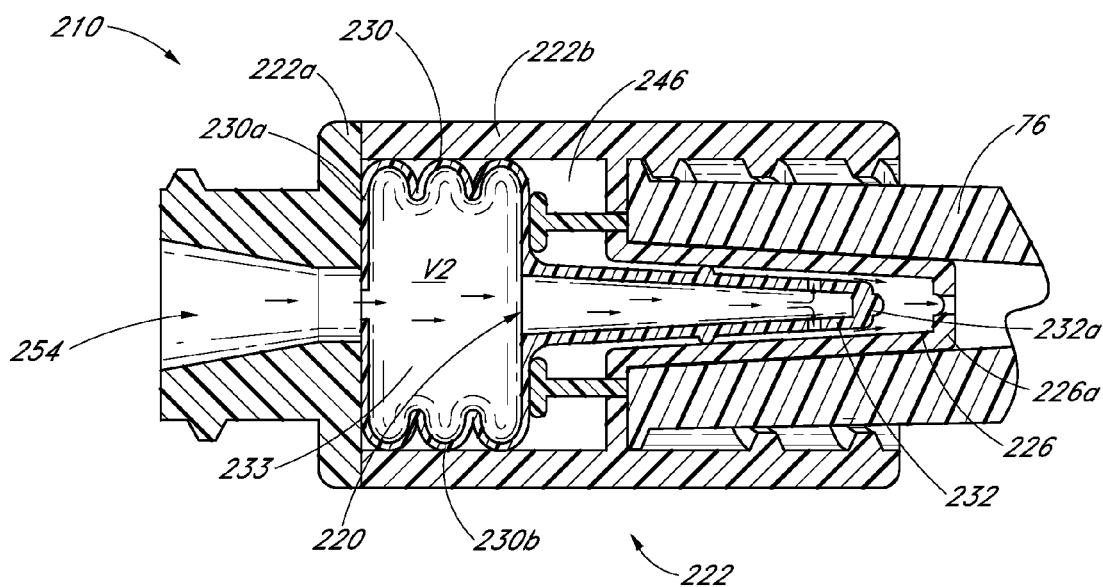
FIG. 5B is a cross-sectional view of the embodiment of the luer connector shown in FIG. 5A in an open position.

Referring now to FIGS. 5A-5B, some embodiments of the closeable luer connector 210 will be described. In some embodiments, the luer connector 210 may comprise any of the components, features, materials, sizes, geometries, details, or configurations of any of the other luer connectors disclosed herein. FIG. 5A is a cross-sectional view of the luer connector 210 in a closed position so that fluid is generally prevented from flowing through the luer connector 210. FIG. 5B is a cross-sectional view of the embodiment of the luer connector 210 in an open position, which can be caused by engagement of a female connector 76 with the luer connector. The flow of fluid or medicament through the luer connector 210 is represented by arrows in FIG. 5B. As described above, when the valve member 210 of the luer connector 210 is in the open position, fluid can be generally permitted to flow through the luer connector 210.

In some embodiments, the luer connector 210 can be the same or similar to the luer connector 110 described above, with certain differences in some versions as illustrated and/or described below. Accordingly, in some embodiments, the luer connector 210 may operate in the same or similar manner as compared to the luer connector 110 described above. In some embodiments, as in the illustrated embodiment, the connector 210 can include a valve member 220 including a tube 232 configured to generally complement the inner surface of the male luer 226. At least a portion of the tube 232 is configured to engage the inner surface of the male luer 226 as discussed with other embodiments disclosed herein.

A bladder member 230 generally encloses an internal cavity 233. The wall 230b of the bladder member 230 can define a corrugated shape, which can have multiple inward and outward folds in the side portion 230b of the bladder member 230. In some embodiments, the multiple inward and outward folds of the corrugated bladder member 230 may facilitate compression of the bladder member 230 as the female connector 76 is threaded into the luer connector 210. As with other connectors disclosed herein, the volume of cavity 233 can vary as the connector 210 moves to and from the open and closed positions. Specifically, the cavity 233 is preferably configured to change from a first large volume V1 when the connector 210 is in the closed position to a second smaller volume V2 when the connector 210 is in the open position. The expansion of the interior volume of the bladder member 230 when moving from the open to the closed position can cause a reduced pressure or suction to be generated within the bladder member 230, in effect a vacuum. This reduced pressure or suction can cause the bladder member 230 to draw at least some of the fluid that is within the passageway 254 near the first end 212, and fluid on the outer surface of the tip 232a of tube 232, back toward the bladder member 230.

Additionally, in some embodiments, the aft portion 230a of the bellows 230 can be sealed to the aft portion 222a of the housing to 222 so as to prevent fluid or medicament that is passing through the luer connector 210 from leaking between the aft portion 230a of the bellows 230 and the end portion 222a of the housing 222 into the chamber 246 within the housing 222. Additionally, the complementary mating surfaces of the end portion 232a of the tube 232 as well as the end portion 226a of the luer tip 226 can define alternative shapes and sizes as compared to other portions of the luer connectors disclosed herein, as illustrated in FIGS. 5A and 5B. The shapes, sizes, features, or any other aspects of the luer connector 210 illustrated in FIGS. 5A and 5B can be implemented in any luer connector disclosed herein.

Figure 5C:
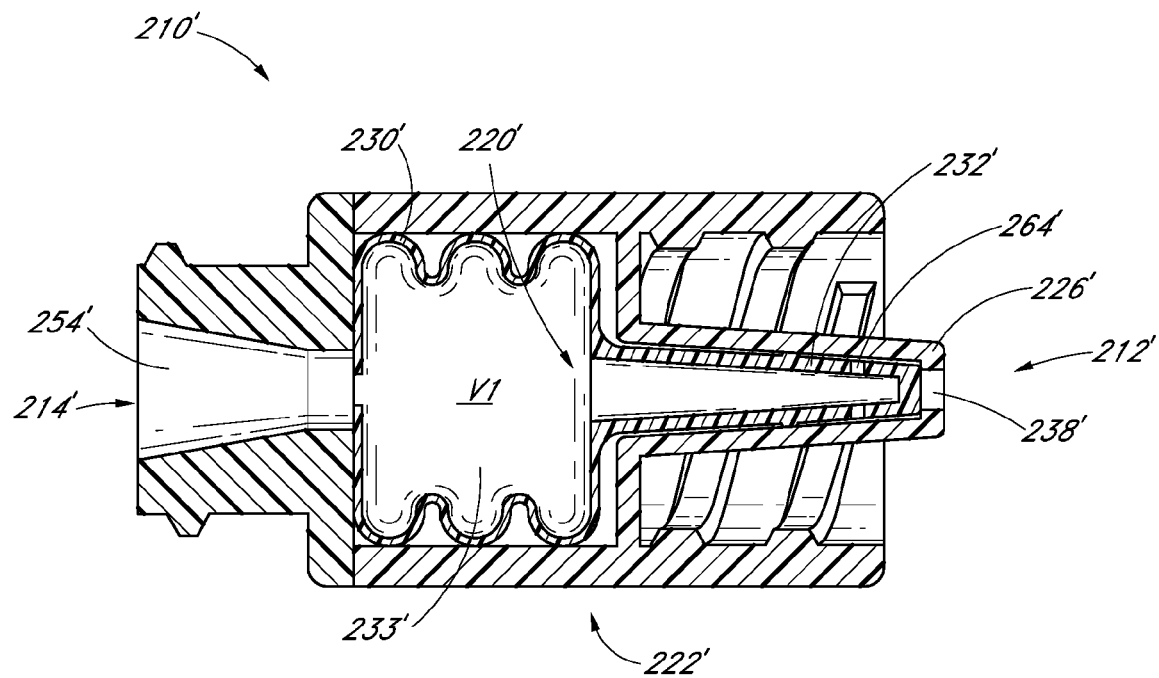
FIG. 5C is a cross-sectional view of another embodiment of a luer connector in a closed position.
Figure 5D:
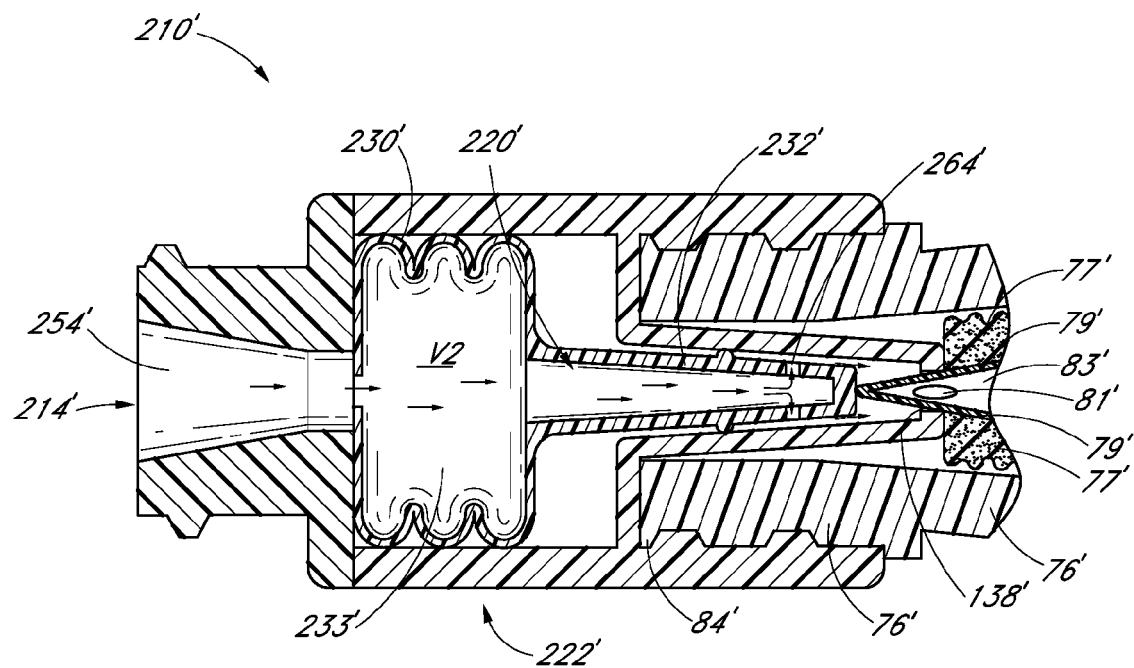
FIG. 5D is a cross-sectional view of the embodiment of the luer connector shown in FIG. 5C in an open position.

Referring now to FIGS. 5C-5D, some embodiments of the closeable luer connector 210' will be described. In some embodiments, the luer connector 210' may comprise any of the components, features, materials, sizes, geometries, details, or configurations of any of the other luer connectors disclosed herein. FIG. 5C is a cross-sectional view of the luer connector 210' in a closed position such that fluid is generally prevented from flowing through the luer connector 210'. FIG. 5D is a cross-sectional view of the embodiment of the luer connector 210' in an open position due to the engagement of a female connector 76' with the luer connector. The flow of fluid or medicament through the luer connector 210' is represented by arrows in FIG. 5D. As described above, when the valve member 210' of the luer connector 210' is in the open position, fluid can be generally permitted to flow through the luer connector 210'.

In some embodiments, the luer connector 210' can be the same or similar to the luer connector 210' described above, with certain differences in some version as illustrated and/or described below. In some embodiments, as in the illustrated embodiment, the valve member 220' can be moved from the closed position (as illustrated in FIG. 5C) to the open position (as illustrated in FIG. 5D) without the use of the actuators or struts 236 as described above with respect to luer connector 210. With reference to FIG. 5D, the luer connector 210' can be threadedly engaged with the closeable female connector 76'. The closeable female connector tip 82' of the female connector 76' can have a radially extending surface 84' disposed on its external surface that can engage with the inner threads formed on the inside surface of the shroud 228' of the luer connector 210' to engage the connectors 210', 76' as illustrated. In the illustrated engagement, the fluid conduit 79' of the female connector 76' can advance through the opening 238' in the luer tip 226' by displacing the tube 232' toward the second end 214' of the luer connector 210'. The tube 232' can be configured so as to compress the bladder member 230' when the tube 232' is displaced as illustrated in FIG. 5D, and to return to its closed position within luer tip 226' (as illustrated in FIG. 5C) when the female connector 76' is disengaged from the luer connector 210'. As the bladder member 230' is compressed, the volume of the cavity 233' within the bladder member 230' can decrease and exert a force on the tube 232' so as to return the tube 232' to the closed position within luer tip 226' (as illustrated in FIG. 5C) when the female connector 76' can be disengaged from the luer connector 210'. The change in volume can further result in a vacuum like effect, as discussed in connection with other embodiments disclosed herein, that can draw fluid from the first end 212' toward the bladder member 230'.

Further, as illustrated, as the fluid conduit 79' of the female connector 76' advances through the opening 238' in the luer tip 226', a compressible seal element 77' surrounding the fluid conduit 79' can be compressed so as to allow the fluid conduit 79' to protrude therethrough. The force exerted while engaging the connectors 210', 76' can be sufficient to compress the seal element 77' to expose the one or more openings 81' in the fluid conduit 79'. With the seal element 77' compressed, the fluid passageway 83' can be in fluid communication with the interior space of the luer tip 232'. As can be seen in FIG. 5D, the front surface of the fore portion 226a' can contact the front surface of the sealing member 77' so as to create and maintain a generally fluid tight seal therewith. The compressed seal element 77' can inhibit fluid flowing into the interior of the closeable female connector 76' beyond the luer tip 232'. In this configuration, fluid can flow from the second end 214' of the luer connector 210', through at least the fluid passageway 254', the bladder member 230', the tube 232', the one or more openings 264' in the tube 232', the opening 238' in the luer tip 226', through the one or more openings 81' in the female connector 76', and through the fluid passageway 83'. Thus, in the engaged position, the fluid conduit 79' can protrude through the compressible seal element 77' to a sufficient extent so that the fluid passageway 83' of the female connector 76' can be in fluid communication with the fluid passageway 254' of the luer connector 210'. In some embodiments, the luer connector 210' may also comprise struts (not shown) as described above to allow the valve 220' to be opened and closed, even if a female connector of the type illustrated in FIG. 5D is used.

Figure 6A:
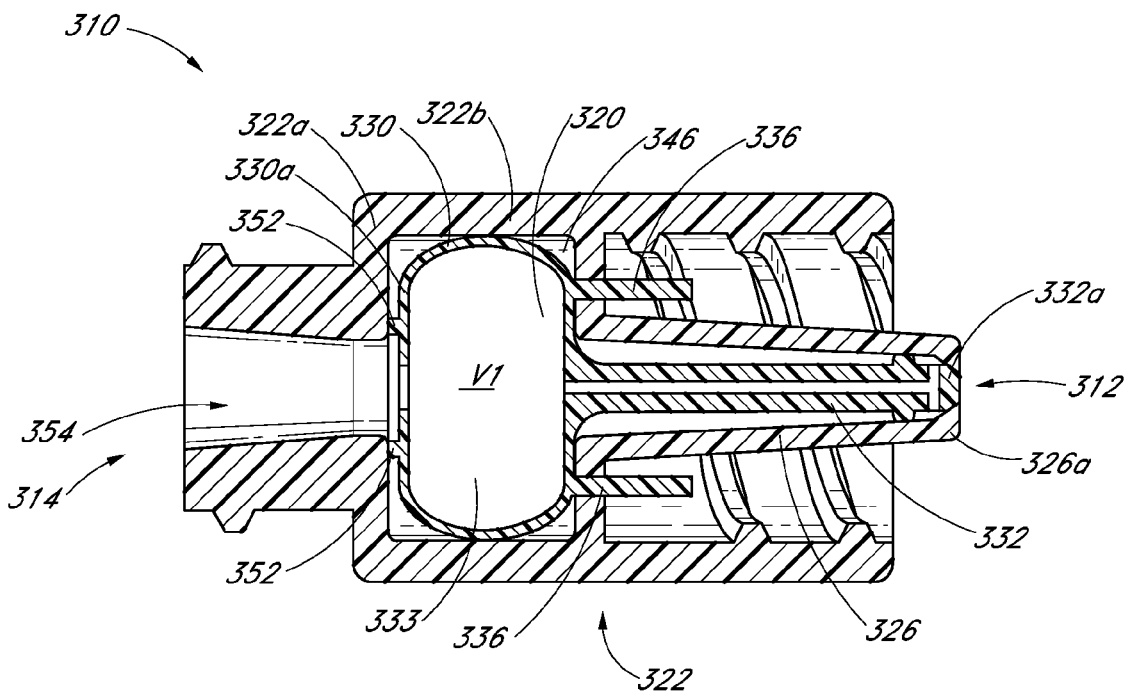
FIG. 6A is a cross-sectional view of another embodiment of a luer connector in a closed position.
Figure 6B:
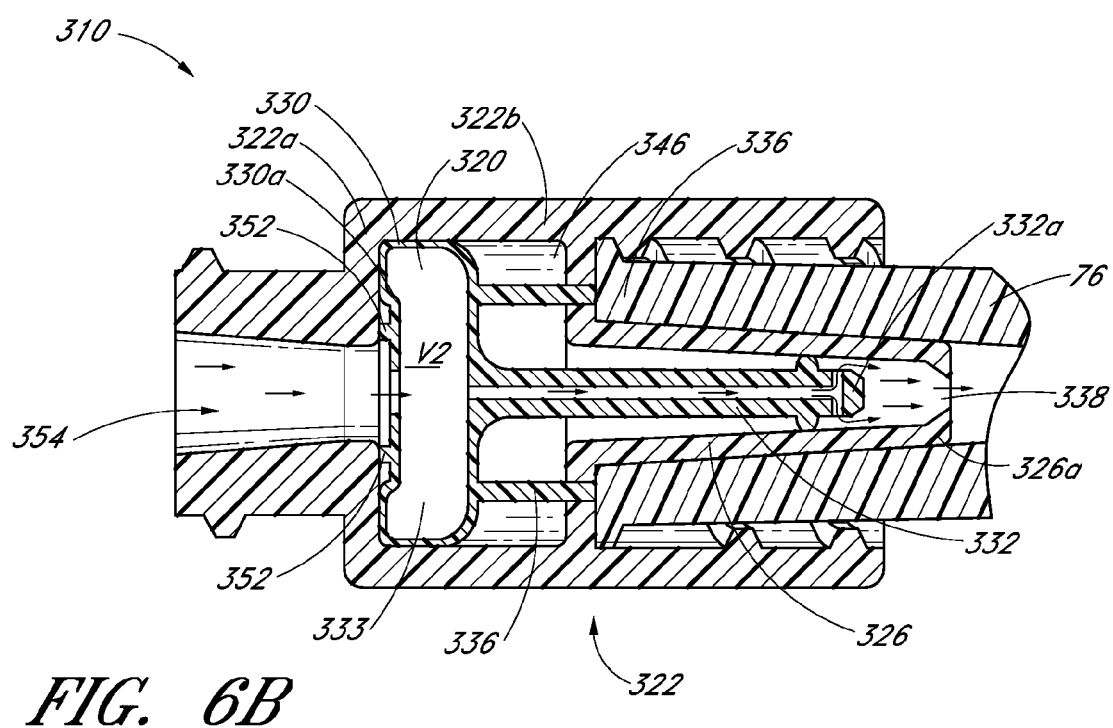
FIG. 6B is a cross-sectional view of the embodiment of the luer connector shown in FIG. 6A in an open position.

Referring now to FIGS. 6A-6B, some embodiments of the closeable luer connector 310 will be described. In some embodiments, the luer connector 310 may comprise any of the components, features, materials, sizes, geometries, details, or configurations of any of the other luer connectors disclosed herein. FIG. 6A is a cross-sectional view of the luer connector 310 in a closed position such that fluid is generally prevented from flowing through the luer connector 310. FIG. 6B is a cross-sectional view of the embodiment of the luer connector 310 in an open position due to the engagement of a female connector 76 with the luer connector. The flow of fluid or medicament through the luer connector 310 is represented by arrows in FIG. 6B. As described above, when the valve member 320 of the luer connector 310 is in the open position, fluid can be generally permitted to flow through the luer connector 310.

In some embodiments, the luer connector 310 can be the same or similar to the luer connector 110 described above, with certain differences in some versions as illustrated and/or described below. Accordingly, in some embodiments, the luer connector 310 may operate in the same or similar manner as compared to the luer connector 110 described above. In some embodiments, the bladder member 330, the tube 332, and the valve struts 336 may all be integrally formed. In some embodiments, the bladder member 330, the tube 332, and the valve struts 336 may be all formed from the same material, such as a resilient rubber material like silicone, or may each be formed from a different material and adhered, bonded, fused, or otherwise attached together in a suitable manner. As with any of the valve struts described above, the valve struts 336 can be suitably rigid and otherwise configured such that, when a female connector 76 is threadingly engaged with the luer connector 310, the struts 336 can be axially depressed toward the bladder member 330, causing the bladder member 330 to compress. Additionally, in some embodiments, the bladder member 330 may define a bellows-type shape, as illustrated in FIGS. 5A and 5B above. In some embodiments, the bladder member 330 preferably defines an internal cavity 333 with a volume that increases as the valve member 320 moves from the open position to the closed position to effect a suction of fluid from the first end 312 toward the second end 314 of the connector.

In some embodiments, the aft portion 330a of the bellows 330 may define a sealing member 352 that can be configured to seal the aft portion 330a of the bladder member 330 to the aft portion 322a of the housing to 322 so as to prevent any fluid or medicaments passing through the luer connector 310 from leaking into the chamber 346 within the housing 322 during operation. In some embodiments, the sealing member 352 may define an annular shape and may be positioned between the bladder member 330 and the aft portion 322a of the housing 322. In some embodiments, the sealing member 352 may be integrally formed with the bladder member 330. Additionally, the complementary mating surfaces of the end portion 332a of the tube 332 as well as the end portion 326a of the luer tip 326 can define alternative shapes and sizes as compared to other portions of the luer connectors disclosed herein, as illustrated in FIGS. 6A and 6B. The shapes, sizes, features, or any other aspects of the luer connector 310 illustrated in FIGS. 6A and 6B can be implemented in any luer connector disclosed herein.

Figure 6C:
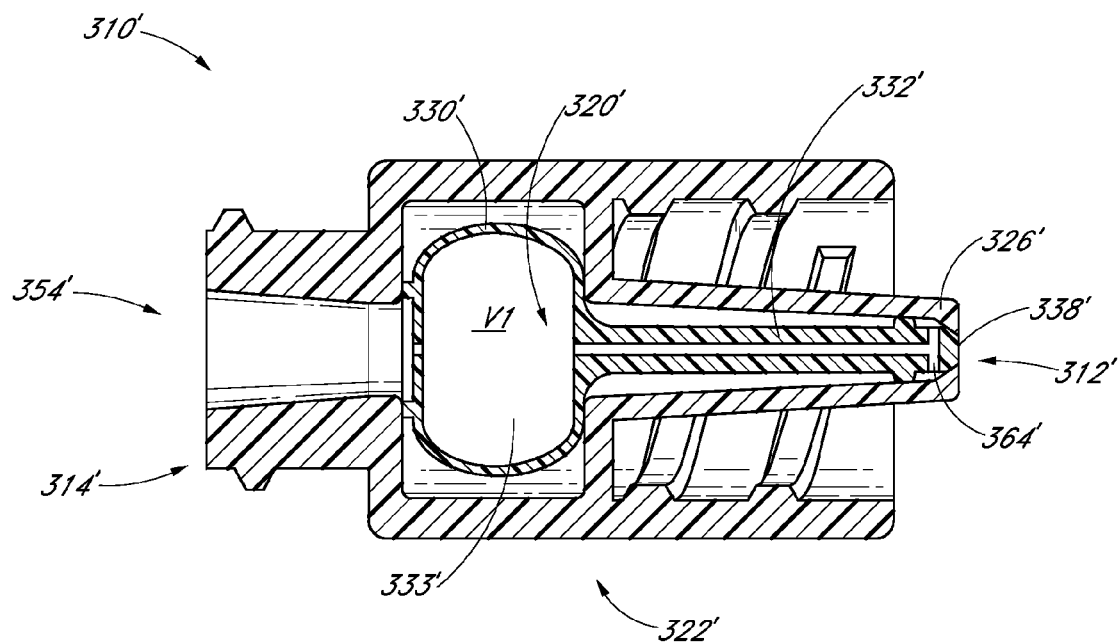
FIG. 6C is a cross-sectional view of another embodiment of a luer connector in a closed position.
Figure 6D:
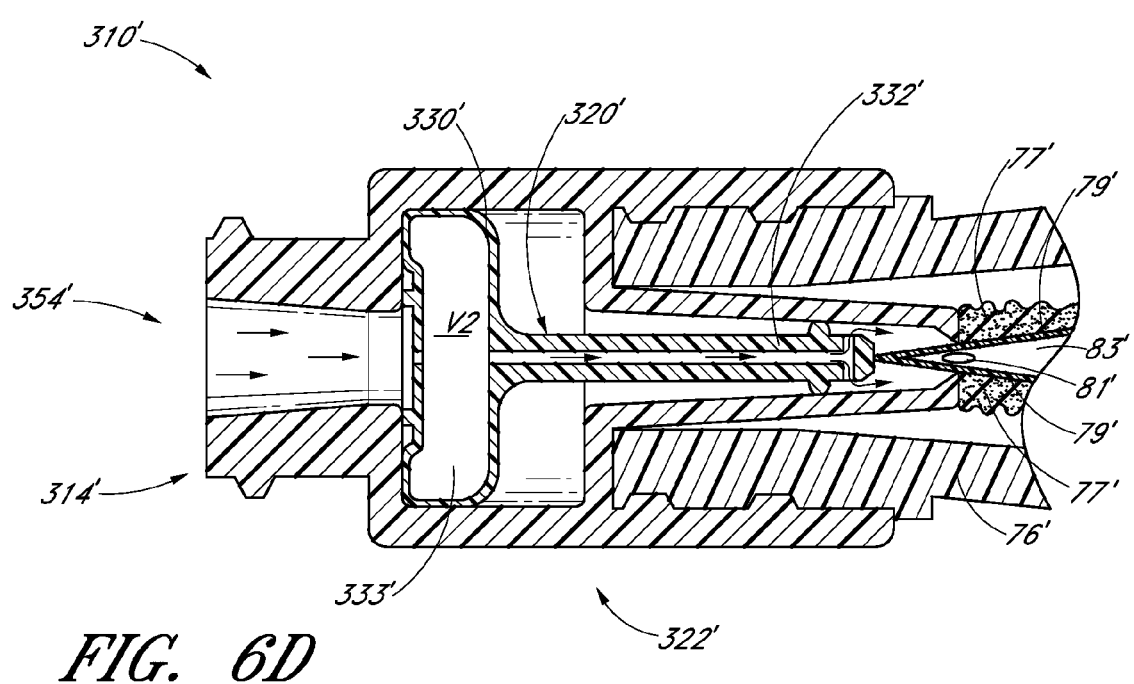
FIG. 6D is a cross-sectional view of the embodiment of the luer connector shown in FIG. 6C in an open position.

Referring now to FIGS. 6C-6D, some embodiments of the closeable luer connector 310' will be described in greater detail. In some embodiments, the luer connector 310' may comprise any of the components, features, materials, sizes, geometries, details, or configurations of any of the other luer connectors disclosed herein. FIG. 6C is a cross-sectional view of the luer connector 310' in a closed position such that fluid is generally prevented from flowing through the luer connector 310'. FIG. 6D is a cross-sectional view of the embodiment of the luer connector 310' in an open position due to the engagement of a female connector 76' with the luer connector. The flow of fluid or medicament through the luer connector 310' is represented by arrows in FIG. 6D. As described above, when the valve member 310' of the luer connector 310' is in the open position, fluid can be generally permitted to flow through the luer connector 310'.

In some embodiments, the luer connector 310' can be the same or similar to the luer connector 310 described above, with certain differences in some versions as illustrated and/or described below. In some embodiments, as in the illustrated embodiment, the valve member 320' can be moved from the closed position (as illustrated in FIG. 6C) to the open position (as illustrated in FIG. 6D) without the use of the actuators or struts 336 as described above with respect to luer connector 310. With reference to FIG. 6D, the luer connector 310' can be threadedly engaged with the closeable female connector 76'. The closeable female connector tip 82' of the female connector 76' can have a radially extending surface 84' disposed on its external surface that can engage with the inner threads formed on the inside surface of the shroud 328' of the luer connector 310' to engage the connectors 310', 76' as illustrated. In the illustrated engagement, the fluid conduit 79' of the female connector 76' can advance through the opening 338' in the luer tip 326' by displacing the tube 332' toward the second end 314' of the luer connector 310'. The tube 332' can be configured so as to compress the bladder member 330' when the tube 332' is displaced as illustrated in FIG. 6D. As the bladder member 330' is compressed, the volume of the cavity 333' within the bladder member 330' can decrease and exerts a force on the tube 332' so as to return the tube 332' to the closed position within luer tip 326' (as illustrated in FIG. 6C) when the female connector 76' is disengaged from the luer connector 310'. Additionally, in some embodiments, the volume of space within the cavity 333' of the bladder member 330' can increase as the valve member 320' returns to the closed position, creating a suction force that can draw excess fluid from the interior of the luer tip 326' into the bladder member 330'.

Further, as illustrated, as the fluid conduit 79' of the female connector 76' advances through the opening 338' in the luer tip 326', a compressible seal element 77' surrounding the fluid conduit 79' can be compressed so as to allow the fluid conduit 79' to protrude therethrough. The force exerted to engage the connectors 310', 76' can be sufficient to compress the seal element 77' to expose the one or more openings 81' in the fluid conduit 79'. With the seal element 77' compressed, the fluid passageway 83' can be in fluid communication with the interior space of the luer tip 332'. As can be seen in FIG. 6D, the front surface of the fore portion 326a' can contact the front surface of the sealing member 77' so as to create and maintain a generally fluid tight seal therewith. The compressed seal element 77' can inhibit fluid flow into the interior of the closeable female connector 76' beyond the luer tip 332'. In this configuration, fluid can flow from the second end 314' of the luer connector 310', through at least the fluid passageway 354', the bladder member 330', the tube 332', the one or more openings 364' in the tube 332', the opening 338' in the luer tip 326', through the one or more openings 81' in the female connector 76', and through the fluid passageway 83'. Thus, in the engaged position, the fluid conduit 79' can protrude through the compressible seal element 77' to a sufficient extent so that the fluid passageway 83' of the female connector 76' is in fluid communication fluid passageway 354' of the luer connector 310'. In some embodiments, the luer connector 310' may also comprise struts (not shown) as described above to allow the valve 320' to be opened and closed, even if a female connector of the type illustrated in FIG. 6D is used.

Figure 7A:
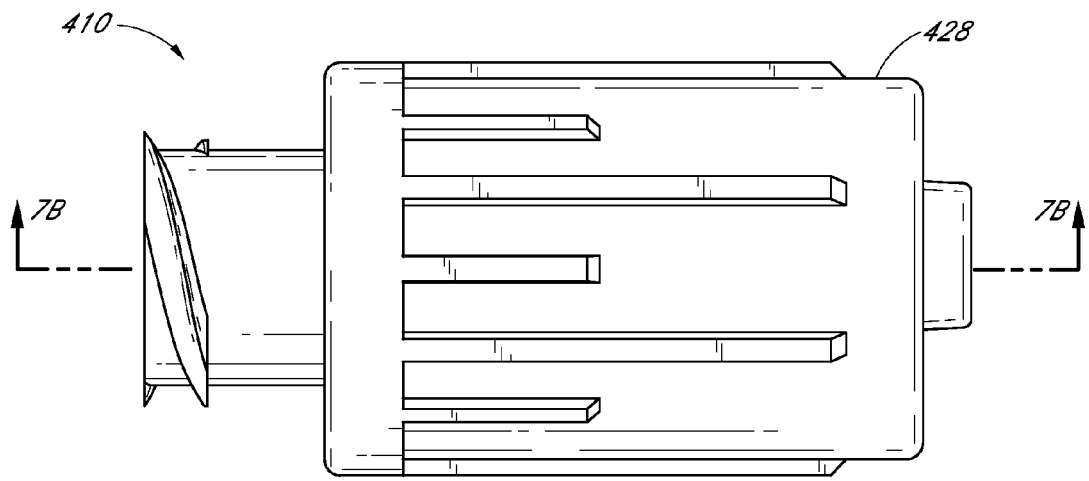
FIG. 7A is a side view of another embodiment of a luer connector.
Figure 7B:
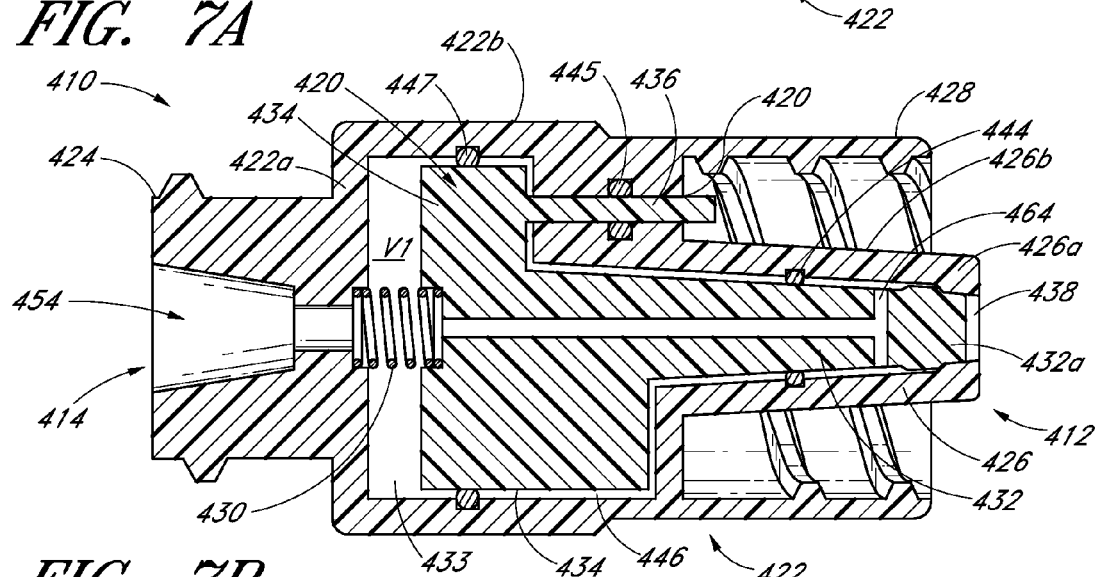
FIG. 7B is a cross-sectional view of the embodiment of the luer connector shown in FIG. 7A in a closed position.
Figure 7C:
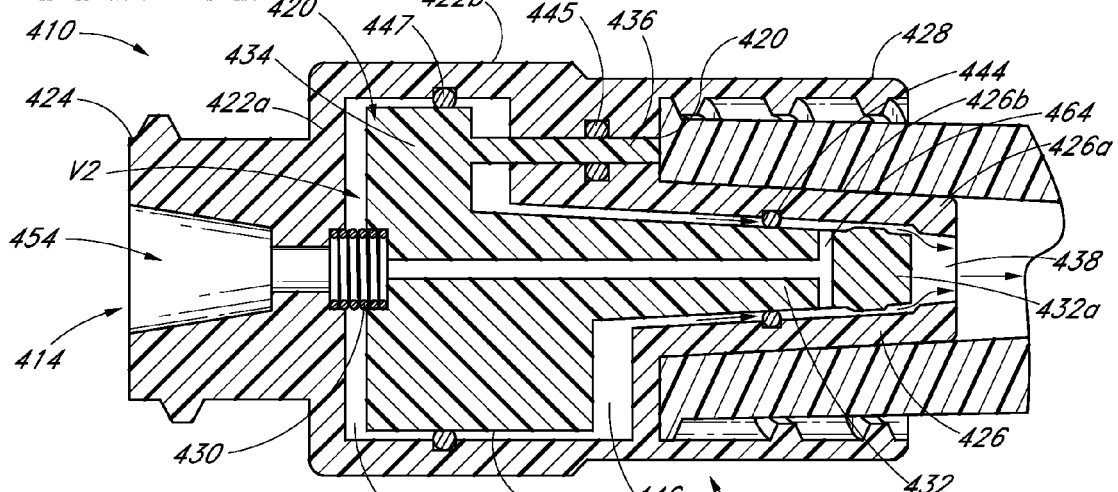
FIG. 7C is a cross-sectional view of the embodiment of the luer connector shown in FIG. 7A in an open position.

Referring now to FIGS. 7A-7C, some embodiments of the closeable luer connector 410 will now be described. In some embodiments, the luer connector 410 may comprise any of the components, features, materials, sizes, geometries, details, or configurations of any of the other luer connectors disclosed herein. Detail and description of components or features that are similar to those of other luer connectors or other devices disclosed herein may be limited or omitted.

FIG. 7A is a side view of the outside of the embodiment of the luer connector 410. FIG. 7B is a cross-sectional view of the luer connector 410 in a closed position so that fluid is generally prevented from flowing through the luer connector 410. FIG. 7B is a cross-sectional view of the luer connector 410, showing the valve member 420 in an open position configured to permit the flow of fluid through the luer connector 410.

As illustrated in FIG. 7A, some embodiments of the assembled luer connector 410 can comprise a housing 422, a port 424 positioned near the second or distal end 414 of the luer connector 410, a luer tip 426 positioned near the first or proximal end 412 of the luer connector 410, a shroud 428 surrounding at least a portion of the luer tip 426, a resilient spring member 430 supported within the housing 422, and the valve member 420 mentioned above also supported within the housing 422. In some embodiments, the spring member 430 may be helical in shape and formed from a metallic material, such as stainless steel, spring alloy, or other suitable metallic material, or from a suitable plastic or rubber material in a helical shape or in the shape of a solid, hollow, or perforated cylinder.

In the illustrated embodiment, the valve member 420 can comprise a tube 432 projecting from a valve base 434 toward the first end 412 of the connector 410, and a valve strut 436 that can project from the valve base 434. In some embodiments, in an assembled configuration, the luer connector 410 may comprise more than one valve strut 436, each of which can be positioned so as to be adjacent to the tip 426 along two sides of the tip 426. When the luer connector 410 is in the closed position, the outer surface of the distal portion 432a of the valve tube 432 can be sealingly closed against the inner surface of the distal portion 426a of the luer tip 426 such that fluid is generally prevented from flowing through the opening 438 formed in the distal and 426a of the luer tip 426.

In the illustrated embodiment, the tube 432 can be slidably supported so as to translate axially within the luer tip 426. Further, the valve struts 436 that can be supported in a cantilevered disposition by the valve base 434 can be configured so as to slide within the openings 440 formed through the internal wall 442 of the housing 422. The number of openings 440 through the internal wall 442 can be equal to the number of the valve struts 436 that can be supported by the valve base 434. A sealing member 444 (which can define an annular shape) can be positioned around the outside surface of the tube 432 so as to provide a seal between the outside surface of the tube 432 and the inside surface of the luer tip 426 during the operation of the luer connector 410 (i.e., as the valve member 420 moves between the open and the closed positions). In some embodiments, the sealing member 444 may be integrally formed with the luer tip 426 or may be separately formed and fused to, adhered to, or otherwise attached to or supported by the luer tip 426. In some embodiments, the sealing member 444 may be integrally formed with the tube 432 or may be separately formed and fused to, adhered to, or otherwise attached to or supported by the tube 432.

Additionally, an annular sealing member 445 can be positioned around the outside surface of each of the valve struts 436 so as to provide a seal between each of the valve struts 436 and each of the openings 440 in the internal wall 442, so as to prevent any fluid from flowing through the opening or openings 440 into the chamber 446. In the illustrated embodiment, the chamber 433 is the space that is generally confined by the end wall 422a of the housing 422, the sidewall 422b (which can be cylindrically shaped) of the housing 422, and the internal wall 442 formed in the housing 422. Some embodiments of the luer connector 410 can comprise a sealing member 447 which, in some embodiments, can be annular, around the outside surface 434a (which can be cylindrically shaped) of the valve base 434. In some embodiments, the luer connector 410 can be configured such that the sealing member 447 remains in a constant position relative to the valve base 434 so as to move with the valve base 434 as the valve member 420 moves between the open and the closed position.

In the illustrated embodiment, the spring member 430 can be supported near the second end 414 of the luer connector 410 by the end wall 422a of the housing 422 and at the other end by the valve base 434. The spring member 430 can comprise an axial opening through the center thereof through which fluid or medicament can pass. Additionally, in some embodiments, a fluid may pass between the coils of the spring member 430. The spring member 430 can be resilient and biased toward an expanded position, as illustrated in FIG. 7B, so as to exert a force on the valve member 420 that biases the valve member 420 toward the closed position. In some embodiments, as the valve member 420 moves relative to the housing 422, the preferably resilient spring member 430 will compress, causing the spring member 430 to exert a force on the valve member 420 that can bias the valve member 420 toward the closed position. The biasing force from the spring member 430 can be resisted by the threaded engagement of the female connector 76 with the luer connector 410. However, when the female connector 76 is withdrawn from the male luer 410, the spring member 430 can return the sealing portion of the valve member 420 to the closed position within the luer tip 426.

In some embodiments, luer connector 410 can be configured so that the volume within the chamber 433 between the sealing member 447 the valve base 443, and the end wall 422a of the housing when the valve member 420 is in the closed position (which is represented by V1 in FIG. 7B) can be greater than volume within the chamber 433 between the sealing member 447, the valve base 434, and the end wall 422a when the valve member 420 is in the open position (which is represented by V2 in FIG. 7C). In these embodiments, the sealing member 447 can move with the valve base 434 along a portion of the inside surface of the sidewall 422b of the housing 422. In some embodiments, the sidewall 422b of the housing 422 can define a generally cylindrical shape. Thus, in these embodiments, the volume of space within the portion of the chamber 433 described above can increase when the valve member 420 moves from the open position to the closed position, so as to create a force of suction that can reduce the amount of fluid or medicament that can flow through or drip out of the opening 438, or to retract dripping fluid back into the opening 438, as the valve member 420 is closed.

In some embodiments, any of the features of the valve member 420, including the valve tube 432, the valve base 434, and the valve struts 436 can be integrally formed, or in other embodiments, can be separately formed and adhered or otherwise joined together in subsequent manufacturing steps. In some embodiments, the end wall 422a can be formed integrally with at least the sidewalls 422b of the housing 422. In some embodiments, the end wall 422a can be formed separately as compared to at least the sidewalls 422b and joined or adhered thereto in a subsequent manufacturing step.

The housing 422 can be generally a tube-like structure with a passageway 454 that can extend from the second end 414 of the connector 410 through the axial center of the luer connector 410. Thus, in some embodiments, when the luer connector 410 is in the open configuration as illustrated in FIG. 7C, the passageway 454 can permit fluid to flow from the second end 414 through the port 424, the spring member 430, the tube 432, and out through the opening 438 in the luer tip 426 positioned at the first end 412 of the luer connector 410. With reference to FIGS. 7B and 7C, near the second end 414 of the luer connector 410, the port 424 and the corresponding section of the fluid passageway 454 can be adapted to accommodate a section of standard-diameter medical tubing inserted therein or a standard male luer tip.

FIG. 7C is a cross-sectional view of the luer connector 410 of the luer connector 410 in an open position so that fluid is generally permitted to flow through the luer connector 410. The flow of fluid or medicament through the luer connector 410 is represented by arrows in FIG. 7C. With reference to FIG. 7C, the valve member 420 has preferably been moved to the open position by the insertion the female connector 76. As shown in FIG. 7C and discussed above, the struts 436 of the valve member 420 can extend through openings 440 in the internal wall 442 of the housing 422 such that, in the closed position, the ends of the struts 436 extend past the internal wall 442 toward the first end 412 of the connector 410. As with other luer connectors described above, the struts 436 can be configured to engage the proximal ends 84 of the female connector 76 as the female connector 76 advances into engagement with the closeable male luer 410. FIG. 7C illustrates a cross-section of an embodiment of the luer connector 410 wherein the valve member 420 has been caused to be opened by the insertion of an exemplifying female connector 76 in a similar manner as other luer connectors comprising struts described above.

As shown in FIG. 7C, the two connectors 410, 76 can be threadedly engaged toward one another until the taper of the inner surface 86 of the female luer connector 76 lies adjacent to or abuts the correspondingly tapered external surface 426b of the tip 426, or until two luers 410, 76 can be sealingly engaged and the valve member 420 has been moved to the open position (as described above or in connection with any similarly configured luer connectors or valve members). In other embodiments, the two luers 410, 76 may be threadedly engaged until the second end of the tip 426 forms a closure with a corresponding surface (not shown) of the female connector 76.

Additionally, when used with certain alternative embodiments of the female connector 76 an internal fluid conduit of the female connector 76 may contact the distal end portion 432a of the tube 432 before the housing of the female connector 76 contacts the struts 436 (if any), thereby opening the male connector 410. In some embodiments, the closure may remain intact until the inner surface 86 of the tip of the female connector 76 has formed a closing engagement with the outer surface of the tip 426 of the luer connector 410, inhibiting fluid within the passageway 454 of the luer connector 410 from being exposed to the external environment.

Figure 7D:
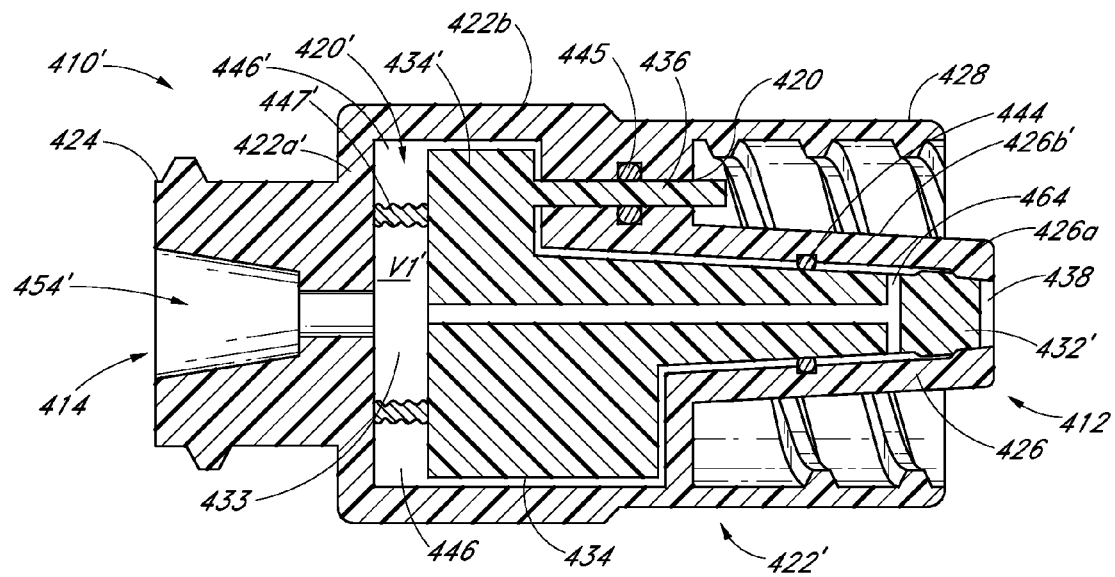
FIG. 7D is a cross-sectional view of another embodiment of a luer connector in a closed position.
Figure 7E:
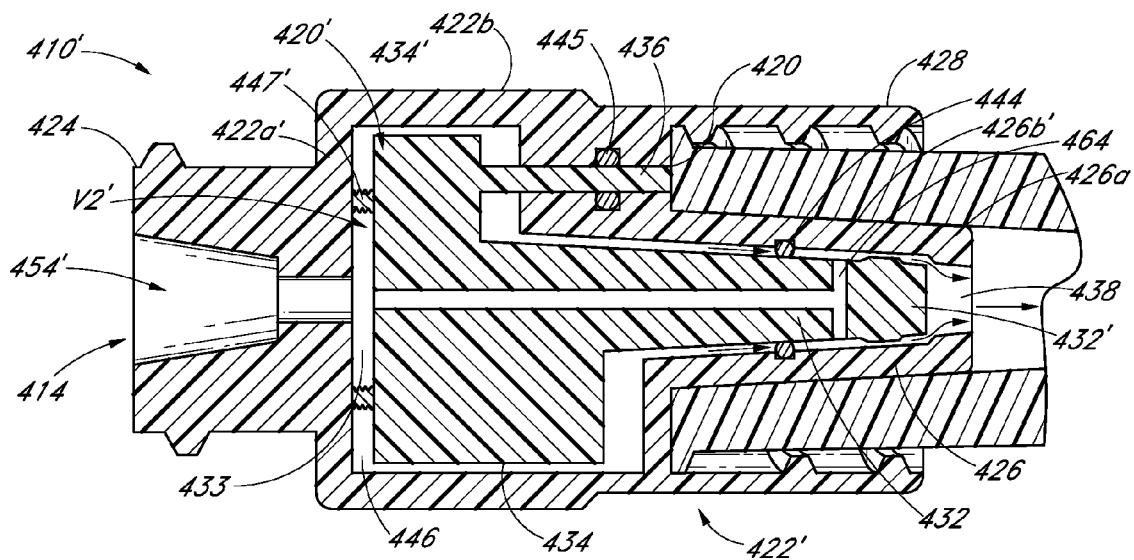
FIG. 7E is a cross-sectional view of the embodiment of the luer connector shown in FIG. 7D in an open position.

Referring now to FIGS. 7D-7E, some embodiments of the closeable luer connector 410' will be described in greater detail. In some embodiments, the luer connector 410' may comprise any of the components, features, materials, sizes, geometries, details, or configurations of any of the other luer connectors disclosed herein. In particular, in the illustrated embodiment, the luer connector 410' can be formed and configured to have the same features as the luer connector 410 described above, with the exception of the spring member 430 and the sealing member 447 of the luer connector 410, which will now be described.

With reference to FIG. 7D, the sealing member 447' can be positioned between the preferably generally planar surface of the valve base 434' and the preferably generally planar interior surface of the end wall 422a'. In some embodiments, the valve base 434' in the interior surface of the end wall 422a' may define a depression or other features to support the sealing member 447'. Additionally, in some embodiments, the sealing member 447' may be secured to either the valve base 434' or the interior surface of the end wall 422a' with an adhesive or by any other suitable method. As illustrated in FIGS. 7D and 7E, the sealing member 447' may provide a generally fluid tight seal to prevent fluid that is flowing through the passageway 454' from leaking into the cavity 446' outside of the sealing member 447'. Additionally, as with other embodiments of luer connectors described above, the luer connector 410' can be configured to provide a reduced pressure or suction so as to draw fluid from the opening or openings 464 within the luer tip 426 into the sealing member 447' as the valve member 420' moves to the closed position.

In particular, similar to other luer connectors described above, the volume of space of the cavity 433' generally formed within the sealing member 447' when the luer connector 410' is in the closed position (which is represented by V1' in FIG. 7D) can be larger than the volume of space within of the cavity 433' of the sealing member 447' when the luer connector 410' is in the open position (which is represented by V2' in FIG. 7D). The increase in the volume of the cavity 433' within the sealing member 447' as the valve member 420' moves from the closed to the open position can create a reduced pressure that draws the fluid from the luer tip 426' or tube 432' back into the passageway 454'.

Additionally, in some embodiments, the sealing member 447' may be formed from a resilient material such as, but not limited to, silicone, rubber, or other suitable material, that exerts a tensile force on the valve base 434' as the sealing member 447' is being compressed (i.e., when the valve member 420' is moved from the closed to the open position). In these embodiments, the tensile force created by the sealing member 447' can bias the valve member 420' toward the closed position, so that a separate spring member is not required. However, in some embodiments, the luer connector 410' may comprise both the sealing member 447' and an axial spring member, similar to any of the spring members described above. Further, in some embodiments, an axial spring member made from a suitable metal or any other suitable material may be formed integrally with the sealing member 447'.

Figure 7F:
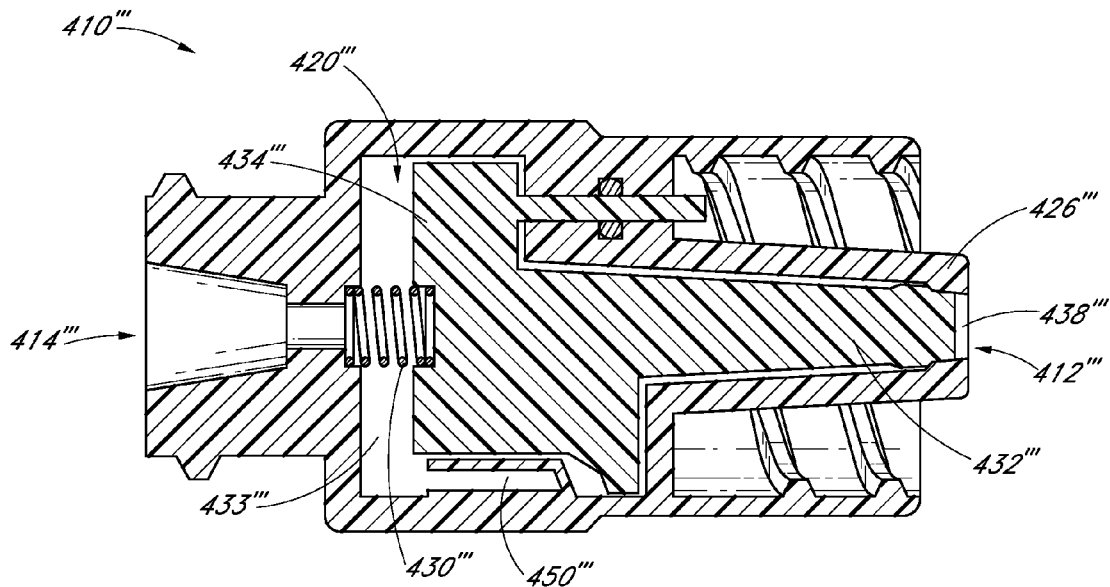
FIG. 7F is a cross-sectional view of another embodiment of a luer connector in a closed position.
Figure 7G:
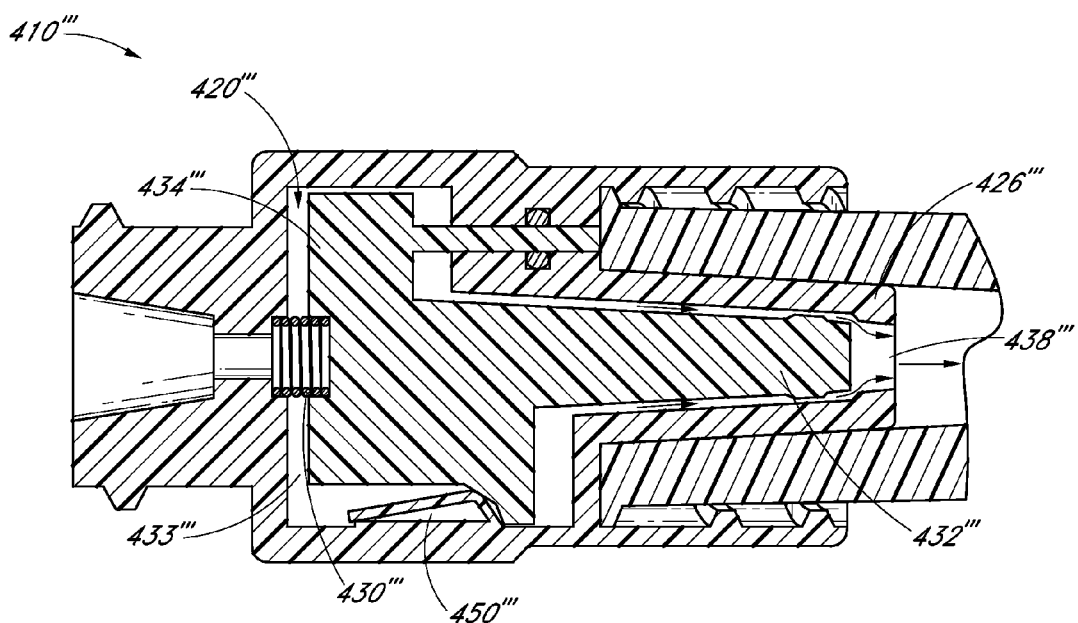
FIG. 7G is a cross-sectional view of the embodiment of the luer connector shown in FIG. 7F in an open position.

Referring now to FIGS. 7F-7G, some embodiments of the closeable luer connector 410" will be described in greater detail. In some embodiments, the luer connector 410" may comprise any of the components, features, materials, sizes, geometries, details, or configurations of any of the other luer connectors disclosed herein. For example, in the illustrated embodiment, the luer connector 410" can be formed and configured to have the same features as the luer connector 410, with certain differences in some versions as described below. The valve member 420" can be configured so that the fluid flow path goes around the valve member 420" instead of through an internal opening in the valve member as described above with respect to luer connector 410. Accordingly, the luer connector 410" can be formed so as to not have a sealing member surrounding the valve member 420", which would otherwise obstruct the fluid flow path.

Additionally, in the illustrated embodiment, the luer connector 410" can be configured to generally prevent leakage through the opening 438" at the end of the luer tip 426" as the valve member 420" is moved to the closed position. In particular, the luer connector 410" can comprise a vacuum member 450" that can be configured so as to provide a source of reduced pressure to the chamber 433" as the valve member 420" is moving towards the closed position.

Figure 8A:
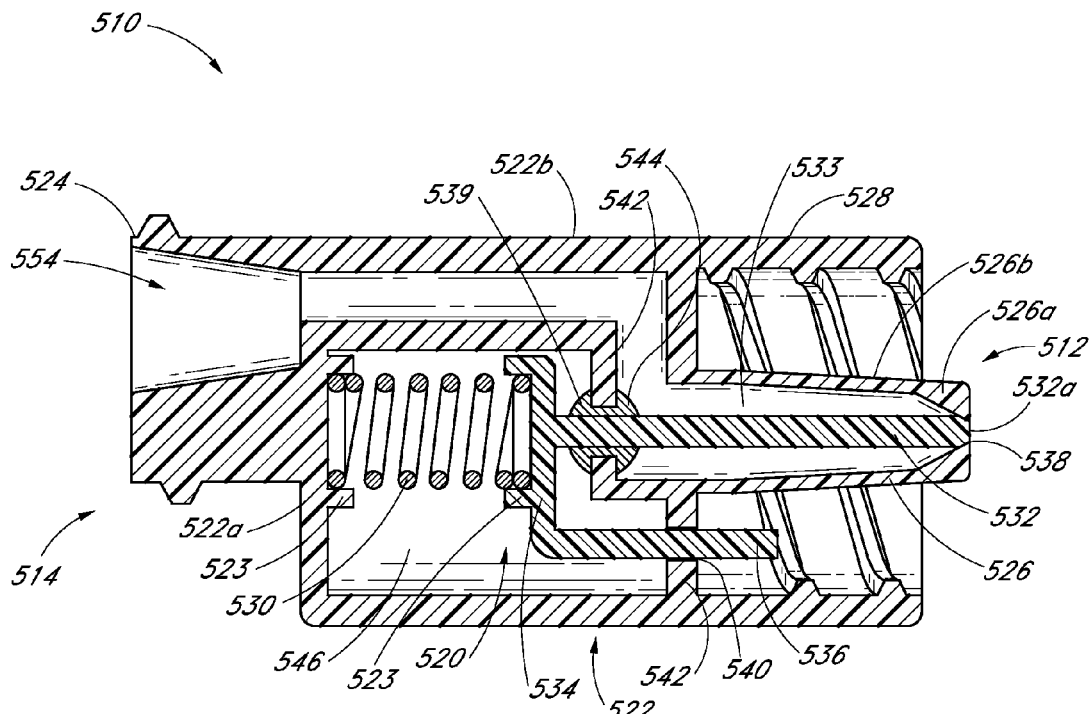
FIG. 8A is a cross-sectional view of another embodiment of a luer connector in a closed position.
Figure 8B:
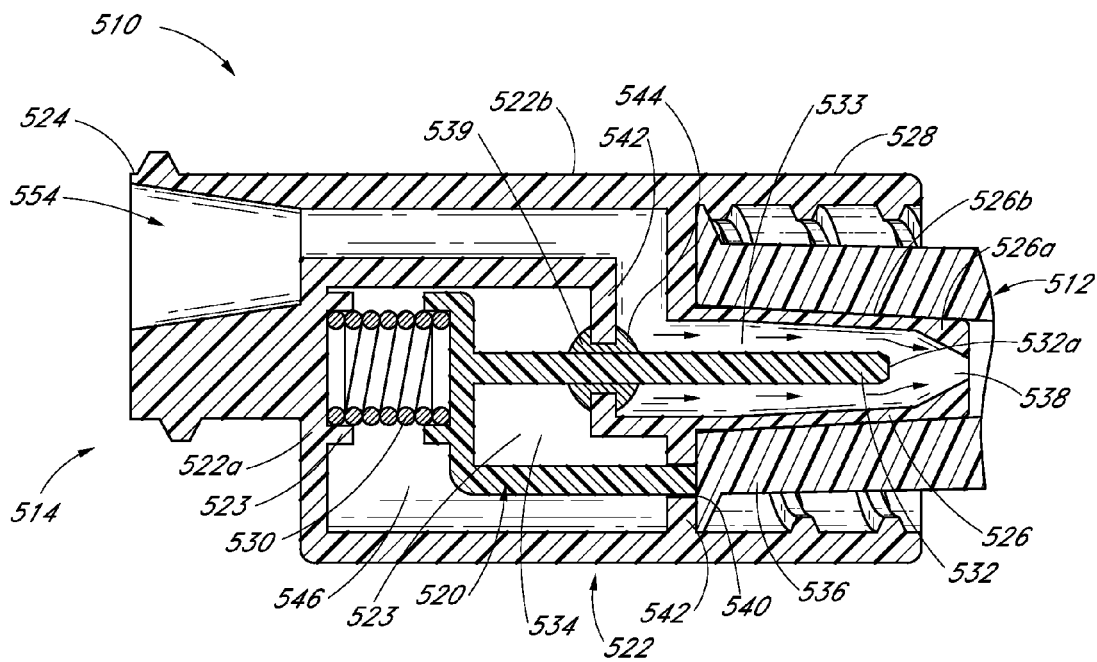
FIG. 8B is a cross-sectional view of the embodiment of the luer connector shown in FIG. 8A in an open position.

Referring now to FIGS. 8A-8B, some embodiments of the closeable luer connector 510 will now be described. In some embodiments, the luer connector 510 may comprise any of the components, features, materials, sizes, geometries, details, or configurations of any of the other luer connectors disclosed herein. Detail and description of components or features that are similar to those of other luer connectors or other devices disclosed herein may be limited or omitted.

FIG. 8A is a cross-sectional view of the luer connector 510 in a closed position so that fluid is generally prevented from flowing through the luer connector 510. FIG. 8B is a cross-sectional view of the luer connector 510 in an open position. The flow of fluid or medicament through the luer connector 510 is represented by arrows in FIG. 8B. In the open position, the valve member 520 can be adapted to facilitate the flow of fluid through the luer connector 510 by opening a channel through the connector 510.

As illustrated in FIG. 8A, some embodiments of the assembled luer connector 510 can comprise a housing 522, a port 524 positioned near the second end 514 of the luer connector 510, a luer tip 526 positioned near the first end 512 of the luer connector 510, a shroud 528 surrounding at least a portion of the luer tip 526, a resilient spring member 530 supported within the housing 522, and the valve member 520 mentioned above also supported within the housing 522. In some embodiments, the spring member 530 may be helical in shape and formed from a metallic material, such as stainless steel, spring alloy, or other suitable metallic material. In some embodiments, the spring member 530 may be formed from a suitable plastic or rubber material, and may be formed in a helical shape, or in the shape of a solid or hollow cylinder. In some embodiments, as in the illustrated embodiment, the valve base 534 and the end portion 522a of the housing 522 can be configured to provide lateral support to the end portions spring member 530 so as to prevent the end portions of the spring member 530 from moving in a transverse direction. In particular, the valve base 534 and the end portion 522a of the housing 522 may define protrusions 523 that can circumscribe the end portions of the spring member 530. In other embodiments, valve base 534 and the end portion 522a may comprise other features such as, but not limited to, depressions, channels, adhesive or other suitable materials or features to suitably secure the end portion of the spring member 530.

In the illustrated embodiment, the valve member 520 can comprise a tube 532 projecting from a valve base 534 toward the first end 512 of the connector 510, and a valve strut 536 that can also project from the valve base 534. In some embodiments, in an assembled configuration, the luer connector 510 may comprise more than one valve strut 536, each of which can be positioned so as to be adjacent to the tip 526 along two sides of the tip 526. When the valve member 520 of the luer connector 510 is in the closed position, the outer surface of the distal portion 532a of the valve tube 532 can be sealingly closed against the inner surface of the distal portion 526a of the luer tip 526 such that fluid can be generally prevented from flowing through the opening 538 formed in the distal and 526a of the luer tip 526. In some embodiments, the end portion 532a of the tube 532 can comprise any size, geometry, material or materials, or other features or details as would be suitable for the tube 532, or as described above with regard to any other tubes disclosed herein.

In the illustrated embodiment, the tube 532 can be slidably supported so as to translate axially within an opening 539 in the internal wall 542 of the housing 522, as well as to translate axially within the luer tip 526. Further, the valve strut 536 can be supported in a cantilevered disposition by the valve base 534 and can be configured so as to slide within the opening 540 formed through the internal wall 542 of the housing 522. In some embodiments, the luer connector 510 may comprise a seal between the valve strut 536 and the opening 540 to prevent fluid from leaking into the chamber 546. The number of openings 540 through the internal wall 542 can be equal to the number of the valve struts 536 that can be supported by the valve base 534.

A sealing member 544 (which can be generally annular in shape) can be positioned around the outside surface of the tube 532 so as to seal the opening 539 as the tube 532 slides axially therethrough during the operation of the luer connector 510 (i.e., as the valve 520 moves between the open and the closed positions). In some embodiments, the sealing member 544 may be integrally formed with the luer tip 526 or may be separately formed and fused to, adhered to, or otherwise attached to or supported by the luer tip 526. In some embodiments, the sealing member 544 may be integrally formed with the internal wall 542 of the housing 522 or may be separately formed and fused to, adhered to, or otherwise attached to or supported by the internal wall 542 of the housing 522.

In the illustrated embodiment, the spring member 530 can be supported near the second end 514 of the luer connector 510 by the end wall 522a of the housing 522 and at the other end by the valve base 534. The spring member 530 can be resilient and biased toward an expanded position, as illustrated in FIG. 8A, so as to exert a force on the valve member 520 that biases the valve member 520 toward the closed position. In some embodiments, as the valve member 520 moves relative to the housing 522, the spring member 530 can compress, increasing the force that is exerted on the valve member 520. The biasing force from the spring member 530 can be resisted by the threaded engagement of the female connector 76 with the luer connector 510. However, when the female connector 76 is withdrawn from the luer connector 510, the spring member 530 can return the sealing portion of the valve member 520 to the closed position within the luer tip 526.

In some embodiments, any of the features of the valve member 520, including the valve tube 532, the valve base 534, and the valve struts 536 can be integrally formed, or, in other embodiments, can be separately formed and adhered or otherwise joined together in subsequent manufacturing steps. In some embodiments, the end wall 522a can be formed integrally with at least the sidewalls 522b of the housing 522. In some embodiments, the end wall 522a can be formed separately as compared to at least the sidewalls 522b and joined or adhered thereto in a subsequent manufacturing step.

The housing 522 can be generally a tube-like structure with a passageway 554 that can extend from the second end 514 of the connector 510. With reference to FIGS. 8A and 8B, the fluid passageway 554 can channel the fluid or medicament flowing through the luer connector 510 around the chamber 546 in which the valve base 534 and spring member 530 can be positioned. The passageway 554 defines a cavity 533. In some embodiments, routing the fluid passageway 554 around the chamber 546 may decrease the volume of the cavity 533 within the passageway 554 which can increase the fluid volume efficiency of the luer connector 510, i.e., it can reduce the amount of fluid that may be trapped in the luer connector 510 when the valve member 520 is closed. Thus, in some embodiments, when the luer connector 510 is in the open configuration as illustrated in FIG. 8B, the passageway 554 can permit fluid to flow from the second end 514 through the passageway 554 and out through the opening 538 in the luer tip 526. As shown in FIG. 8B, in the opened configuration, the fluid passageway 80 of the female connector 76 can communicate with the passageway 554 of the valve member 520 so as to allow fluid to through the passageway 554 and the fluid passageway 80 of the female connector 76 in either direction.

With reference to FIG. 8B, as with certain other luer connectors disclosed herein, the valve member 520 has preferably been moved to the open position by the insertion the female connector 76. As shown in FIG. 8B, the struts 536 of the valve member 520 can extend through openings 540 in the internal wall 542 of the housing 522 such that, in the closed position, the ends of the struts 536 extend past the internal wall 542 toward the first end 512 of the connector 510.

As shown in FIG. 8B, the two connectors 510, 76 can be threadedly engaged towards one another until the taper of the inner surface 86 of the female luer connector 76 lies adjacent to or abuts the correspondingly tapered external surface 526b of the tip 526, or until two luers 510, 76 are sealingly engaged and the valve member 520 has been moved to the open position (as described above or in connection with any similarly configured luer connectors or valve members). In some embodiments, the two luers 510, 76 may be threadedly engaged until the second end of the tip 526 forms a closure with a corresponding surface (not shown) of the female connector 76.

Additionally, when used with certain alternative embodiments of the female connector 76, an internal fluid conduit of the female connector 76 may contact the distal end portion 532a of the tube 532 before the housing of the female connector 76 contacts the struts 536 (if any), thereby opening the male connector 510. In some embodiments, the closure may remain intact until the inner surface 86 of the tip of the female connector 76 has formed a closing engagement with the outer surface of the tip 526 of the luer connector 510, preventing any fluid within the passageway 554 of the luer connector 510 from ever being exposed to the external environment.

Figure 8C:
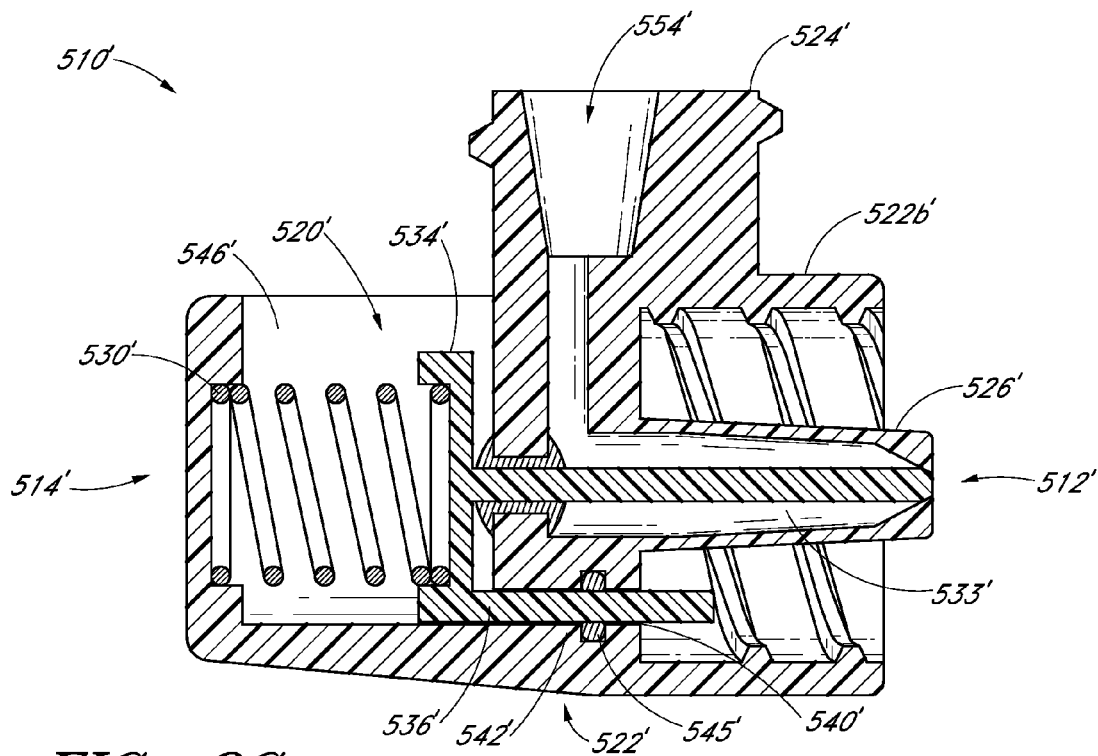
FIG. 8C is a cross-sectional view of another embodiment of a luer connector in a closed position.
Figure 8D:
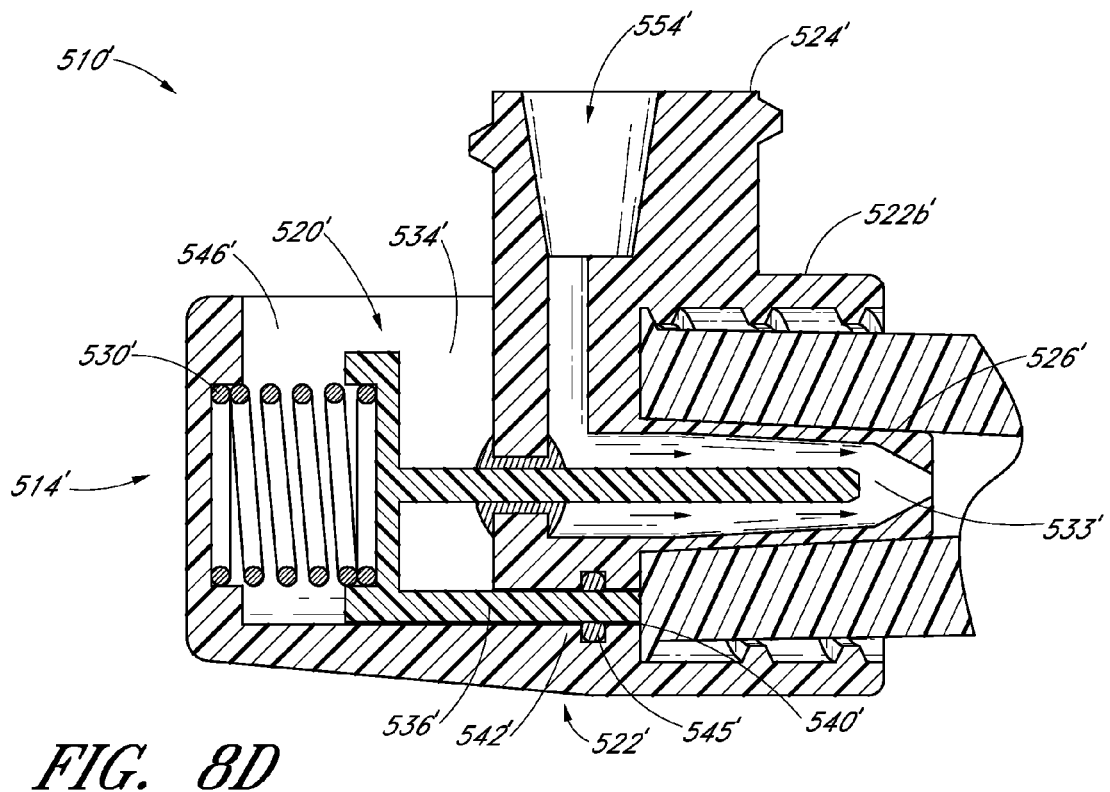
FIG. 8D is a cross-sectional view of the embodiment of the luer connector shown in FIG. 8C in an open position.

With reference to FIGS. 8C and 8D, another configuration of the luer connector 510 will be described. With reference to FIGS. 8C and 8D, the luer connector 510' may comprise any of the components, features, materials, sizes, geometries, details, or configurations of any of the other luer connectors disclosed herein. For example, the luer connector 510' can be configured so that the port 524' of the luer connector 510' is positioned to protrude from a side wall 522b' of the housing 522'. In the illustrated embodiment, the luer connector 510' can be formed and configured to have the same or similar features as the luer connector 510 described above with some differences. The luer connector 510' can be configured so that the port 524' of the luer connector 510' is positioned to protrude from a side wall 522b' of the housing 522'.

Accordingly, the luer connector 510' can be configured such that the fluid passageway 554' flowing into the port 524' can be oriented at an approximately 90 degree angle as compared to the fluid flow path within the luer tip 526'. This arrangement, as illustrated in FIGS. 8C and 8D, may facilitate the attachment of the luer connector 510' to particular connectors at the port 524' portion or at the first end 512' of the luer connector 510'. The passageway 554' can further define a fluid cavity 533' of the connector 510'.

Additionally, in some embodiments, the chamber 546' in which the spring member 530' and the valve base member 534' can be positioned may define an open portion (as in the illustrated embodiments), which may provide access to the spring member 530' and portions of the valve member 520'. Additionally, in some embodiments, the luer connector 510' may comprise an annular sealing member 545' that can be positioned around the outside surface of each of the valve struts 536' so as to provide a seal between each of the valve struts 536' and each of the openings 540' in the internal wall 542', so as to prevent fluid from flowing through the opening or openings 540' into the chamber 546', where such fluid could potentially flow to the chamber 546' and come into contact with the patient or medical practitioner using the luer connector 510'.

Any features of the embodiments shown and/or described in the Figures that have not been expressly described in this text, such as distances, proportions of components, etc. are also intended to form part of this disclosure. Additionally, although disclosed in the context of various embodiments, features, aspects, and examples, it will be understood by those skilled in the art that the present disclosure extends beyond the specifically disclosed embodiments to other alternative embodiments and/or uses and obvious modifications and equivalents thereof. Accordingly, it should be understood that various features and aspects of the disclosed embodiments can be combined with, or substituted for, one another in order to perform varying modes of the disclosure. Thus, it is intended that the scope of the present disclosure should not be limited by the particular disclosed embodiments described above.

The following is claimed:

1. A medical connector, comprising:
a substantially rigid housing having a first end, a second end, and a wall extending between the first and second ends and having an inside surface that is laterally spaced apart from an axial centerline of the connector, said first and second ends being connected by a selectively closable fluid passageway;
said first end including a hollow male luer with an inner surface, a first open end, and a second base end; a first valve member supported substantially within the housing, the first valve member being configured to selectively seal an opening adjacent to the first end of the housing at the tip of the male luer when the connector is in a closed position; and an internal bladder member positioned within the housing and outside the male luer, the bladder member defining an inner cavity and being fluidly coupled to the first valve member, the inner cavity of the bladder member having a first volume when the connector is in a closed position and a second volume smaller than the first volume when the connector is in an open position; wherein: the inner cavity is configured to fill with fluid during use and configured to be in fluid communication with the first end and the second end of the housing in both the open and closed positions; a wall of the bladder member extends radially against the inside surface of the housing when the connector is in both the open position and the closed position; and the rigid housing extends laterally from the base of the male luer and a valve arm extends through the housing adjacent the base of the male luer, a first end of the valve arm configured to engage a corresponding female end of a medical implement and a second end of the valve arm configured to engage at least a portion of the bladder member.

2. The medical connector of claim 1, further comprising a plurality of valve arms, said valve arms being connected by a ring.

3. The medical connector of claim 1, wherein the bladder member includes a wall portion being concave toward a longitudinal axis of the connector so as to form a substantially ovular inner cavity.

4. The medical connector of claim 1, wherein the bladder member includes a corrugated wall portion.

5. The medical connector of claim 1, wherein at least a portion of the valve member and at least a portion of the bladder member are integrally formed.

6. The medical connector of claim 1, further comprising an annular ring between the valve member and the inner surface of the male luer.

7. The medical connector of claim 6, wherein the annular ring is integrally formed with the valve member, the ring being in sliding engagement with the inner surface of the male luer.

8. The medical connector of claim 6, wherein the inner surface of the male luer includes an annular channel, said annular ring being recessed into said annular channel and being in sliding engagement with an outer surface of the valve member.

9. A method for selectively closing a medical connector, comprising:
supporting a resilient bladder member within a housing, the housing having a first end and a second end, said first and second ends being connected by a selectively closable fluid passageway and said first end having a hollow male luer with an inner surface and an opening at an end thereof in fluid communication with the fluid passageway;
moving a valve member at least partially supported within the housing and extending into the hollow male luer between a connector open position and a connector closed position such that:
in the closed position, the valve member closes the opening at the end of the hollow male luer and thereby substantially prevents liquid from flowing through the fluid passageway; and
in the open position, the valve member permits liquid to pass through the fluid passageway; and
moving the bladder member between a first configuration having a first volume in the connector closed position and a second configuration having a second volume in the connector open position, the second volume being smaller than the first volume;
wherein:
the medical connector is configured such that the fluid passageway between the second end of the housing and the valve member is open in both the connector open position and the connector closed position;
the bladder member has an opening therethrough and an internal chamber in communication with the fluid passageway configured to fill with liquid during use of the medical connector;
the bladder member is supported within the housing so as to be outside the male luer; and
moving the bladder member between the first configuration and the second configuration comprises moving at least one valve arm between a first and a second position, the at least one valve arm being configured to engage a corresponding female end of a medical implement and having a second end thereof configured to engage at least a portion of the bladder member.

10. The method of claim 9, wherein moving the valve member between the connector open position and the connector closed position and moving the bladder member between the first configuration and the second configuration comprises engaging or disengaging the medical connector with or from a corresponding female end of a medical implement.

11. The method of claim 9, wherein moving the at least one valve arm between the first and the second position comprises engaging or disengaging the medical connector with or from a corresponding female end of a medical implement.

12. The method of claim 9, wherein the bladder member includes a corrugated wall portion.

13. A medical connector, comprising:
a substantially rigid housing having a first end and a second end, said first and second ends being connected by a selectively closable fluid passageway;
said first end including a hollow male luer with an inner surface, a first open end, and a second base end; an internal bladder member positioned within the housing and outside the male luer, the bladder member defining an inner cavity having a first volume when the connector is in a closed position and a second volume smaller than the first volume when the connector is in an open position; and a first valve member fluidly coupled to the bladder member comprising a tube integrally formed with the bladder member extending from the bladder member toward the first open end of the male luer, the tube being configured to selectively seal an opening adjacent to the first end of the housing at the tip of the male luer when the connector is in a closed position;
wherein: the inner cavity of the bladder member is configured to fill with fluid during use and configured to be in fluid communication with the first end and the second end of the housing in both the open and closed positions; the selectively closeable fluid passageway extends through the bladder member and the tube, and the rigid housing extends laterally from the base of the male luer and a valve arm extends through the housing adjacent the base of the male luer, a first end of the valve configured to engage a corresponding female end of a medical implement and a second end of the valve arm configured to engage at least a portion of the bladder member.

14. The medical connector of claim 13, further comprising a plurality of valve arms, said valve arms being connected by a ring.

15. The medical connector of claim 13, wherein the bladder member includes a wall portion being concave toward a longitudinal axis of the connector so as to form a substantially ovular inner cavity.

16. The medical connector of claim 13, wherein the bladder member includes a corrugated wall portion.

17. The medical connector of claim 13, further comprising an annular ring between the valve member and the inner surface of the male luer.

18. The medical connector of claim 17, wherein the annular ring is integrally formed with the valve member, the ring being in sliding engagement with the inner surface of the male luer.

19. The medical connector of claim 17, wherein the inner surface of the male luer includes an annular channel, said annular ring being recessed into said annular channel and being in sliding engagement with an outer surface of the valve member.

* * * * *